United States Patent
Yamagishi et al.

(10) Patent No.: US 8,252,790 B2
(45) Date of Patent: Aug. 28, 2012

(54) PYRAZOLE-3-CARBOXAMIDE DERIVATIVE HAVING 5-$HT_{2B}$ RECEPTOR ANTAGONIST ACTIVITY

(75) Inventors: Tatsuya Yamagishi, Chita-gun (JP); Kiyoshi Kawamura, Chita-gun (JP); Tadashi Inoue, Chita-gun (JP); Yuji Shishido, Chita-gun (JP); Hiroaki Ito, Chita-gun (JP)

(73) Assignee: Raqualia Pharma Inc., Aichi (JP)

( * ) Notice: Subject to any disclaimer, the term of this patent is extended or adjusted under 35 U.S.C. 154(b) by 0 days.

(21) Appl. No.: 13/129,916

(22) PCT Filed: Nov. 24, 2009

(86) PCT No.: PCT/JP2009/069816
§ 371 (c)(1),
(2), (4) Date: Jun. 13, 2011

(87) PCT Pub. No.: WO2010/058858
PCT Pub. Date: May 27, 2010

(65) Prior Publication Data
US 2011/0275628 A1 Nov. 10, 2011

(30) Foreign Application Priority Data

Nov. 21, 2008 (JP) .................. 2008-298821
May 1, 2009 (JP) .................. 2009-112344

(51) Int. Cl.
*A61K 31/5375* (2006.01)
*C07D 413/02* (2006.01)
(52) U.S. Cl. ............... 514/233.2; 514/234.5; 514/236.5; 514/235.8; 544/122; 544/124; 544/127; 544/140; 546/121
(58) Field of Classification Search ............. 514/233.2, 514/234.5, 236.5, 235.8; 544/122, 124, 127, 544/140; 546/121
See application file for complete search history.

(56) References Cited

U.S. PATENT DOCUMENTS

| 6,439,387 B1 | 8/2002 | Bergman |
| 2005/0203160 A1 | 9/2005 | Ackermann et al. |
| 2008/0021030 A1 | 1/2008 | Faucher et al. |

FOREIGN PATENT DOCUMENTS

| EP | 1 935 881 | 6/2008 |
| WO | 02/080899 | 10/2002 |
| WO | 2005/049578 | 6/2005 |
| WO | 2007/037513 | 4/2007 |
| WO | 2008/047883 | 4/2008 |

OTHER PUBLICATIONS

English translation of the International Preliminary Report on Patentability and Written Opinion dated Jul. 5, 2011.
International Search Report issued Dec. 22, 2009 in International (PCT) Application No. PCT/JP2009/069816.

*Primary Examiner* — Joseph K. McKane
*Assistant Examiner* — Samantha Shterengarts
(74) *Attorney, Agent, or Firm* — Wenderoth, Lind & Ponack, L.L.P.

(57) ABSTRACT

Disclosed is a compound represented by general formula (I) or a pharmaceutically acceptable salt thereof, which is useful as a selective antagonist of a 5-$HT_{2B}$ receptor. The compound and salt are useful for treatment or prevention of various diseases and conditions associated with a 5-$HT_{2B}$ receptor.

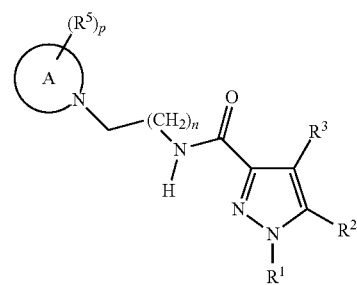

12 Claims, 1 Drawing Sheet

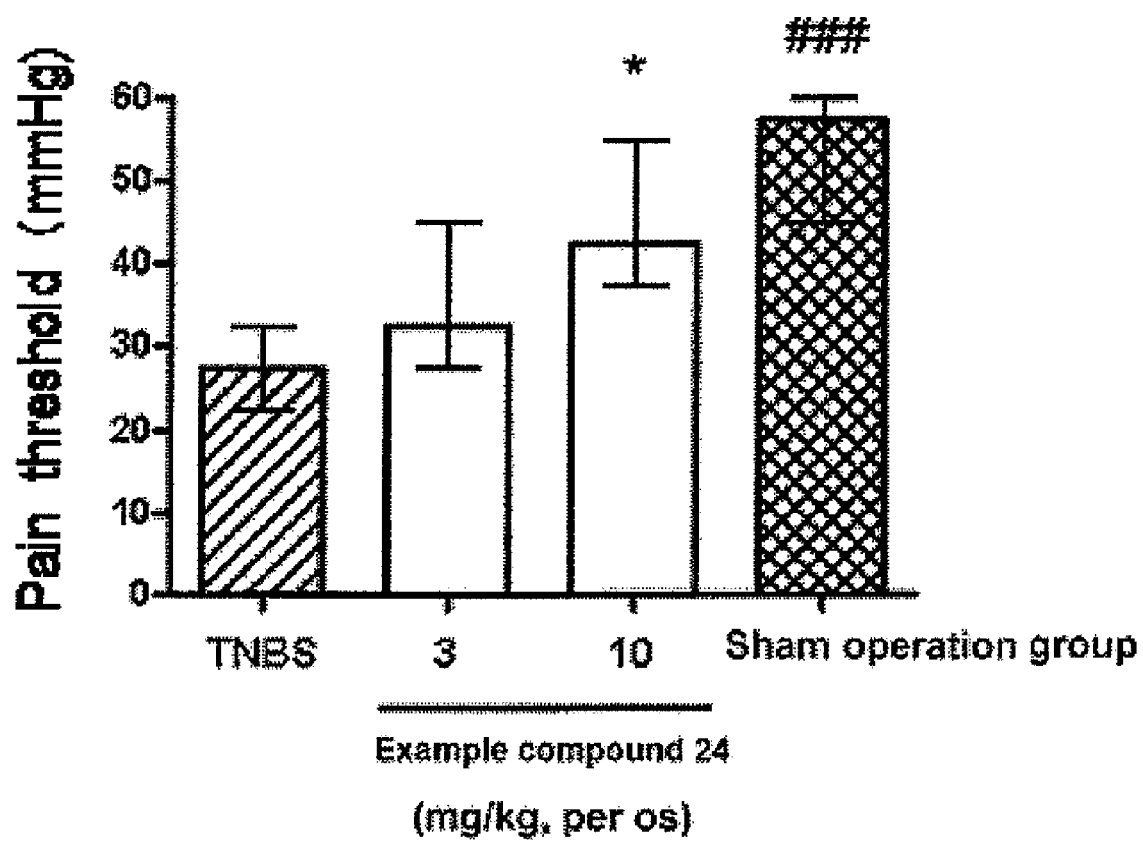
*P value <0.05, vs TNBS Control group
P value <0.001, vs TNBS Control group

PYRAZOLE-3-CARBOXAMIDE DERIVATIVE HAVING 5-HT$_{2B}$ RECEPTOR ANTAGONIST ACTIVITY

This application is a U.S. national stage of International Application No. PCT/W2009/069816 filed Nov. 24, 2009.

TECHNICAL FIELD

This invention relates to novel pyrazole-3-carboxamide derivatives. The compounds of this invention are useful compounds as selective 5-HT$_{2B}$ receptor antagonists and are useful for prevention or treatment of various diseases relating to this receptor. The present invention also relates to a pharmaceutical composition comprising the above derivatives.

BACKGROUND ART

Serotonin (5-hydroxytryptamine) which was first discovered in 1948 is one of the neurotransmitters and is one of the tryptamine derivatives, which distributed with high concentration to hypothalamic area, basal ganglion, medulla raphe nucleus and so on. Serotonin is a chemical substance contained in animals including human and is biosynthesized from tryptophan. About 10 mg of serotonin are found in human and the major part of them is distributed to chromatin cell in mucosa of small intestine. Serotonin synthesized here acts the muscle such as intestine and highly relates to the gastrointestinal tract motility. Serotonin is also found in the central nervous system and contributes mental activities in human. Much attention is being paid to the effect of serotonin from daily life to mental disorders such as depression and neurosis has been noticed. Recent years, the curative medicines against these diseases have been developed by using the medicines which effect to serotonin.

On the other hand serotonin is one of the G-protein-coupled receptors mainly in the central nervous system. Serotonin is categorized into 7 families from 5-HT$_1$ to 5-HT$_7$ and 14 subtypes are recognized. While the pharmacological investigations about each subtype has been continued (non-patent literature 1), three subtypes, 5-HT$_{2A}$, 5-HT$_{2B}$ and 5-HT$_{2C}$, are found in the 5-HT$_2$ family. Furthermore, on 5-HT$_{2B}$ receptor various pharmacological effects have been reported to be useful for prevention or treatment of various diseases.

In general, 5-HT$_{2B}$ receptor antagonists are found to be useful for prevention or treatment of a variety of diseases, including migraine, inflammatory pain, nociceptive pain, fibromyalgia, chronic low back pain, visceral pain, gastroesophageal reflux disease (GERD), constipation, diarrhea, functional gastrointestinal disorder, irritable bowel syndrome (hereafter it is called IBS for short). The definition and the criteria is described in ROME III, non-patent literature 2), asthma, osteoarthritis, rheumatoid arthritis, Crohn's disease, ulcerative colitis, glomerulonephritis, nephritis, dermatitis, hepatitis, vasculitis, renal ischemia, cerebral stroke, myocardial infarction, cerebral ischemia, Alzheimer's disease, reversible airway obstruction, adult respiratory disease syndrome, chronic obstructive pulmonary disease (COPD), pulmonary hypertension (PH), idiopathic interstitial pneumonia, bronchitis, liver fibrosis, cryptogenic fibrosing alveolitis, multiple sclerosis, depression, anxiety and obesity. (non-patent literatures 3 to 7)

In addition concerning 5-HT$_{2B}$ receptors, the relationship of the said receptor with apparatus digestorius and pulmonary artery is known based on the experiments using 5-HT$_{2B}$ selective inhibitors.

Concerning the role of apparatus digestorius, 5-HT$_{2B}$ receptor antagonists are useful for IBS based on depressing the human intestinal contraction by electrical stimulation (patent literature 1). It is described that 5-HT$_{2B}$ antagonists are effective for the treatment of functional bowel disorder based on the rat intestinal contraction by serotonin stimulation (patent literature 2). In addition, reducing the pain threshold against colonic distension is reported in rats treated by 2,4,6-trinitrobenzene sulfonic acid (called TNBS hereafter), which is regarded as a visceral hypersensitivity model (non-patent literature 8).

Furthermore, 5-HT$_{2B}$ antagonists depressed increasing defecation weight by stress in the stress-induced defecation model in rats generally regarded as an IBS model, which can be confirmed to be useful for diarrhea-predominant IBS. In addition, when stress is given to rats, the pain response increases against colonic distension, 5-HT$_{2B}$ agonists suppresses the increase of the pain response.

Concerning the role at pulmonary artery, it is described that 5-HT$_{2B}$ receptor relates to improving the chronically hypoxic mice model of pulmonary hypertension, 5-HT$_{2B}$ antagonistic compounds are effective for the treatment of pulmonary hypertension (non-patent literature 9). It is reported that 5-HT$_{2B}$ selective antagonists showed reducing blood pressure in the early phase II study against patients with pulmonary hypertension along with chronic obstructive pulmonary disease (COPD) in the double blind test using placebo as a reference (non-patent literature 10) where 5-HT$_{2B}$ selective antagonists has been confirmed their safety and usefulness in human.

CITATION LIST

Patent Literatures

Patent Literature 1: International publication 02/056010 pamphlet

Patent Literature 2: Japanese Unexamined Patent Application Publication (Translation of PCT Application) No. 1997-510216

Non-Patent Literatures

Non-patent Literature 1: Phamacol. Rev. 1994, 46, 157-203

Non-patent Literature 2: Drossman et al., Journal of Gastrointestinal and Liver Diseases (2006) Vol. 15 (3), 237-241

Non-patent Literature 3: Johnson KwCephalalgia 23(2): 117-23 (2003)

Non-patent Literature 4: Allman J M et al, TRENDS In Cognitive Sciences 9(8): 367-373 (2005)

Non-patent Literature 5: Borman R A et al, Br J. Pharmacol. 135 (5):114, 4-51 (2002)

Non-patent Literature 6: Beattie D T et al, Br J. Pharmacol. 143(5):549-60 (2004)

Non-patent Literature 7: Kubera M et al, Psychiatry Res. 30; 134(3):251-8 (2005)

Non-patent Literature 8: The Journal of Pharmacology and Experimental Therapeutics, Vol. 302, No. 3, 1013-1022 (2002); 2) Pharmacology (2008), 81(2), 144-150))

Non-patent Literature 9: Nature Medicine, 8(10):1129-1135, 2002

Non-patent Literature 10: PRX-08066: EPIX Pharmaceuticals

SUMMARY OF INVENTION

Technical Problem

The purpose of this invention is to provide a medicament or pharmaceutical composition which contains compounds with selective 5-$HT_{2B}$ receptor antagonistic activity as effective ingredients. In addition, by high selective receptor affinity and by reducing the relation to the other receptors, reducing various unfavourable actions, which 5-$HT_{2B}$ receptor antagonistic relates to, is also the purpose of the present invention.

Solution to Problem

Inventors of this invention in order to solve the said problem above discovered that novel pyrazole-3-carboxamide derivatives having the unique chemical structure show the selective and strong antagonistic activity against the 5-$HT_{2B}$ receptor among the serotonin receptor subtypes. In addition, they confirmed that novel pyrazole-3-carboxamide derivatives have improved effectively thresh-hold of the visceral pain in rat TNBS induced IBS model. Therefore novel 5-substituted-1H-pyrazole-3-carboxamide derivatives are useful for prevention or treatment of disease conditions mediated by the above receptor stimulation such as migraine, inflammatory pain, nociceptive pain, fibromyalgia, chronic low back pain, visceral pain, gastroesophageal reflux disease (GERD), constipation, diarrhea, functional gastrointestinal disorder, irritable bowel syndrome (IBS), asthma, osteoarthritis, rheumatoid arthritis, Crohn's disease, ulcerative colitis, glomerulonephritis, nephritis, dermatitis, hepatitis, vasculitis, renal ischemia, cerebral stroke, myocardial infarction, cerebral ischemia, Alzheimer's disease, reversible airway obstruction, adult respiratory disease syndrome, chronic obstructive pulmonary disease (COPD), pulmonary hypertension (PH), idiopathic interstitial pneumonia, bronchitis, liver fibrosis, cryptogenic fibrosing alveolitis, multiple sclerosis, depression, anxiety and obesity.

This invention has completed based on the above view and provides the following compounds or their pharmaceutical acceptable salts, the said compounds or their pharmaceutical acceptable salts, prevention or treatment agents of disease related to the 5-$HT_{2B}$ receptor as effective ingredients, pharmaceutical compositions containing the said compounds or the pharmaceutically acceptable salts, or method of treatment of the said compounds or the pharmaceutically acceptable salts.

Namely, the present invention is as follows:

[1] A compound of the following general formula ($I_0$) or its pharmaceutically acceptable salt,

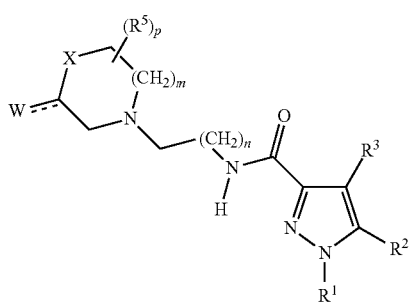

($I_0$)

[wherein, $R^1$ is a straight-chain, branched-chain or cyclic lower alkyl group having 1 to 6 carbon atoms, or a straight-chain, branched-chain or cyclic haloalkyl group having 1 to 6 carbon atoms;

$R^2$ is a (hetero)aryl ring group of the following general formula (Ar);

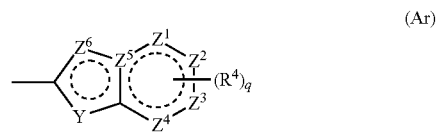

(Ar)

$R^3$ is a hydrogen or halogen atom;

$R^4$ is a straight-chain, branched-chain or cyclic lower alkyl group having 1 to 6 carbon atoms, a straight-chain, branched-chain or cyclic haloalkyl group having 1 to 6 carbon atoms, OH, $OR^{1A}$, halogen, —$(CH_2)aOH$, $CO_2H$, $CONH_2$, $CONHR^{1A}$, $CONR^{1A}R^{1A}$, CN, $COR^{1A}$, $NH_2$, $NHR^{1A}$, $NR^{1A}R^{1A}$, $NHCOR^{1A}$, $SR^{1A}$, $SOR^{1A}$, $SO_2R^{1A}$, $SO_2NH_2$, $SO_2NHR^{1A}$, $SO_2NR^{1A}R^{1A}$, or $NHSO_2R^{1A}$, when q is plural, $R^4$ may be same or different; when $R^4$ has two $R^{1A}$, they may be same or different, or $R^{1A}$ may combine with the other $R^{1A}$;

$R^5$ is a straight-chain, branched-chain or cyclic lower alkyl group having 1 to 6 carbon atoms, —$(CH_2)aOH$, —$(CH_2)aOR^{1B}$, halogen, $CONH_2$, $CONR^{1B}R^{1B}$, $COR^{1B}$, $SO_2R^{1B}$, —$OCH_2CH_2NR^{1B}R^{1B}$ or a straight-chain, branched-chain or cyclic haloalkyl group having 1 to 6 carbon atoms; when p is plural, $R^5$ may be same or different, or $R^5$ may combine with the other $R^5$;

$R^{1A}$ and $R^{1B}$ are each independently a straight-chain, branched-chain or cyclic lower alkyl group having 1 to 6 carbon atoms, or a straight-chain, branched-chain or cyclic haloalkyl group having 1 to 6 carbon atoms;

a is 0, 1, or 2;

m is 0, 1, or 2;

n is 1, or 2;

p is 0, 1, 2, 3, 4, or 5; and q is 0, 1, 2, or 3;

X is $CH_2$, NH, O, S, SO, $SO_2$, $CHR^5$, $CR^5R^5$ ($R^5$ is same as described above and may be same or different), or $NR^5$ ($R^5$ is same as described above);

W is an oxygen atom, (H, H), (H, $R^5$), or ($R^5$, $R^5$) when X is $CH_2$, NH, O, $CHR^5$, $CR^5R^5$, or $NR^5$, or W is (H, H), (H, $R^5$), or ($R^5$, $R^5$) when X is S, SO, or $SO_2$; wherein (H, H), (H, $R^5$), or ($R^5$, $R^5$) means that W represents two one valent groups, and the said two one valent groups are H and H, H and $R^5$, $R^5$ and $R^5$;

Y is NH, $NR^1$, O, or S;

$Z^1, Z^2, Z^3, Z^4, Z^5$, and $Z^6$ are each independently N, C, CH, or $CR^4$ ($R^4$ is same as described above and 1, 2, or 3 of $Z^1$ to $Z^6$ may represent a nitrogen atom)].

[2] A compound of the following general formula (I) or its pharmaceutically acceptable salt.

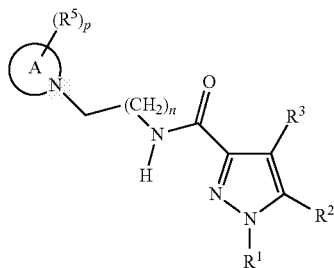

[wherein,
A is a 3 to 8 membered ring and may contain 0 to 4 heteroatoms selected from O, S, and N;
$R^1$ is a $C_1$-$C_6$ alkyl group, or a $C_1$-$C_6$ haloalkyl group;
$R^2$ is a saturated or partially or all unsaturated monocyclic or bicyclic aryl group, which may be substituted by $R^4$;
$R^3$ is a hydrogen or halogen atom;
$R^4$ is a $C_1$-$C_6$alkyl group, a $C_1$-$C_6$haloalkyl group, OH, $OR^{1A}$, halogen, —$(CH_2)aOH$, $CO_2H$, $CONH_2$, $CONHR^{1A}$, $CONR^{1A}R^{1A}$, CN, $COR^{1A}$, $NH_2$, $NHR^{1A}$, $NR^{1A}R^{1A}$, $NHCOR^{1A}$, $SR^{1A}$, $SOR^{1A}$, $SO_2R^{1A}$, $SO_2NH_2$, $SO_2NHR^{1A}$, $SO_2NR^{1A}R^{1A}$, or $NHSO_2R^{1A}$; when q is plural, $R^4$ may be same or different; when $R^4$ has two $R^{1A}$, they may be same or different or $R^{1A}$ may combine with the other $R^{1A}$;
$R^5$ is a $C_1$-$C_6$ alkyl group, —$(CH_2)aOH$, —$(CH_2)aOR^{1B}$, halogen, $CONH_2$, $CONR^{1B}R^{1B}$, $COR^{1B}$, $SO_2R^{1B}$, —$OCH_2CH_2NR^{1B}R^{1B}$ or a $C_1$-$C_6$ haloalkyl group; when p is plural, $R^5$ may be same or different, or $R^5$ may combine with the other $R^5$;
$R^{1A}$, $R^{1B}$ are each independently a $C_1$-$C_6$ alkyl group or a $C_1$-$C_6$ haloalkyl group;
a is 0, 1, or 2;
n is 1, or 2;
p is 0, 1, 2, 3, 4, or 5; and
q is 0, 1, 2, or 3.]

[3] The compound or the pharmaceutically acceptable salt thereof, as described in the above [2], wherein $R^2$ is the following $Ar^1$, $Ar^2$, $Ar^3$, or $Ar^4$,

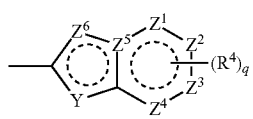
(Ar¹)

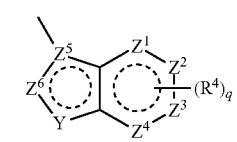
(Ar²)

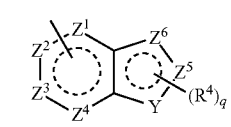
(Ar³)

[wherein,
$R^4$ and q are same as described in the above [2];
Y is NH, $NR^6$, O, or S;
$Z^1$, $Z^2$, $Z^3$, $Z^4$, $Z^5$, and $Z^6$ are each independently N, C, CH, or $CR^4$ (1, 2, or 3 of $Z^1$ to $Z^6$ may represent a nitrogen atom); and
$R^6$ is hydrogen, a $C_1$-$C_6$ alkyl group, a $C_1$-$C_6$ haloalkyl group, a $C_1$-$C_6$ alkoxy $C_1$-$C_6$ alkyl group, a hydroxyl $C_1$-$C_6$ alkyl group, a halo $C_1$-$C_6$ alkoxy $C_1$-$C_6$ alkyl group, a $diC_1$-$C_6$ alkylamino $C_1$-$C_6$ alkyl group, a mono $C_1$-$C_6$alkylamino $C_1$-$C_6$ alkyl group, an amino $C_1$-$C_6$ alkyl group, a $C_3$-$C_8$ cyclo $C_1$-$C_6$ alkyl group (said $C_3$-$C_8$ cyclo $C_1$-$C_6$ alkyl group may be substituted with 1 or 2 groups each independently selected from hydroxy, $C_1$-$C_6$alkoxy and $C_1$-$C_6$ acyloxy, and may have S(sulfur), O(oxygen) or $NR^1$), an aminocarbonyl $C_1$-$C_6$ alkyl group, a mono $C_1$-$C_6$alkylaminocarbonyl $C_1$-$C_6$ alkyl group, a di $C_1$-$C_6$alkylaminocarbonyl $C_1$-$C_6$alkyl group, a hydroxycarbonyl $C_1$-$C_6$ alkyl group or a $C_1$-$C_6$alkylsulfonyl group],

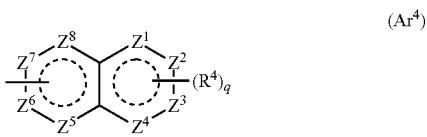
(Ar⁴)

[wherein,
$R^4$ and q are same as described in the above [2]; and
$Z^1$, $Z^2$, $Z^3$, $Z^4$, $Z^5$, $Z^6$, $Z^7$ and $Z^8$ are each independently N, C, CH, or $CR^4$ (1, 2, or 3 of $Z^1$ to $Z^8$ may represent a nitrogen atom)].

[4] The compound or the pharmaceutically acceptable salt thereof, as described in the above [3], wherein $Ar^1$, $Ar^2$, $Ar^3$, or $Ar^4$ is represented by the following general formula:

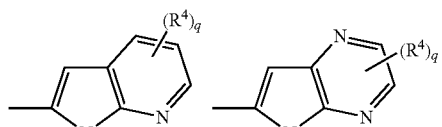

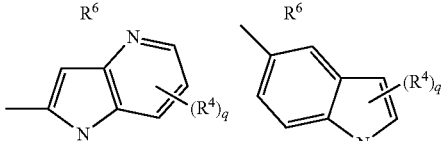

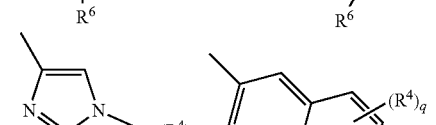

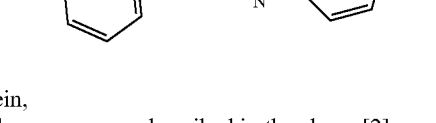

[wherein,
$R^4$ and q are same as described in the above [2];
$R^6$ is hydrogen or a $C_1$-$C_6$alkyl group; and
$(R^4)_q$ may substitute one of the two rings or both rings].

[5] The compound or the pharmaceutically acceptable salt thereof, as described in the above [2], wherein ring A is morpholine, piperidine, pyrrolidine, or azetidine which binds at N;
n is 1;
p is 0, 1, or 2; and
q is 0, 1, or 2.

[6] The compound or the pharmaceutically acceptable salt thereof, as described in the above [2], wherein the compound represented by general formula (I) is selected from the group consisting of 1-methyl-N-[2-(morpholin-4-yl)ethyl]-5-(quinolin-3-yl)-1H-pyrazole-3-carboxamide;

1-methyl-5-{5-methyl-1H-pyrrolo[3,2-b]pyridin-2-yl}-N-[2-(morpholin-4-yl)ethyl]-1H-pyrazole-3-carboxamide;

1-methyl-N-[2-(morpholin-4-yl)ethyl]-5-{1H-pyrrolo[2,3-b]pyridin-2-yl}-1H-pyrazole-3-carbox amide;

1-methyl-N-[2-(morpholin-4-yl)ethyl]-5-{7H-pyrrolo[2,3-d]pyrimidin-6-yl}-1H-pyrazole-3-carb oxamide;

1-methyl-N-[2-(morpholin-4-yl)ethyl]-5-[5-(trifluoromethyl)-1H-pyrrolo[3,2-b]pyridin-2-yl]-1H-pyrazole-3-carboxamide;

1-methyl-5-{5-methyl-1H-pyrrolo[2,3-b]pyridin-2-yl}-N-[2-(morpholin-4-yl)ethyl]-1H-pyrazole-3-carboxamide;

5-{5-fluoro-1H-pyrrolo[2,3-b]pyridin-2-yl}-1-methyl-N-[2-(morpholin-4-yl)ethyl]-1H-pyrazole-3-carboxamide;

5-{5-cyano-1H-pyrrolo[3,2-b]pyridin-2-yl}-1-methyl-N-[2-(morpholin-4-yl)ethyl]-1H-pyrazole-3-carboxamide;

5-{6-fluoro-1H-pyrrolo[3,2-b]pyridin-2-yl}-1-methyl-N-[2-(morpholin-4-yl)ethyl]-1H-pyrazole-3-carboxamide;

1-methyl-N-[2-(morpholin-4-yl)ethyl]5-{5H-pyrrolo[2,3-b]pirazin-6-yl}-1H-pyrazole-3-carboxamide;

5-{5-cyano-1H-pyrrolo[2,3-b]pyridin-2-yl}-1-methyl-N-[2-(morpholin-4-yl)ethyl]-1H-pyrazole-3-carboxamide;

5-{5-fluoro1-methyl-1H-pyrrolo[2,3-b]pyridin-2-yl}-1-methyl-N-[2-(morpholin-4-yl)ethyl]-1H-pyrazole-3-carboxamide;

N-[2-(3,3-difluoroazetidin-1-yl)ethyl]-5-(5-fluoro-1H-indol-2-yl)-1-methyl-1H-pyrazole-3-carboxamide;

N-[2-(azetidin-1-yl)ethyl]-5-(5-fluoro-1H-indol-2-yl)-1-methyl-1H-pyrazole-3-carboxamide;

1-methyl-5-(2-methyl-1H-indol-5-yl)-N-[2-(morpholin-4-yl)ethyl]-1H-pyrazole-3-carboxamide;

5-(1,2-dimethyl-1H-indol-5-yl)-1-methyl-N-[2-(morpholin-4-yl)ethyl]-1H-pyrazole-3-carboxamide;

5-[1-(2-methoxyethyl)-1H-indol-3-yl]-1-methyl-N-[2-(morpholin-4-yl)ethyl]-1H-pyrazole-3-carboxamide;

5-(4-acetamido-1H-indol-2-yl)-1-methyl-N-[2-(morpholin-4-yl)ethyl]-1H-pyrazole-3-carboxamide;

5-{imidazo[1,2-a]pyridin-2-yl}-1-methyl-N-[2-(morpholin-4-yl)ethyl]-1H-pyrazole-3-carboxamide;

5-{6-fluoroimidazo[1,2-a]pyridin-2-yl}-1-methyl-N-[2-(morpholin-4-yl)ethyl]-1H-pyrazole-3-carboxamide;

5-{7-fluoroimidazo[1,2-a]pyridin-2-yl}-1-methyl-N-[2-(morpholin-4-yl)ethyl]-1H-pyrazole-3-carboxamide;

5-{6-cyanoimidazo[1,2-a]pyridin-2-yl}-1-methyl-N-[2-(morpholin-4-yl)ethyl]-1H-pyrazole-3-carboxamide;

N-[2-(3,3-difluoroazetidin-1-yl)ethyl]-1-methyl-5-(quinolin-3-yl)-1H-pyrazole-3-carboxamide;

N-[2-(3,3-difluoroazetidin-1-yl)ethyl]-1-methyl-5-{1H-pyrrolo[2,3-b]pyridin-2-yl}-1H-pyrazole-3-carboxamide; and 5-{7-cyanoimidazo[1,2-a]pyridin-2-yl}-1-methyl-N-[2-(morpholin-4-yl)ethyl]-1H-pyrazole-3-carboxamide.

[7] An intermediate of the compound described in the above [2], which is represented by the general formula (1A):

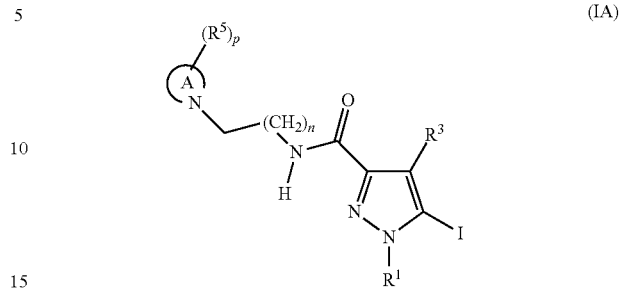

[wherein, each description is same as described in [2] above].

[8] An intermediate of the compound described in the above [2], which is represented by the general formula (1B):

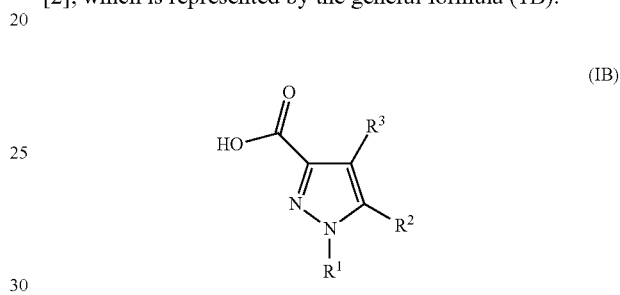

[wherein, $R^1$, $R^2$, $R^3$ are same as defined in formula (I), and OH of carboxylic acid may be replaced by a removable substituent].

[9] A preventive or therapeutic agent for diseases in which 5-$HT_{2B}$ receptors are involved wherein the compound or the pharmaceutically acceptable salt thereof, as described in any one of [2] to [6], is an effective ingredient.

[10] A pharmaceutical composition comprising the compound or the pharmaceutically acceptable salt thereof, as described in any one of [2] to [6], and a pharmaceutically acceptable carrier.

[11] A pharmaceutical composition for prevention or treatment of a disease condition mediated by 5-$HT_{2B}$ receptors, in a mammalian subject, comprising an effective amount of the compound or the pharmaceutically acceptable salt thereof as described in any one of [2] to [5], and a pharmaceutically acceptable carrier.

[12] A pharmaceutical composition comprising the compound as described in any one of [2] to [6], further comprising another pharmacologically active agent.

[13] The compound or the pharmaceutically acceptable salt thereof, as described in any one of [2] to [6], for use in prevention or treatment of a disease condition mediated by 5-$HT_{2B}$ receptors.

[14] A use of the compound or the pharmaceutically acceptable salt thereof, as described in any one of [2] to [6], for the manufacture of a medicament for prevention or treatment of a condition mediated by 5-$HT_{2B}$ receptors.

[15] A method of prevention or treatment for migraine, inflammatory pain, nociceptive pain, neuropathic pain, fibromyalgia, chronic low back pain, visceral pain, gastroesophageal reflux disease (GERD), constipation, diarrhea, functional gastrointestinal disorder, irritable bowel syndrome, asthma, osteoarthritis, rheumatoid arthritis, Crohn's disease, ulcerative colitis, glomerulonephritis, nephritis, dermatitis, hepatitis, vasculitis, renal ischemia, cerebral stroke, myocardial infarction, cerebral ischemia, Alzheimer's disease, reversible airway obstruction, adult respiratory disease syndrome, chronic obstructive pulmonary disease (COPD), pulmonary hypertension (PH), idiopathic interstitial pneumonia, bronchitis, liver fibrosis, cryptogenic fibrosing alveolitis, multiple sclerosis, depression, anxiety or obesity, which is characterized by administering an effective amount of a pharmaceutical composition, comprising the compound or the pharmaceutically acceptable salt thereof as described in any one of [2] to [6] and a pharmaceutically acceptable carrier, to human or a mammalian subject.

Advantageous Effects of Invention

The effective ingredient, pyrazol-3-carboxamide derivatives of this invention has novel nucleus and inhibits strongly and selectively function of $5\text{-}HT_{2B}$ receptor. Strong $5\text{-}HT_{2B}$ receptor antagonistic activity of this invention medicament shows therapeutic effects based on the excellent pharmaceutical effects. In addition, the high selectivity of this invention medicament is useful for reducing the wide range of side-effects based on the receptor activities other than $5\text{-}HT_{2B}$ receptor.

BRIEF DESCRIPTION OF DRAWINGS

FIG. 1 is a graph for results in colonic distension study using a TNBS induced rat IBS model about Example compound 24.

DESCRIPTION OF EMBODIMENTS

The compound of this invention is characterized by specific binding activities to $5\text{-}HT_{2B}$ receptor. The compound of this invention selectively inhibits the activities of $5\text{-}HT_{2B}$ receptor by binding antagonistically to $5\text{-}HT_{2B}$ receptor, which is useful for the treatment or the pretreatment in mammalian relating to the said receptor.

The term 'antagonistic agent' is also called antagonist, and means the medicament acts antagonistically against agonist and reduce the effects. The ability that these antagonists and agonists bind partially is called binding affinities, and the evaluation of binding affinities, as examples described below, is conducted by comparing Ki value calculated in the receptor binding studies in in vitro, or $IC_{50}$ values conducted in the receptor binding assay in the same condition in some cases. In the receptor binding studies, when $IC_{50}$ can not be calculated because of not showing the enough antagonistic activities, the $IC_{50}$ of the compound may be regarded as more than the said concentration.

The compound of this invention has a binding affinity, and $IC_{50}$ value, which shows the activity inhibiting serotonin to $5\text{-}HT_{2B}$ receptor (inhibitory activity), is preferably lower than 1000 nM, more preferably lower than 100 nM, further preferably lower than 10 nM, and the most preferably lower than 1 nM.

The compound of this invention or the pharmaceutically acceptable salt thereof is favorable to be 'selective' on the inhibitory activity to the $5\text{-}HT_{2B}$ comparing to the other receptors. 'Selective' means that the inhibitory activity to the said receptor is higher than inhibitory activities to 'the other receptors'. 'Selective' in the present invention means that $IC_{50}$ value of inhibitory activity to the said receptor is one-tenth or less, preferably one-hundredth or less, and more preferably one-thousandth or less, comparing to $IC_{50}$ value of 'the other receptors'.

'The other receptors' here means the other receptors reported in the existing non-selective serotonin antagonists. Particularly after evaluating the selectivities against $5\text{-}HT_{2A}$, $5\text{-}HT_{2C}$, evaluating the representative compounds on the influence to existing receptor and enzymes is favorable.

The inhibitory activities or receptor antagonistic activities of $5\text{-}HT_{2B}$ selective antagonists in this invention can be easily evaluated with the known technologies mentioned below.

In this context, the term "$C_1\text{-}C_6$" as defined in the above-mentioned general formula, unless otherwise indicated, means a straight or branched carbon chain having 1 to 6 carbon atoms. Thus, the "$C_1\text{-}C_6$ alkyl group" means an alkyl group having 1 to 6 carbon atoms, including preferably methyl (hereinafter occasionally abbreviated to as Me), ethyl (hereinafter occasionally abbreviated to as Et), propyl, isopropyl, butyl, isobutyl, tert-butyl.

The "halogen" means the 17 group of the periodic table, including preferably F, Cl, Br or I.

The "haloalkyl group" means $C_1\text{-}C_6$ alkyl group which is substituted with 1 to 5 halogen atom(s).

The "aryl ring" means mono- or bicyclic ring which may be saturated or partially or totally unsaturated. The aryl means a substituent which binds at the part leaked one hydrogen atom out from the aryl ring, including preferably $Ar^1$, $Ar^2$, $Ar^3$ and $Ar^4$.

An unsaturated monocyclic ring group contains, for example, phenyl, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isoxazolyl, isothiazolyl, triazolyl, furazanyl are cited.

An unsaturated bicyclic ring group contains, for example, naphthyl, benzofuranyl, isobenzofuranyl, benzothiophenyl, indolyl, isoindolyl, benzoxazolyl, benzothiazolyl, indazolyl, benzimidazolyl, quinolyl, isoquinolyl, cinnolinyl, phthalazinyl, quinazolinyl, quinoxalinyl are cited.

An example of saturated ring group contains the ring which is partially saturated or totally saturated in the unsaturated part of the mono- or bicyclic ring group described above.

'$R^{1A}$ may combine with the other $R^{1A}$' means that $NR^{1A}R^{1A}$ such as $NR^{1A}R^{1A}$, $CONR^{1A}R^{1A}$ and $SO_2NR^{1A}R^{1A}$ may show the 3 to 13 membered carbon-containing ring group by the said combination (e.g. r is 1 to 12 in the following scheme (IIa)).

Among them, the 3 to 8 membered carbon-containing ring group is favorable (e.g. r is 1 to 6 in the following scheme (IIa)). Actually $CONR^{1A}R^{1A}$ and $NR^{1A}R^{1A}$ in $R^4$ can be described in the following scheme (IIa). The binding style, however, the binding style is not limited only in the following scheme.

'$R^{1B}$ may combine with the other $R^{1B}$' is the same meaning as described above and $R^{1A}$ is replaced with $R^{1B}$.

The removable substituents are exemplified ethoxy, phenoxy, halogen, alkoxycarbonyloxy, aryloxycarbonyloxy, imidazol-1-yl, 4-nitrophenoxy group, but not limited only these.

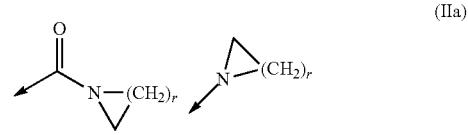

(IIa)

The salts of a compound of formula (I) are pharmaceutically acceptable salts and include the acid addition and base addition (including diacid salts and dibase salt) thereof.

In general, suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, hexafluorophosphate, hibenzate, hydrochloride, hydrobromide, hydroiodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples as base salts include the aluminium, arginine, benzathine, calcium, choline, diethylamine, diolamine, glycine, lysine, magnesium, meglumine, olamine, potassium, sodium, tromethamine and zinc salts. See Handbook of Pharmaceutical Salts: Properties, Selection, and Use by Stahl and Wermuth (Wiley-VCH, Weinheim, Germany, 2002), as needed.

Pharmaceutically acceptable salts of compounds of formula (I) can be easily prepared by mixing the solution of desired acid or base. The resulting salt may precipitate out and be collected by filtration or may be recovered by evaporation of the solvent. The degree of ionization in the resulting salt may vary from completely ionized to almost non-ionized.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Pharmaceutically acceptable solvates in accordance with the invention include those wherein the solvent of crystallization may be isotopically substituted, e.g. $D_2O$, $d_6$-acetone, $d_6$-dimethylsulfoxide.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. See J Pharm Sci, 64 (8), 1269-1288, by Haleblian (August 1975), as needed.

Hereinafter all references to compounds of formula (I) include references to salts, solvates and complexes thereof and to solvates and complexes of salts thereof.

The compounds of the invention include compounds of formula (I) as hereinbefore defined, including polymorphs and crystal habits thereof, prodrugs and isomers thereof (including optical, geometric and tautomeric isomers) as hereinafter defined and isotopically-labelled compounds of formula (I).

As indicated, so-called 'pro-drugs' of the compounds of formula (I) or their salts are also within the scope of the invention. Thus certain derivatives of compounds of formula I which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

Some examples of prodrugs in accordance with the invention include:

when the compound of formula (I) or its salt contains a carboxylic acid functionality (—COOH), an ester thereof and amide thereof, for example, ethyl ester thereof, phenyl ester thereof, carboxymethyl ester thereof, dimethylaminomethyl ester thereof, pivaloyloxymethyl ester thereof, ethoxycarbonyloxyethyl ester thereof, phthalidyl ester thereof, (5-methyl-2-oxo-1,3-dioxolen-4-yl)methyl ester thereof, 1-(cyclohexyloxycarbonyloxy)ethyl ester thereof, methylamide thereof) and the like;

when the compound of formula (I) or its salt contains an alcohol functionality (—OH), a compound wherein the hydroxy functionality is subject to acylation, alkylation, phosphorylation and boration, for example, an acetyl compound, a palmitoyl compound, a propanoyl compound, a pivaloyl compound, a succinyl compound, an alanyl compound, a dimethylaminomethylcarbonyl compound and the like; In addition, depending on the substituents, the prodrug may form the N-oxide. Also included within the scope of the invention are such N-oxides;

when the compound of formula (I) or its salt contains an amino functionality, an amide thereof, for example, a compound wherein, as the case may be, one or both hydrogens of the amino functionality is/are subject to acylation, alkylation and phosphorylation, for example, an eicosanoyl compound, alanyl compound, a pentylaminocarbonyl compound, a (5-methyl2-oxo-1,3-dioxolen-4-yl)methoxycarbonyl compound, a tetrahydrofuranyl compound, a pyrrolidinylmethyl compound, tert-butyl compound and the like.

Further examples of replacement groups in accordance with the foregoing examples and examples of other prodrug types may be found in the aforementioned references. Moreover, certain compounds of formula I may themselves act as prodrugs of other compounds of formula (I).

Compounds of formula (I) containing one or more asymmetric carbon atoms can exist as two or more stereoisomers. Where a compound of general formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of general formula (I), including compounds exhibiting more than equal two type of isomerism, and mixtures of one or more thereof. Also included are acid addition or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of general formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50 (w/w) % isopropanol, typically from 2 to 20 (w/w) %, and from 0 to 5 (w/w) % of an alkylamine, typically 0.1 (w/w) % diethylamine. Concentration of the eluate affords the enriched mixture.

Stereoisomeric conglomerates may be separated by conventional techniques known to those skilled in the art—see, for example, Stereochemistry of Organic Compounds by E L Eliel (Wiley, New York, 1994).

The present invention includes all pharmaceutically acceptable isotopically-labelled compounds of general formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Substitution with heavier isotopes such as deuterium, i.e. $^2H$, may afford certain therapeutic advantages resulting from greater metabolic stability, for example, increased in vivo half-life or reduced dosage requirements, and hence may be preferred rather than $^1H$ normal compound in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

All of the compounds of the general formula (I) can be prepared by the procedures described in the general methods presented below or by the specific methods described in the Examples section and the Preparations section, or by routine modifications thereof. The present invention also encompasses any one or more of these processes for preparing the compounds of general formula (I), in addition to any novel intermediates used therein.

The compound of the general formula (I) in this invention can be prepared with known preparation method or can be prepared according to the general procedure or preparation method shown in the following reaction scheme. Unless otherwise indicated, $R^1$ to $R^5$ and X, Y and Z in the following methods are as defined above. The term "protecting group", as used hereinafter, means a hydroxyl- or amino-protecting group which is selected from typical hydroxy, acetylene or amino-protecting groups described in Protective Groups in Organic Synthesis edited by T. W. Greene et al., (John Wiley & Sons, 1999). Moreover, each compound described in the reaction scheme, unless it inhibits the reaction, may form the salt which includes the same salt as compound (I). The prodrug of this invention can be prepared by introducing the specific group at the stage of the intermediate or by the reaction using an obtained compound, which is similar to the protecting group described above. The reaction such as esterification, amidation and dehydration can be accomplished using standard methods well known to those skilled in the art.

The preparation of parenteral formulations under sterile conditions, for example, by lyophilization, may readily be accomplished using standard pharmaceutical techniques well known to those skilled in the art.

The preparation of the compound in formula $I^4$ from formula II through process A-2 (Method 1) and the preparation of the compound in formula $I^4$ from formula II through process A-3 (Method 2) are shown as follows.

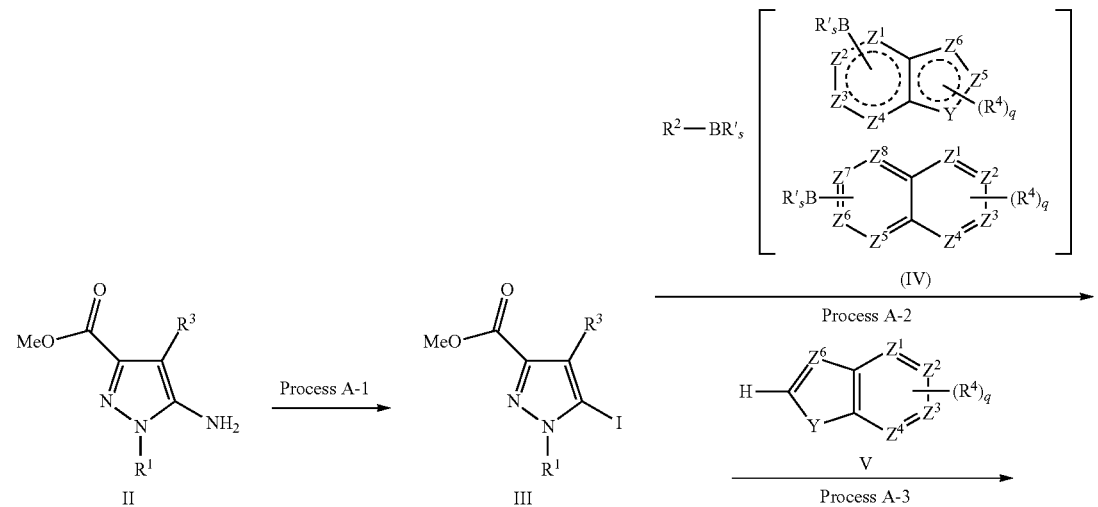

-continued

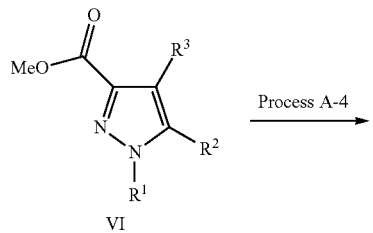
VI

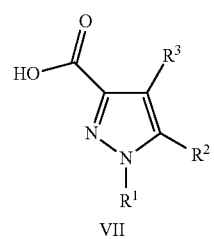
VII

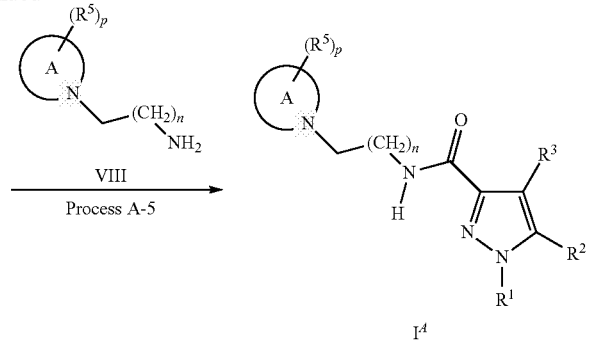
I⁴

In a representation of R'ₛB, R' means OH, O-lower alkyl, lower alkyl or fluorine, and s is 2 or 3, B is boron atom. As the concrete representation of substituent, $(OH)_2B$, (O-lower alkyl)$_2$B, (lower alkyl)$_2$B, potassium trifluoroborate $(BF_3^-)$ $(BF_3K)$ are described, but when (O-lower alkyl)$_2$B may form the cyclic ring between the lower alkyl groups.

Process A-1

In this step, iodo-compounds of equation III can be prepared with one pot synthesis in the presence of the appropriate iodination agents through diazonium salts, or after formation of diazonium salts they can be prepared by adding the appropriate iodination agents. The formation of diazonium salts can be conducted in the known procedure. In the typical procedure, diazonium formation is conducted by using sodium nitrite under acid solution. In acid solution, for example, acetic acid, hydrochloric acid, formic acid or sulfuric acid solution can be used, wherein acetic acid is preferable. The reaction is 10 minutes to 12 hours, but in general, 30 minutes to 6 hours. The reaction temperature is ranged about −20° C. to 30° C., but in general, −10° C. to 5° C. An appropriate iodination agent, potassium iodide, sodium iodide, or iodide, wherein potassium iodide is preferable. In the reaction scheme, Me means methyl group (same hereafter).

Process A-2

In this step, compound (VI) can be prepared using an aryl cross-coupling reaction with compound (III) prepared in process A-1. It can be prepared under the coupling condition in the presence of an appropriate transition metal catalyst and base (or without base) in a mixture of water-organic solvent. As an appropriate R'ₛB substituent in an arylmetallic reagent, for example, $(OH)_2B$, (O-lower alkyl)$_2$B, (lower alkyl)$_2$B, potassium salt$(BF_3K)$ of trifluoroborate$(BF_3^-)$ are cited, but in the case of (O-lower alkyl)$_2$B, a cyclic ring may be formed between lower alkyl groups.

As a transition metal catalyst, for example, tetrakis(triphenylphosphine)palladium, bis(triphenylphosphine)palladium(II)chloride, copper(0), copper(I) acetate, copper(I) bromide, copper(I) chloride, copper(I) iodide, Copper(I) oxide, copper(I) trifluoromethane sulfonate, copper(II) acetate, copper(II) bromide, copper(II) chloride, copper(II) iodide, Copper(II) oxide, copper(II)trifluoromethane sulfonate(II), palladium acetate(II), palladium(II) chloride, bis(acetonitril) dichloropalladium (II), bis(dibenzylideneacetone)palladium (0), tris(dibenzylideneacetone)dipalladium (0), [1,1'-bis (diphenylphosphino)ferrocene]palladium(II)dichloride and so on are cited. In particular, tetrakis(triphenylphosphine) palladium, bis(triphenylphosphine) palladium (II)chloride, palladium acetate (II), bis(acetonitril)dichloropalladium(II), tris(dibenzylideneacetone)dipalladium(0), [1,1'-bis(diphenylphosphino)ferrocene]palladium(II) dichloride are favorable. As an arylmetallic reagent, for example, boronic acid reagents such as 2-indoylboronic acid derivative and boronic acid ester reagents such as 2-indoylboronic acid ester derivative are cited but not limited to them. As an appropriate organic solvent in water-organic mixed solution, for example, in the presence or absence of water soluble base such as potassium hydroxide, sodium hydroxide, lithium hydroxide and potassium carbonate solution, tetrahydrofuran, 1,4-dioxane, N,N-dimethylformamide (DMF), acetonitril, alcohols such as methanol and ethanol, halogenated hydrocarbons such as dichloromethane, 1,2-dichloroethane, chloroform, carbon tetrachloride; or diethylether are cited. This reaction can be conducted in the presence of appropriate additional factors. As such an additional factor, for example, triphenylphosphine, tri-tert-butylphosphine, 1,1'-bis(diphenylphosphino)ferrocene, tri-2-furylphosphine, 2-(dichlorohexylphosphino)biphenyl, triphenylarsine, tetrabutylammonium chloride, tetrabutylammonium fluoride, acetic acidlithium, lithium chloride, triethylamine, potassium (or sodium) methoxide, sodium hydroxide, sodium carbonate, potassium phosphate, cesium carbonate, sodium bicarbonate, or sodium iodide are cited. This reaction is about 0° C. to 200° C., and is generally about 20° C. to 120° C. The reaction period is about 5 minutes to 96 hours, and is generally about 30 minutes to 24 hours. Further, during the reaction, a microwave reactor can be used. In addition, when Y is NH, the nitrogen atom can be protected with a lower alkoxycarbonyl group (e.g. Boc group) and (p-alkyl)benzenesulfonyl group (e.g. benzenesulfonyl and p-toluenesulfonyl group).

Other than a Suzuki-Miyaura cross coupling shown above, Stillecross coupling reaction using trialkyltin instead of R'ₛB substituent, and Negishi coupling reaction zinc-halogen, wherein as a halogen, chlorine, bromine, iodine are cited, instead of R'ₛB substituent can be used.

Process A-3

In this step, the heterocyclic compound (VI) corresponding to general formula $R^2$ can be prepared by derivatizing to the aryl boronate ester using C—H borylation reaction between pinacol borane (HBpin) or bis(pinacolate)diborane $(B_2pin_2, pin=Me_4C_2O_2)$ and the heterocyclic compound (V) under an appropriate transition metal catalyst (e.g. iridium) and an appropriate organic solvent. (C—H borylation; T. Ishiyama et al., Organic Synthesis (2005), 82, 126-133.) The coupling compound (VI) can be prepared by Suzuki-Miyaura reaction of the derivatized aryl boronate ester with the compound (III). These reactions can be conducted in the one pot reaction or two steps reaction procedure.

As a transition metal catalyst, for example, [Ir(OMe) (COD)]$_2$(COD means 1,5-cyclooctadiene), Cp*Rh(η⁴-

C₆Me₆)(Cp* means C₅Me₅), Ir(η⁵-C₉H₇)(COD), [IrCl(COD)]₂, [IrCl(COE)₂]₂, or, RhCl{P(i-Pr)₃}(N₂) are cited. As an additive, for example, 1,2-bis(dimethylphosphino)ethane(dmpe), 2,2'-bipyridin-(dpy), 4,4'-ditertbutyl-2,2'-bipyridin-(dtbpy), or dppe are cited. As an appropriate organic solvent, for example, hydrocarbons such as n-hexane, or cyclohexane are cited. Using an combination of ½[IrCl(COD)]₂ and 4,4'-ditertbutyl-2,2'-bipyridin-(dtbpy) as a catalyst in hexane, reacting pinacolborane or bis(pinacolate)diborane with the aryl compound is an practical preparation. Then, reacting aryl boronate esters prepared above with the compound (III) is transferred to the compound (VI) by Suzuki-Miyaura reaction. This reaction is substantially same as that in the process A-2. The same reagents and reaction conditions in the process A-2 can be used, which is similar to the process A-2 described above. Proviso when this reaction is conducted in one pot reaction in Suzuki-Miyaura reaction, the combination of N,N-dimethylformamide(DMF) or 1,4-dioxane as a solvent, solid potassium phosphate (K₃PO₄) as a base, [1,1'-bis(diphenylphosphino)ferrocene]palladium(II)dichloride (PdCl₂(dppf)) as a palladium catalyst is favorable.

C—H borylation described above, followed by introduction reaction of the direct bicyclic heteroaryl group(V), which is similar to Suzuki-Miyaura reaction, can be replaced with the direct arylation reaction mediated by palladium (non-patent literature 10), rhodium (non-patent literature 11) and copper (non-patent literature 12).

Non-patent Literature 11: Aldrichimica Acta Vol. 40, No. 2-(2007) 35-41.

Non-patent Literature 12: Tetrahedron Letter 49 (2008) 1598-1600.

Process A-4

In this step, the carboxylic acid compound (VII) can be prepared by the hydrolysis of the ester compound (VI) in a reaction solvent.

The hydrolysis can be conducted according to the procedure known in public. In the typical procedure, the hydrolysis can be conducted under basic condition such as sodium hydroxide, potassium hydroxide or lithium hydroxide. As an appropriate solvent, for example, alcohols such as methanol, ethanol, propanol, butanol, 2-methoxymethanol, or ethylene glycol; ethers such as tetrahydrofuran (THF), 1,2-dimethoxyethane(DME), or 1,4-dioxane; amides such as N,N-dimethylformamide (DMF) or hexamethylphosphoric triamide; sulfoxides such as dimethylsulfoxide (DMSO), or water are cited. The reaction period is about 30 minutes to 48 hours, and is generally about 60 minutes to 30 hours. The reaction temperature is about −20° C. to 100° C., and is generally about 20° C. to 75° C.

The hydrolysis can be conducted under acidic condition, for example, hydrogen halide such as hydrochloride or hydrobromide; sulfonic acids such as p-toluenesulfonic acid or benzenesulfonic acid; p-toluenesulfonic acid pyridium; and carboxylic acids such as acetic acid or trifluoroacetic acid. As an appropriate solvent, for example, alcohols such as methanol, ethanol, propanol, butanol, 2-methoxymethanol, or ethylene glycol; ethers such as tetrahydrofuran (THF), 1,2-dimethoxyethane (DME), or 1,4-dioxane; or halogenated hydrocarbon such as 1,2-dichloroethane; or amides such as N,N-dimethylformamide (DMF) or hexamethylphosphoric triamide; sulfoxides such as dimethylsulfoxide (DMSO), or water are cited. The reaction period is about 30 minutes to 24 hours, and is generally about 60 minutes to 10 hours. The reaction temperature is about −20° C. to 100° C., and is generally about 0° C. to 65° C.

Process A-5

In this step, the amide compound (I⁴) can be prepared in the presence or absence of a coupling reagent in an inert solvent by coupling reaction of the amine compound (VIII) with a carboxylic acid compound (VII) in a reaction solvent. In addition, this reaction can be conducted in the presence or absence of additives such as 1-hydroxybenzotriazole (HOBt) or 1-hydroxyazabenzotriazole. As an appropriate solvent, for example, acetone, nitromethane, N,N-dimethylformamide (DMF), sulfolane, dimethylsulfoxide (DMSO), 1-methyl-2-pyrrolidinone (NMP), 2-butanone, acetonitril; halogenated hydrocarbons such as dichloromethane, 1,2-dichloroethane, chloroform; ethers such as tetrahydrofuran and 1,4-dioxane are cited. The reaction period is about 5 minutes to 1 week, and is generally about 30 minutes to 24 hours. The reaction temperature is about −20° C. to 100° C., and is generally about 0° C. to 60° C. As an appropriate coupling agent, the agent which is used in the peptide synthesis can be used, for example, dicyclohexylcarbodiimide (DCC), water soluble carbodiimide (WSC), hexafluorophosphate-O-benzotriazol-1-yl-N,N,N',N'-tetramethyluronium (HBTU), 2-ethoxy-N-ethoxycarbonyl-1,2-dihydroquinoline, tetrafluoro boric acid 2-bromo-1-ethylpyridinium (BEP), 2-chloro-1,3-dimethylimidazolinium chloride, benzotriazol-1-yloxytris(dimethylamino)phosphonium hexafluorophosphate (BOP), diethyl azodicarboxylate-triphenylphosphine, diethyl cyanophosphate, diethylphosphorylazide, 2-chloro1-methylpyridinium iodide, N,N'-carbonyldiimidazol, benzotriazol-1-yl-diethylphosphate, ethyl chloroformate or isobutyl chloroformate are cited. In addition, it is desirable to conduct the reaction in the presence of bases such as N,N-diisopropylethylamine, N-methylmorpholine, 4-(dimethylamino)pyridine or triethylamine. The amide compound (I⁴) can be prepared through the corresponding acyl halide which is obtained by the reaction with halogenating agent such as oxalyl chloride, phosphorus oxychloride, or thionyl chloride. The obtained acyl halide can be converted to the corresponding amide compound (I⁴) by treating the amine compound (VIII) without using condensation reagents described in this step.

The synthesis of azaindole ring (method 3) using ring formation reaction in the process B-6 is shown as follows.

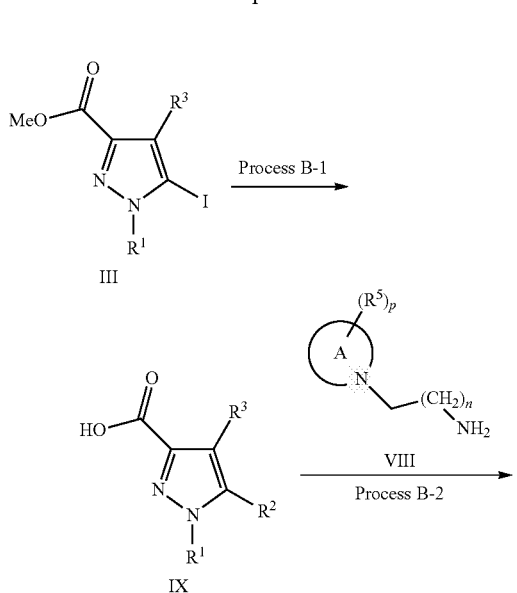

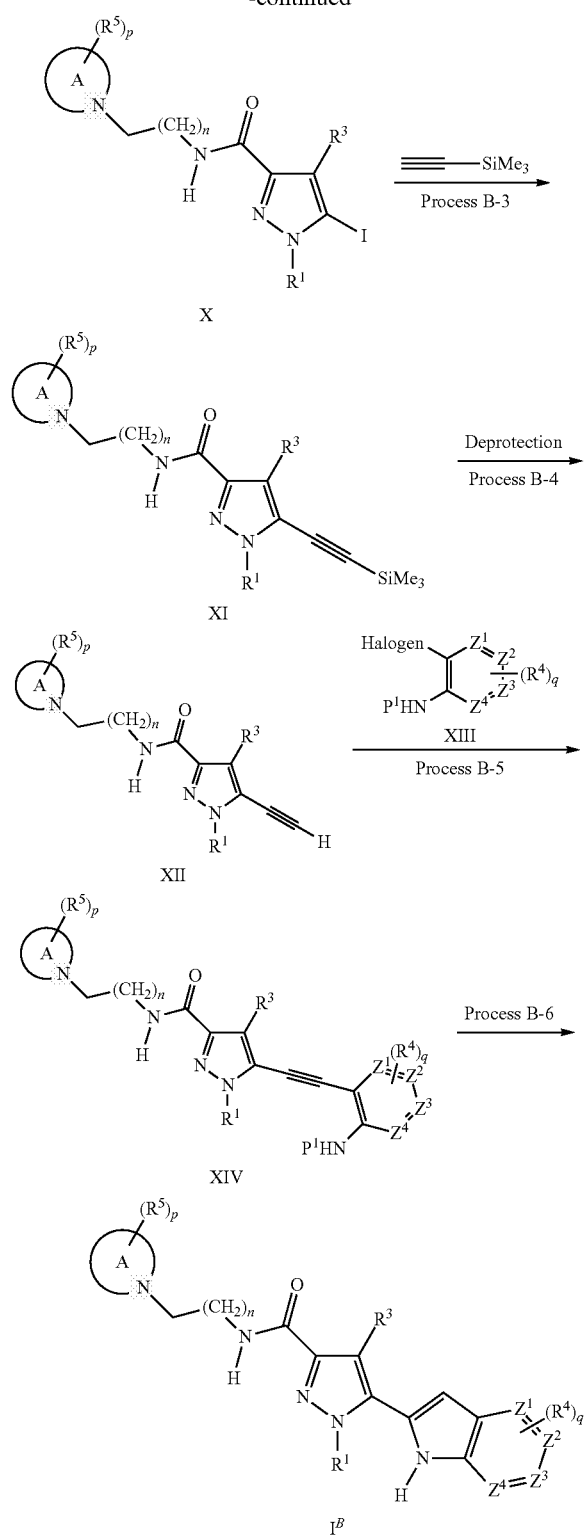

Process B-1

In this step, the compound of IX can be prepared by the hydrolysis of ester compounds (III). This reaction is substantially same as that in the process A-4 and the same reagents and reaction conditions in the process A-4 can be used in the similar way of the process A-4.

Process B-2

In this step, the compound of X can be prepared by the amidation reaction of carboxylic acid compound (IX) with amine compound (VIII). This reaction is substantially same as that in the process A-5 and the same reagents and reaction conditions in the process A-5 can be used in the similar way of the process A-5.

Process B-3

In this step, the compound (XI) can be prepared by using doss-coupling reaction of the compound (X) with an acetylene compound protected by trialkylsilyl group such as trimethylsilyl group in the presence of a catalytic amount of palladium reagent and a copper (I) salt or palladium reagent and a phosphine ligand in an appropriate solvent including a base or using only a base itself as a solvent. As an example of palladium reagent, tetrakis(triphenylphosphine)palladium and bis(triphenylphosphine)palladium (II) chloride are preferably cited. As an example of copper(I) salt, copper(I) iodide and copper(I) bromide are preferably cited. As a phosphine ligand, for example, bis(diphenylphosphino)butane (DPPB) is cited. As an example of base, for example, diethylamine, triethylamine, diisopropylethylamine, dicyclohexylamine, potassium carbonate and sodium carbonate are cited. In addition, as a reaction solvent, for example, tetrahydrofuran, 1,4-dioxane, N,N-dimethylformamide (DMF), acetonitril, ethyl acetate, hydrocarbons such as n-hexane, cyclohexane, benzene, toluene, and diethylether are cited. The reaction period is about 5 minutes to 96 hours, and is generally about 30 minutes to 24 hours. The reaction temperature is about −78° C. to 200° C., and is generally about −20° C. to 80° C. Further, during the reaction, a microwave reactor can be used.

Process B-4

In this step, the compound (XII) can be prepared by deprotecting trialkylsilyl group using a usual method known in general such as method described in John wiley & Sons, Protecting Groups in Organic Synthesis (1999). As a usual method, the deprotection can be conducted in the presence of a base such as potassium carbonate and sodium carbonate in an alcohol solvent such as methyl alcohol and ethyl alcohol.

Process B-5

This reaction is substantially same as that in the process B-3 and the compound (XIV) can be prepared by Sonogashira-coupling reaction of acetylene compound (XII) and arylhalide compound (XIII), wherein the scheme $P^1$ is hydrogen, tert-buthoxycarbonyl group or amino-protecting group such as trifluoroacetyl group, using the same reagents and reaction conditions in the process B-3 can be used in the similar way of the process B-3.

Process B-6

In this step, the compound ($I^B$) can be prepared by the intramolecular cycloaddition reaction of the acetylene compound (XIV) using an appropriate base. As an appropriate base, potassium tert-buthoxide, sodium tert-buthoxide, cesium tert-buthoxide, cesium hydroxide, 1,8-diazabicyclo[5.4.0]undeca-7-ene (DBU), 1,1,3,3-tetramethylguanidine, triethylamine and so on are used and the reaction is conducted in an appropriate solvent. As an appropriate solvent, N,N-dimethylformamide(DMF), N-methylpyrrolidinone (NMP), toluene, 1,4-dioxane, alcohols such as methanol and ethanol. The reaction period is about 5 minutes to 96 hours, and is generally about 30 minutes to 24 hours. The reaction temperature is about −78° C. to 250° C., and is generally -20° C. to 150° C. Preferably, it is conducted using potassium tert-buthoxide in DMF at the range of the room temperature to 80° C. In another method of the intramolecular cycloaddition can be conducted using a palladium catalyst wherein dichlorobis(triphenylphosphine)palladium (II), copper(I) iodide, triethylamine, DMF is cited as a representative combination. In addition, a metal catalyst or metal complexes including copper, gold, iridium, mercury, molybdenum, platinum and rhodium can be conducted. Further, when NHP$^1$ substituent is phenol or thiol group, the intramolecular cycloaddition can be conducted under conditions described above, resulting in the preparation of corresponding benzothiophene and benzofuran derivatives. Furthermore, after the cyclization reaction, when the protecting group (P$^1$) remains, the deprotection can be conducted by an appropriate condition.

The synthesis of imidazo[1,2-a]pyridine ring (method 4) using ring formation reaction in the process C-3 is shown as follows.

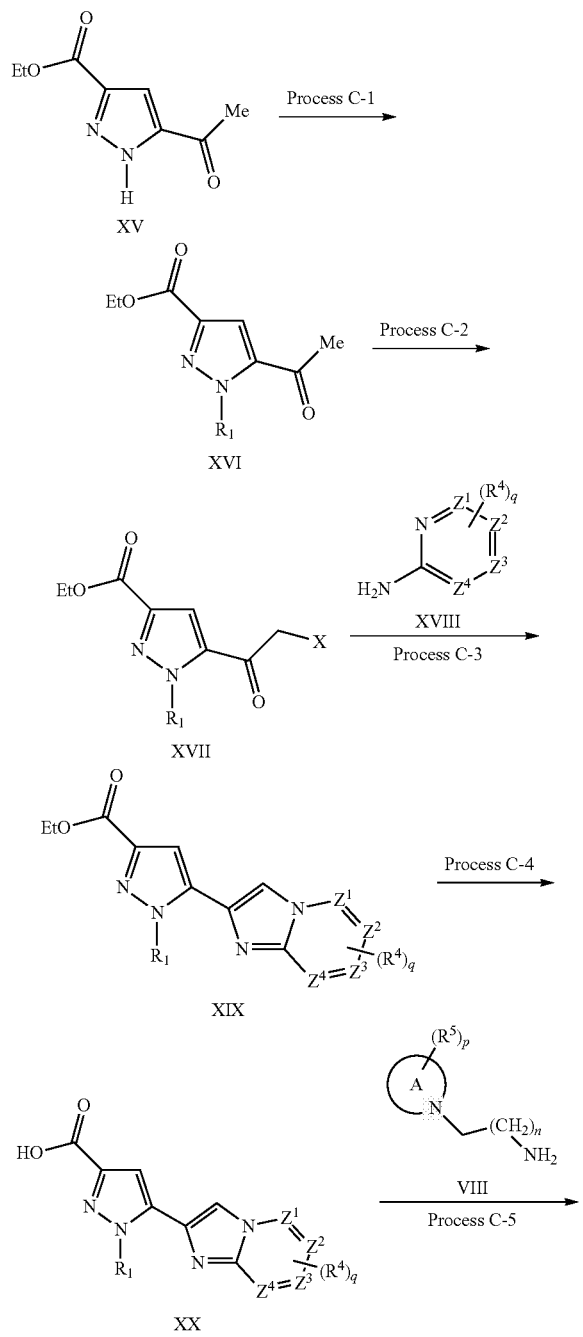

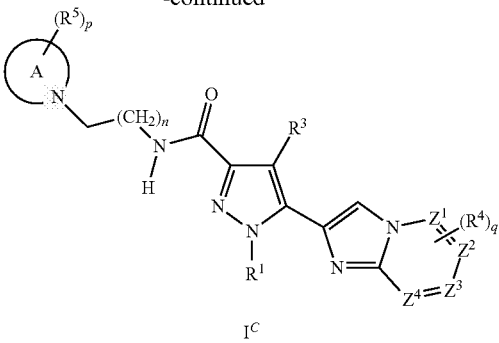

Process C-1

In this step, the compound of XVI can be prepared by N-alkylation reaction of compound XV which can be easily prepared by using an appropriate base and alkyl halide according to the literature. As an appropriate base, for example, sodium ethoxide, potassium tert-buthoxide, potassium hydride, sodium hydride, sodium bis(trimethylsilyl)amide, potassium carbonate, sodium carbonate, cesium carbonate, sodium hydroxide are cited but not limited to them. In addition as an appropriate organic solvent, for example, tetrahydrofuran, N,N-dimethylformamide (DMF), diethylether, acetonitril are cited. The reaction period is about 5 minutes to 96 hours, and is generally about 30 minutes to 24 hours. The reaction temperature is about −78° C. to 250° C., and is generally about −20° C. to 150° C.

Process C-2

In this step, the compound of XVII can be prepared by the alpha-halogenation reaction (X=Cl, Br, I) of compound (XVI) using an appropriate halogenation reagent. As an appropriate halogenation reagent, for example, bromine, chlorine, sulfuryl chloride, hydrogen bromide, N-bromosuccinimide (NBS), 5,5-dibromo-2,2-dimethyl-4,6-dioxo-1,3-dioxane, phenyl trimethylammonium tribromide are cited. As an appropriate organic solvent, for example, acetic acid, carbon bisulfide, ether, tetrahydrofuran, N,N-dimethylformamide(DMF), halogenated hydrocarbon such as dichloromethane, 1,2-dichloroethane, chloroform, carbon tetrachloride can be used. The reaction period is about 5 minutes to 96 hours, and is generally about 30 minutes to 24 hours. The reaction temperature is about −78° C. to 250° C., and is generally about −20° C. to 150° C.

Process C-3

In this step, the compound of XIX can be prepared by the ring condensation reaction of the alpha-haloketone compound (XVII) with an appropriate amine compound in the presence of an appropriate solvent with heat. As an appropriate solvent, for example, tetrahydrofuran, 1,4-dioxane, N,N-dimethylformamide (DMF), acetonitril, alcohols such as methanol and ethanol. The reaction period is about 5 minutes to 96 hours, and is generally about 30 minutes to 24 hours. The reaction temperature is about 0° C. to 250° C., and is generally about 30° C. to 150° C.

Process C-4

In this step, the compound of XX can be prepared by the hydrolysis of the ester compound (XIX). This reaction is substantially same as that in the process A-4 and the same reagents and reaction conditions in the process A-4 can be used in the similar way of the process A-4.

Process C-5

In this step, the compound of I$^C$ can be prepared by the amidation reaction of the carboxylic acid compound (XX)

with an amine compound (VIII). This reaction is substantially same as that in the process A-5 and the same reagents and reaction conditions in the process A-5 can be used in the similar way of the process A-5.

The changing amine side chain (method 5) using the process D-3 is shown as follows.

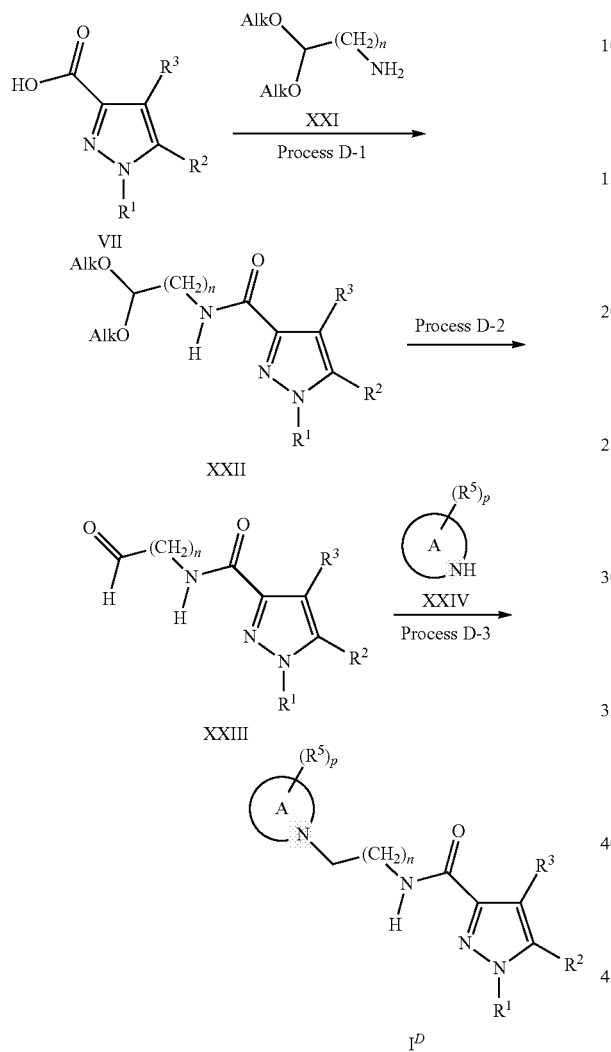

Process D-1

In this step, the compound of XXII can be prepared by the amidation reaction of the carboxylic acid compound (VII) with an amine compound (XXI). This reaction is substantially same as that in the process A-5 and the same reagents and reaction conditions in the process A-5 can be used in the similar way of the process A-5.

Process D-2

In this step, the compound (XXIII) can be prepared by deprotecting acetal group using a usual method known in general such as method described in John Wiley & Sons, Protecting Groups in Organic Synthesis (1999). As a usual method, the deprotection can be conducted in the presence of an acid such as dilute hydrochloric acid, p-toluenesulfonic acid or under an acid condition in a general organic solvent.

Process D-3

In this step, the compound ($I^D$) can be prepared by the reductive amination reaction of the aldehyde compound (XXIII) with an amine compound XXIV using an appropriate reducing agent. As an appropriate reducing agent, for example, sodium borohydride ($NaBH_4$), sodium cyanoborohydride ($NaBH_3CN$), sodium triacetoxyborohydride [$NaBH(OAc)_3$] are cited. As an appropriate solvent, for example, acetic acid, tetrahydrofuran, halogenated hydrocarbons such as dichloromethane, 1,2-dichloroethane, chloroform, carbon tetrachloride are used, and if its needed, a catalytic amount of acetic acid or Lewis acids such as titanium tetrachloride, tetraisopropoxy titanium[$Ti(O-iPr)_4$] can be used. When cyanoborohydride ($NaBH_3CN$) is used, the reaction can be also conducted under an acid condition. The reaction period is about 5 minutes to 96 hours, and is generally about 30 minutes to 24 hours. The reaction temperature is about 0° C. to 250° C., and is generally about 30° C. to 100° C.

The changing amine side chain (method 6) using the process E is shown as follows.

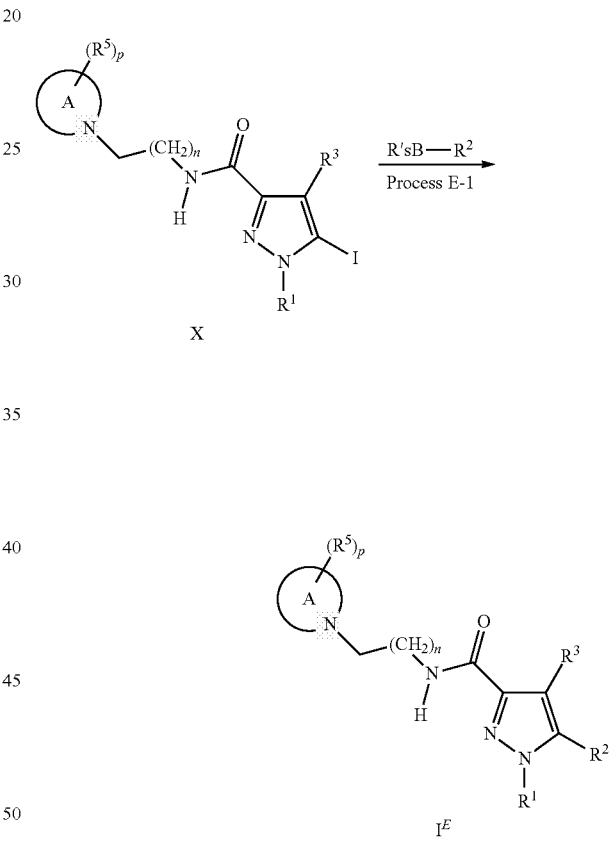

Process E-1

In this step, the compound of $I^E$ can be prepared by the coupling reaction of the halogenated compound (X) with an arylboronic acid (or ester) derivative. This reaction is substantially same as that in the process A-2 and the same reagents and reaction conditions in the process A-2 can be used in the similar way of the process A-2.

The changing $R^2$ side chain (method 7) using the process F is shown as follows. In the following XXVI, $P^2$ means the protecting group selected from lower alkoxycarbonyl group, benzyloxycarbonyl group, benzenesulfonyl and 4-alkylbenzenesulfonyl group.

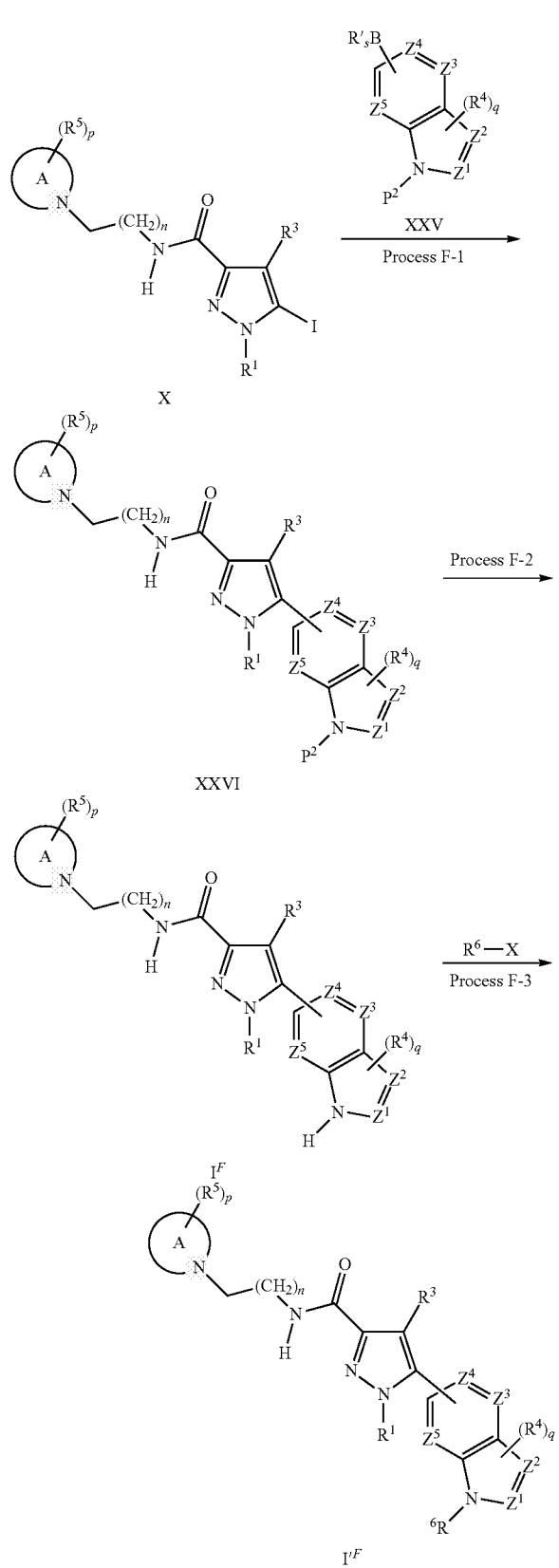

heteroarylboronic acid (or ester)) XXV which may be protected with tert-buthoxycarbonyl group or benzenesulfonyl or 4-alkylbenzenesulfonyl group. This reaction is substantially same as that in the process A-2 and the same reagents and reaction conditions in the process A-2 can be used in the similar way of the process A-2.

Process F-2

In this step, the compound ($I^F$) can be prepared by deprotecting trialkylsilyl group and arylsulfonyl group using a usual method known in general such as method described in John Wiley & Sons, Protecting Groups in Organic Synthesis (1999). As a usual method, the deprotection of tert-buthoxycarbonyl group can be conducted in the presence of an acid catalyst such as dilute hydrochloric acid, p-toluenesulfonic acid under acid conditions in a general organic solvent. The deprotection of benzenesulfonyl or 4-alkylbenzenesulfonyl groups can be deprotected in the presence of alkaline reagent such as potassium carbonate, sodium carbonate, cesium carbonate and sodium hydroxide in the combination of a general organic solvent.

Process F-3

In this step, the compound ($I'^F$) can be prepared by converting N—H bond on the heteroaryl ring in $I^F$ to N—$R^6$ bond. When $R^6$—X reagent is alkylhalide, this reaction is substantially same as that in the process C-1 and the reaction can be conducted under the same condition as the process C-1. In addition, O-tosylate, O-mesylate and O-triflate which have leaving group at hydroxyl group (—OH) can be substitutable. Further, when $R^6$ is alkylsulfonyl group, the reaction is substantially same as that in the process C-1 wherein alkylsulfonyl chloride is used under the same condition as the process C-1.

The intermediate (1A) is useful for the preparation of the compound of this invention. For example, the intermediate X shown in process B in the general synthesis is effectively used for the preparation of the compound of this invention.

The intermediate (IB) is useful for the preparation of the compound of this invention. For example, the intermediate VI and VII in the process A, XIX and XX in the synthetic process C, XXI in the synthetic process D in the general synthesis is effectively used for the preparation of the compound of this invention.

The pharmacological effects of the compounds of this invention as a 5-$HT_{2B}$ antagonist can be estimated by measuring the improvement of increasing pulmonary blood pressure in animal (rat, mouse) model exposed to chronic hypoxia. The existing drug for pulmonary arterial hypertension (e.g. sildenafil and prostaglandin preparations) and RS-127445 which is known as a 5-$HT_{2B}$ selective antagonist can be used for reference compounds.

The other pharmacological effects of the compounds of this invention as a 5-$HT_{2B}$ antagonist can be estimated by measuring the antidiarrheal effects in animal (rat, mouse) model exposed to drugs or stress. The existing antidiarrheal drug (e.g. loperamide and berberine) and RS-127445 which is known as 5-$HT_{2B}$ selective antagonist can be used for reference compounds.

Thus resulting compounds may be isolated and purified in a free form or as a salt by conventional salt-forming treatment. Isolation and purification may be achieved by applying a conventional chemical procedure such as extraction, concentration, distillation, crystallization, filtration, recrystallization, a variety of chromatography, and so on.

A variety of isomers can be isolated by a conventional way utilizing difference of the physicochemical properties between the isomers. For example, the optical isomers may be separated and purified by formation of diastereomeric salts Process F-1

In this step, the compound of XXVI can be prepared by the coupling reaction of the halogenated compound (X) with the from the racemates with an optically active organic acid (e.g., tartaric acid) and subsequent fractional recrystallization, or by column chromatography using a chiral stationary phase. In addition, the optically active compounds can be produced using a suitable optically active compound as a starting material. In this connection, a mixture of diastereomers may also be separated by fractional crystallization or chromatography to the corresponding pure enantiomer(s).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as, for example, tablets, capsules containing particulates, liquids, or powders, lozenges (including liquid-filled), chews, multi-particulates, nano-particulates, gels, solid solution, liposome, films (including muco-adhesive), ovules, sprays and liquid formulations.

Liquid formulations include, for example, suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by reconstituting a solid, for example, from a sachet in water and the like.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from about 1 wt % to about 80 wt % of the dosage form, more typically from about 5 wt % to about 60 wt % of the dosage form.

In addition to the drug as an active ingredient, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from about 1 wt % to about 25 wt %, preferably from about 5 wt % to about 20 wt % of the dosage form.

Binders are generally used to impart cohesive qualities to a tablet formulation. A tablet formulation may contain binders to impart cohesive qualities other than the drug as an active ingredient. Suitable binders include microcrystalline cellulose, gelatin, lactose (monohydrate, spray-dried monohydrate, anhydrous and the like), mannitol, xylitol, dextrose, sucrose, sorbitol, polyethylene glycol, natural and synthetic gums, polyvinylpyrrolidone, pregelatinized starch, hydroxypropyl cellulose and hydroxypropyl cellulose, dibasic calcium phosphate dehydrate and hydroxypropylmethylcellulose, and the like.

Tablets may also optionally comprise surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from about 0.25 wt % to about 10 wt %, preferably from about 0.5 wt % to about 3 wt % of the tablet.

Other possible ingredients include anti-oxidants, colorants, flavoring agents, preservatives, taste-masking agents and the like.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

The methods of preparing tablets are not limited, but general methods for preparing tablets can be appropriately used. For example, tablet blends may be compressed directly or by roller to form tablets. Tablet blends or portions of blends may alternatively be wet-, dry-, or melt-granulated, melt congealed, or extruded before tableting. The final formulation may comprise one or more layers and may be coated or uncoated; it may even be encapsulated.

In terms of the formulation of tablets, the contents described in "Pharmaceutical Dosage Forms Tablets, Vol. 1", by H. Lieberman and L. Lachman, Marcel Dekker, N.Y., 1980 (ISBN 0-8247-6918-X) can be referred.

Solid formulations for oral administration may be formulated to be immediate and/or modified release. Modified release formulations include, for example, delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations may contain excipients such as salts, carbohydrates and buffering agents (preferably to a pH of from about 3 to about 9). They may be typically aqueous solutions, but for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include, for example, delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include, for example, gels, hydrogels, lotions, solutions, creams, ointments, dusting powders, dressings, foams, films, skin patches, wafers, implants, sponges, fibers, bandages and microemulsions. Liposomes may also be used. Typical carriers include, for example, alcohol, water, mineral oil, liquid petrolatum, white petrolatum, glycerin, polyethylene glycol and propylene glycol or water and the like. Penetration enhancers may be incorporated—see, for example, J Pharm Sci, 88 (10), 955-958 by Finnin and Morgan (October 1999).

Other means of topical administration include, for example, delivery by electroporation, iontophoresis, phonophoresis, sonophoresis and microneedle or needle-free (e.g. Powderject (registered trademark), Bioject (registered trademark), etc) injection.

Formulations for topical administration may be formulated to be immediate and/or modified release. Modified release formulations include, for example, delayed-, sustained-, pulsed-, controlled-, targeted and programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in WO 91/11172, WO 94/02518 and WO 98/55148. KIT consisting of several parts It is within the scope of the present invention that two or more pharmaceutical compositions, at least one of which contains a compound in accordance with the invention, may conveniently be combined in the form of a kit suitable for administer a combination, for example, coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, based on an average human subject having a weight of about 65 kg to about 70 kg, the total daily dose of the compounds of the invention is typically in the range of about 0.05 mg to about 1000 mg, preferred in the range of about 0.1 mg to about 100 mg and more preferred in the range of about 0.5 mg to about 20 mg. Depending, of course, on the mode of administration, for example, oral administration may require a total daily dose of from about 1 mg to about 500 mg, while an intravenous dose may only require from about 0.5 mg to about 250 mg. The total daily dose may be administered in single or divided doses. These dosages can be adequately changed based on gender, age, or disease conditions of human subjects.

As discussed above, a compound of the invention exhibits $5\text{-HT}_{2B}$ antagonist activity. A $5\text{-HT}_{2B}$ antagonist of the present invention may be usefully combined with another pharmacologically active compound, or with two or more other pharmacologically active compounds, particularly in the treatment of the cancer, inflammatory diseases, immunomodulatory diseases and gastrointestinal disorder, for example, motor disorder in the digestive tract and sensory irritation, or adjustments of pulmonary blood pressure and arterial repair.

For example, $5\text{-HT}_{2B}$ antagonist, particularly a compound of the formula (I), or a pharmaceutically acceptable salt thereof, as defined above, may be administered simultaneously, sequentially or separately in combination with one or more agents selected from:

[List 1]

Laxatives: e.g. Regulan (registered trademark) and Celevac (registered trademark) are cited; Anticonvulsant factor: e.g. mebeverine, pinaverium, otilonium bromide, and trimebutine which have smooth muscle relaxant effect; e.g. dicycloverine, hyoscyamine, and cimetropium which have anti-muscarinic actions are cited.

Opioid/centrally acting drug: e.g. loperamide, naltrexone, methylnaltrexone, modulon (registered trademark), and alvimopan which are MOR agonists; e.g. fedotozine, and asimadoline which are KOR agonists; e.g. imipramine, amitriptyline, clomipramine, desipramine and lofepramine which are tricyclic antidepressants; e.g. sertraline, paroxetine, fluoxetine and escitalopram which are selective serotonin reuptake inhibitors; e.g. venlafaxine and duloxetine which are selective serotonin-noradrenalin reuptake inhibitors; e.g. moclobemide which is monoamine oxidase reversible inhibitor; e.g. diazepam, prazepam, clonazepam and dextofisopam which are benzodiazepine agonists; e.g. oxymorphone ER and tramadol, which are central analgesics; e.g. isocarboxazid, phenelzine, tranycypromine and selegiline, which are monoamine oxidase inhibitors; are cited.

Serotonergic receptor modulators: e.g. alosetron, ondansetron, tropisetron, palonosetron, ramosetron, mitrazapine, indisetron, cilansetron, granisetron and dolasetron, which are 5-HT3 antagonists; e.g. tegaserod and mosapride, which are 5-HT4 agonists; e.g. MKC-733 which is 5-HT3 agonist; e.g. renzapride, which is 5-HT4 agonists/5-HT3 antagonist; e.g. indisetron, which is 5-HT3/5-HT4 antagonist; e.g. DR-4004, SB-269970, SB-258719 and SB-258741, which are 5-HT7 antagonist; e.g. buspirone and epirone, which are 5-HT1A agonist or antagonists; e.g. buspirone which is 5-HT1A/1B/D agonist; e.g. ergotamine, sumatriptan and rizatriptan, which are migraine drugs; are cited.

Gastrointestinal motility factor: e.g. maropitant, aprepitant and ezlopitant, which are NK1 antagonists; e.g. nepadutant and saredutant, which are NK2 antagonists; e.g. talnetant, which is NK3 antagonist; e.g. CP-154526, NBI-35965 and CRA-1000, which are CRF1 receptor antagonists; e.g. dexloxiglumide, which are CCK-A receptor antagonists; e.g. mitemcinal and PF-4548043, which are motilin agonists; e.g. lubiprostone, which is chloride channel agonist (type 2); e.g. linaclotide, which is guanylate cyclase agonist; e.g. GTP-010, which is glucagon-like peptide-1 agonist; e.g. ibutamoren and capromorelin, which are ghrelin receptor agonists; are cited.

Antibiotics: e.g. sulfacetamide, erythromycin, rifaximin, tobramycin and ciprofloxacin are cited.

Probiotic bacteria: e.g. bifidobacterium, Nonpathogenic, infantis 35624 and *E. coli* are cited.

Antianalgesic factor: e.g. clonidine, medetomidine, lofexidine, dexmedetomidine and AGN-2-3818, which are alpha2-adrenergic drugs; e.g. solabegron, which is beta3-adrenergic drug; e.g. GRC-10622, GW842166 and S-777469, which are cannabinoid 1 or 2 agonists; e.g. celecoxib, rofecoxib, valdecoxib, etoricoxib and lumiracoxib which are selective COX-2 inhibitors; e.g. piroxicam, naproxen, ibuprofen, diclofenac and indomethacin, which are nonsteroidal antiinflammatory drugs (NSAIDs); e.g. dizocilpine, which is NMDA antagonist; e.g. resiniferatoxin and capsazepine, which are TRPs modulators (V1, V3, V4, M8, A1 subtypes); e.g. gabapentin, pregabalin and 3-methylgabapentin, which are alpha-2-delta ligands; e.g. topiramate, cinolazepam and clonazepam, which are GABA agonists; are cited.

Anti-inflammatory factor: e.g. dexamethasone, prednisolone, ciclesonide and budesonide, which are synthetic adrenocortical hormone; e.g. anakinra, atlizumab and mepolizumab, which are interleukin-based therapeutics; are cited.

Anti-allergy factor: e.g. montelukast, zafirlukast and pranlukast, which are leukotriene antagonists; e.g. albuterol, levalbuterol, salmeterol, formotero and arformoterol, which are beta-2 agonists; e.g. roflumilast, tiotropium and israpafant, which are asthma and/or chronic obstructive pulmonary disease treatments; are cited.

Other therapeutics: e.g. polyful (registered trademark), Metamucil (registered trademark), crofelemer and psyllium husks are cited.

Pulmonary hypertension associated: e.g. beraprost, which is prostaglandin derivative; e.g. sildenafil, which is PDE5 inhibitor; e.g. bosentan, which is endothelin-1 antagonist; are cited.

EXAMPLES

Hereinafter, the present invention is described in detail by the examples, but the following examples never limit the present invention, and various changes may be made without departing from the scope of the invention. Also included within the scope of the invention are such various changes made without departing from the scope of the invention.

The invention is illustrated in the following non-limiting examples in which, unless stated otherwise: all operations were carried out at room or ambient temperature, that is, in the range of about 18-25° C.; evaporation of solvent was carried out using a rotary evaporator under reduced pressure with a bath temperature of up to about 60° C.; reactions were monitored by thin layer chromatography (TLC) and reaction times are given for illustration only; melting points (m.p.) given are uncorrected (polymorphism may result in different melting points); the structure and purity of all isolated compounds were assured by at least one of the following techniques: TLC (Merck silicagel 60 $F_{254}$ precoated TLC plates or Merck $NH_2$ $F_{254s}$ precoated HPTLC plates), mass spectrometry, nuclear magnetic resonance (NMR), infrared red absorption spectra (IR), or microanalysis. Yields are given for illustrative purposes only. Flash column chromatography was carried out using WAKO silicagel 300 HG (40-60 micrometer) or Fuji Silysia Chromatorex (registered trademark) DU3050 (Amino Type, 30-50 micrometer) or Biotage silica (32-63 mm, KP-Sil) or Biotage amino bounded silica (35-75 mm, KP-NH).

Microwave apparatus used in the reaction was Emrys optimizer (Personal chemistry) or Initiator (registered trademark) Sixty (Biotage). Ultra sonic apparatus used in the reaction was Ultra Sonic Cleaner SINGLE Frequency (AS ONE). The abbreviations of reaction solvents are as follows: Tetrahydrofuran (THF), dimethylsulfoxide (DMSO), and dimethylformamide (DMF). In addition, 2-(1H-benzotriazol-1-yl)-1,1,3,3-tetramethyluronium hexafluorophosphate (HBTU).

The purification using HPLC in the final compound was performed by the following apparatus and conditions.

Apparatus: MS-trigger AutoPurification (registered trademark) system, waters (called purification apparatus A hereafter)

Column: XTerra C18, 19×50 mm, 5 um particle;

Method A: methanol or acetonitrile/0.05% (v/v) formic acid aqueous solution or

Method B: methanol or acetonitrile/0.01% (v/v) aqueous ammonia solution.

Confirming the chemical purity in the purity method using purification apparatus A was performed by the following apparatus and conditions.

Apparatus: Acquity Ultra Parformance LC on TUV Detector and ZQ mass spectrometer, waters Column: waters ACQUITY C18, 2.1×50 mm, 1.7 micrometer particle Column temperature: 60° C., Flow rate: 10 mL/min, UV detector: 210 nm, MS detection: ESI positive mode, method: QC_neutral_full_1 pt5 min Eluent: acetonitril/10 mM ammonium acetate solution, Gradient: 5% (0-0.1 min), 5-95% (0.10-8 min), Time for analysis: 1.5 min.

The purification using HPLC was performed by the following apparatus and conditions.

Apparatus: UV-trigger preparative HPLC system, waters (called purification apparatus B hereafter)

Column: XTerra MS C18, 5 micrometer, 19×50 mm or 30×50 mm,

Detector: UV 254 nm,

Flow rate: 20 ml/min (19×50 mm) or 40 ml/min (30×50 mm) at room temperature.

Low-resolution mass spectral data (EI) were obtained on an Integrity (waters) mass spectrometer or an Automass 120 (JEOL) mass spectrometer or 6890GC/5793MSD (GC-MS Agilent Technologies).

Low-resolution mass spectral data (ESI) were obtained by the following apparatus and conditions.

Apparatus: waters Alliance HPLC system on ZQ or ZMD mass spectrometer and UV detector, When some bromine atoms are contained in the molecule, taking isotope abundance ratio into consideration, two or more numerical values may be described depending on the number of bromine atoms.

Column: waters XTerra (registered trademark) C18, 2.1×30 mm, 3.5 micrometer particle, Gradient: 4-96% (0-2 min), 96% (2-4 min), Flow rate; 0.5 mL/min, UV detection: 254 nm, MS detection: ESI posi/nega mode, Eluent: acetonitrile/0.025% (v/v) aqueous ammonium formate solution (Neutral full range), acetonitrile/0.05% aqueous formic acid solution (Acidic full range), acetonitrile/0.01% aqueous ammonia solution (Basic full range).

NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm).

Conventional abbreviations used are: s=singlet, d=doublet, t=triplet, q=quartet, m=multiplet, br.=broad, etc. IR spectra were measured by a Shimadzu infrared spectrometer (IR-470). Optical rotations were measured using a JASCO DIP-370 Digital Polarimeter (Japan Spectroscopic Co., Ltd.). Chemical symbols have their usual meanings; b.p. (boiling point), m.p. (melting point), L (liter(s)), mL (milliliter(s)), g (gram(s)), mg(milligram(s)), mol (moles), mmol (millimoles). Then protecting group Ts means p-toluenesulfonic acid.

Example Compound 1

Synthesis of 5-(1H-indol-2-yl)-1-methyl-N-[2-(piperidin-1-yl)ethyl]-1H-pyrazole-3-carboxamide Intermediate 2

Synthesis of methyl 3-cyano-2-sodiumoxy-2-propenoate

A small piece of sodium metal (75.87 g, 2.79 mol) was added with several portions to ice cooled methanol (1.2 L). After disappearing the sodium metal, the mixture of dimethyl oxalic acid (300 g, 2.541 mol) and acetonitril (114.72 g, 2.79 mol) in methanol was added dropwise to methanol solution of sodium methoxide prepared above. Then concentrating the mixture in vacuo gave the yellow intermediate 2 (377.4 g, 99.5% yield). The intermediate 2 was used in the next step without further purification.

Intermediate 3

Synthesis of methylhydrazine sulfate

Sulfonic acid (23.4 g, 0.238 mol) was added dropwise to 40% methylhydrazine solution (25 g, 0.217 mol). After added completely, the reaction mixture was starred for 4 hours. The resulting mixture was dried up with freeze dry and the intermediate 3 was obtained.

Intermediate 4

Synthesis of methyl 5-amino-1-methyl-1H-pyrazol-3-carboxylate

The intermediate 3 (280 g, 1.94 mol) was added to the methanol suspension (1.5 L) of intermediate 2 (263.39 g, 1.77 mol). The resulting mixture was starred for 48 hours at room temperature. After that, 2 M sodium hydroxide (200 mL) and dichloromethane (1 L) was added to the reaction mixture, and the organic layer was separated. After the resulting organic layer was washed with saturated sodium chloride, and was dried over anhydrous sodium sulfate. After filtered the drying agent, concentrating the resulting filtrate in vacuo gave yellow crystal of crude intermediate 4 (82.20 g, 30% yield). The resulting intermediate 4 was used in the next step without further purification.

Intermediate 5

Synthesis of methyl 5-iodo-1-methyl-1H-pyrazol-3-carboxylate

A sodium sulfite (17.06 g, 0.247 mol) solution was added carefully dropwise to the acetic acid-water solution (3/1(v/v), 300 mL) of the intermediate 4 (32.0 g, 0.206 mol) and potassium iodide (342.4 g, 2.06 mol). After dropping, the reaction mixture was starred for 3 hours at 0° C. After confirming the consuming the intermediate 4 with TLC (ethyl acetate:hexane=1:4 (v/v)), the resulting mixture was adjusted to pH10 to pH 11 with adding solid sodium hydrogen carbonate. The aqueous layer was extracted with 1100 mL of ethyl acetate three times. Then the collected organic layer was dried over anhydrous sodium sulfate. After filtration, the concentrated filtrate under reduce pressure gave a brown syrupy crude intermediate 5. The resulting crude intermediate 5 was purified with column chromatography using silicagel (Ethyl acetate/petroleum ether, (0/1-1/3(v/v)) and the intermediate 5 (16.4 g, 30% yield) as a white crystal.
$^1$H-NMR (270 MHz, CDCl$_3$) δ 6.98 (s, 1H), 4.01 (s, 3H), 3.92 (s, 3H).
MS (ESI)m/z: [M+H]$^+$267.

Intermediate 7

Synthesis of 5-(1H-indol-2-yl)-1-methyl1-1H-pyrazol-3-carboxylic acid

Synthesis of 2-(4,4,5,5-tetramethyl-1,3,2-dioxabolan-2-yl)-1H-indole by C—H borylation An absolute dioxiane solution (25 mL) of a mixture of 1H-indol-(2.50 g, 21.3 mmol), [Ir(OMe)(COD)]$_2$(28.4 mg, 0.042 mmol), 4,4'-ditert-butyl-2,2'-bipyridyl(dtbpy)(22.9 mg, 0.085 mmol) and bis(pinacholate)diborane (3.25 g, 12.8 mmol) was starred at 80° C. for 1 hour. This reaction solution was used in the next step without any purification.

Intermediate 6 by Suzuki Coupling

Synthesis of methyl 5-(1H-indol-2-yl)-1-methyl-1H-pyrazol-3-carboxylate

The intermediate 5(3.73 g, 14.0 mmol), tris(dibenzylideneacetone) dipalladium (0)(128 mg, 0.14 mmol), potassium phosphate solution (4.88 g, 23 mmol), tricyclohexylphosphine (78.5 mg, 0.28 mmol) and water (3 mL) was added to the solution of reaction mixture above.
$^1$H-NMR (270 MHz, CDCl$_3$) δ 8.40 (br s, 1H), 7.68 (d, J=7.3 Hz, 1H), 7.44 (d, J=6.6 Hz, 1H), 7.31-7.25 (m, 1H), 7.21-7.15 (m, 1H), 7.04 (s, 1H), 6.75 (s, 1H), 4.15 (s, 3H), 3.97 (s, 3H).

Intermediate 7

Synthesis of 5-(1H-indol-2-yl)-1-methyl1-1H-pyrazol-3-carboxylic acid

Methanol (15 mL)-THF (5 mL) reaction solution of intermediate 6 (742 mg, 2.91 mmol) and 2M sodium hydroxide solution (5 mL, 10 mmol) was starred at 70° C. for 1 hour. After cool down to the room temperature, the reaction mixture was adjusted to pH3 with 2M HCl solution and diluted with saturated sodium chloride. The mixture was extracted with dichloromethane, the combined organic layer was dried over anhydrous magnesium sulfate. After filtration, the organic layer was concentrated under reduced pressure and the crude product of the intermediate 7 (673 mg, 96%) was isolated as a white solid.
$^1$H-NMR (300 MHz, DMSO-d$_6$) δ 11.58 (s, 1H), 7.61 (d, J=8.0 Hz, 1H), 7.42 (d, J=8.0 Hz, 1H), 7.22-7.10 (m, 2H), 7.09-7.02 (m, 1H), 6.88 (s, 1H), 4.12 (s, 3H). No peak was observed caused by NH.
MS (ESI) m/z: [M+H]$^+$242, [M−H]$^-$240.

Intermediate 7

Alternative synthesis of 5-(1H-indol-2-yl)-1-methyl-1H-pyrazol-3-carboxylic acid Intermediate 8

Synthesis of tert-butyl 2-[3-(methoxycarbonyl)-1-methyl-1H-pyrazol-5-yl]-1H-indol-1-carboxylate The intermediate 5(3.14 g, 11.8 mmol), palladium acetate (265 mg, 1.18 mmol), and triphenylphosphine (1.24 g, 4.71 mmol) was dissolved in dioxane/toluene solution (3.5/1(v/v), 27 mL). The resulting solution was starred at room temperature for 10 minutes. After that, tert-butyl 2-(dihydroxyboranyl)-1H-indol-1-carboxylic acid ester (4.00 g, 15.3 mmol), water (3 mL), and sodium carbonate (3.12 g, 29.5 mmol) was added to the reaction solution. The solution was refluxed for 1.5 hours. After cooling, the reaction solution was added to water (150 mL). Then aqueous layer was extracted with ethyl acetate (150 mLx2). After the resulting organic layer was dried over magnesium sulfate, the drying agents were filtrated. The filtrate was concentrated under reduced pressure. The residue was pretreated with column chromatography (ethyl acetate) using silicagel treated with amine. Then the intermediate 8 (1.72 g, 41% yield) was obtained as white solid by purification using silicagel column chromatography (hexane-ether (1.5/1-1/1)(v/v)).

$^1$H-NMR (300 MHz, CDCl$_3$) δ 8.29 (d, J=8.1 Hz, 1H), 7.61 (d, J=8.0 Hz, 1H), 7.42 (t, J=7.3 Hz, 1H), 7.31 (t, J=7.3 Hz, 1H), 6.88 (s, 1H), 6.71 (s, 1H), 3.96 (s, 3H), 3.79 (s, 3H), 1.39 (s, 9H). MS (ESI) m/z: [M+H]$^+$356.

Intermediate 7

Synthesis of 5-(1H-indol-2-yl)-1-methyl1-1H-pyrazol-3-carboxylic acid

A 2M sodium hydroxide solution (12.1 mL, 24.2 mmol) was added to a methanol solution of the intermediate 8 (1.72 g, 4.84 mmol) at 50° C. for 7 hours. After cooling, the resulting mixture was added to the reaction solution until pH 3. Then water was added to the mixture. The resulting precipitate was filtered, and was washed with small amount of water. The intermediate 7 (106 g, 90% yield) was obtained as white solid.

$^1$H-NMR (300 MHz, DMSO-d$_6$) δ 11.59 (s, 1H), 7.61 (d, J=7.3 Hz, 1H), 7.42 (d, J=8.1 Hz, 1H), 7.18 (t, J=8.0 Hz, 1H), 7.14 (s, 1H), 7.06 (t, J=8.1 Hz, 1H), 6.88 (s, 1H), 4.12 (s, 3H). NO PEAK WAS OBSERVED CAUSED BY NH.

MS (ESI)m/z: [M+H]$^+$242, [M–H]$^-$240.

Intermediate 10

Synthesis of 5-(5-fluoro-1H-indol-2-yl)-1-methyl-1H-pyrazol-3-carboxylic acid

Intermediate 9

Synthesis of tert-butyl 5-fluoro2-[3-(methoxycarbonyl)-1-methyl-1H-pyrazol-5-yl]-1H-indol-1-carboxylate Sodium carbonate (2.53 g, 23.89 mmol) and water (3 mL) was added to the intermediate 5 (2.50 g, 9.56 mmol), palladium acetate (II) (215 mg, 0.96 mmol), triphenylphosphine (100 g, 3.82 mmol) and tert-butyl 2-(dihydroxyboranyl)-5-fluoro-1H-indol-1-carboxylic acid ester (3.20 g, 11.47 mmol) in the mixture of dioxane (20 mL) and toluene (10 mL). The resulting mixture was refluxed for 1.5 hours. After cooling to room temperature, reaction solution was added to water (80 mL) and extracted with ethyl acetate (100 mLx2). The combined extract was dried over anhydrous magnesium sulfate. The drying agent was filtrated. The filtrate was concentrated under reduced pressure. The obtained residue was purified with column chromatography (hexane/ethyl acetate=2:1(v/v)) using amine silicagel. Then the intermediate 10 (990 mg, 37% yield) was obtained as white solid.

MS (ESI)m/z: [M+H]$^+$374.

Intermediate 10

Synthesis of 5-(5-fluoro-1H-indol-2-yl)-1-methyl-1H-pyrazol-3-carboxylic acid

A 2M sodium hydroxide solution (6.6 mL, 13.26 mmol) was added to THF (10 mL) solution of the intermediate 9 (990 mg, 2.65 mmol). The resulting solution was stirred at 45° C. for 2 hours and was stirred at room temperature through the night. The reaction solution was concentrated under reduced pressure. Then, a 2M HCl solution (8 mL) was added to the obtained residue. The resulting solution was extracted with ethyl acetate (120 mLx2), and the combined extract was dried over anhydrous magnesium sulfate. After the drying agents were filtered, the filtrate was concentrated under reduced pressure. Then the crude intermediate 10 (680 mg, 100% yield) was obtained as light-brown yellow solid $^1$H-NMR (300 MHz, CDCl$_3$/DMSO-d$_6$ (1 drop)) δ 10.49 (br s, 1H), 7.40-7.25 (m, 2H) 7.13 (s, 1H), 6.66 (s, 1H), 7.00-6.94 (m, 1H), 4.15 (s, 3H).

MS (ESI)m/z: [M+H]$^+$260, [M–H]$^-$258.

Example Compound 1

Synthesis of 5-(1H-indol-2-yl)-1-methyl-N-[2-(piperidin-1-yl)ethyl]-1H-pyrazole-3-carboxamide A DMF solution (0.5 mL) of hexafluorophosphate O-benzotriazole-1-yl-N,N,N',N'-tetramethyluronium (36 mg, 1.5 equivalent) was added to a DMF solution (0.5 mL) of the intermediate compound 7 (15 mg), amine (1.1 equivalent, 14 mg as 2-(piperidine-1-yl)ethane-1-amine), triethylamine (0.026 mL, 3 equivalent) at the room temperature. The resulting solution was stirred at 50° C. for 2 hours. After the resulting solution was concentrated under reduced pressure, a 1M sodium hydroxide solution (0.5 mL) was added to the residue, and the mixture was extracted with ethyl acetate (1 mL) twice. The residue of the combined organic layer was dissolved in a small amount of methanol. The solution was loaded to SCX cartridge (strong cation exchange cartridge) followed by washing with methanol (10 mL) and finally was eluted with a 1M ammonia-methanol solution (8 mL). The crude product obtained by the concentration was purified with a preparative HPLC (the purification apparatus A written in the beginning of {examples}).

MS (ESI)m/z: [M+H]$^+$352.

Examples synthesized by using the similar reaction described above are shown below:

Example Compound 2

5-(1H-indol-2-yl)-N-[2-(4-methoxypiperidin-1-yl)ethyl]-1-methyl-1H-pyrazole-3-carboxamide

Example Compound 3

N-[2-(4-hydroxypiperidin-1-yl)ethyl]-5-(1H-indol-2-yl)-1-methyl-1H-pyrazole-3-carboxamide

Example Compound 4

N-[2-(4-ethylpiperidin-1-yl)ethyl]-5-(1H-indol-2-yl)-1-methyl-1H-pyrazole-3-carboxamide

Example Compound 5

N-[2-(3-hydroxypiperidin-1-yl)ethyl]-5-(1H-indol-2-yl)-1-methyl-1H-pyrazole-3-carboxamide

Example Compound 6

1-(2-{[5-(1H-indol-2-yl)-1-methyl-1H-pyrazol-3-yl]formamide}ethyl)piperidine-3-carboxamide

Example Compound 7

5-(1H-indol-2-yl)-1-methyl-N-{2-[4-(propan-2-yl)piperidin-1-yl]ethyl}-1H-pyrazole-3-carboxamide

Example Compound 8

5-(1H-indol-2-yl)-1-methyl-N-[2-(4-methylpiperidin-1-yl)ethyl]-1H-pyrazole-3-carboxamide

Example Compound 9

5-(1H-indol-2-yl)-1-methyl-N-[2-(pyrrolidin-1-yl)ethyl]-1H-pyrazole-3-carboxamide

Example Compound 10

5-(1H-indol-2-yl)-1-methyl-N-[2-(2-methylpiperidin-1-yl)ethyl]-1H-pyrazole-3-carboxamide

Example Compound 11

N-[2-(4,4-difluoropiperidin-1-yl)ethyl]-5-(1H-indol-2-yl)-1-methyl-1H-pyrazole-3-carboxamide

Example Compound 12

N-[2-(2,6-dimethylmorpholin-4-yl)ethyl]-5-(1H-indol-2-yl)-1-methyl-1H-pyrazole-3-carboxamide

Example Compound 13

5-(1H-indol-2-yl)-1-methyl-N-[3-(morpholin-4-yl)propyl]-1H-pyrazole-3-carboxamide

Example Compound 14

5-(5-fluoro-1H-indol-2-yl)-N-[2-[(2S)-2-(methoxymethyl)pyrrolidin-1-yl]ethyl]-1-methyl-1H-pyrazole-3-carboxamide

Example Compound 15

5-(5-fluoro-1H-indol-2-yl)-N-{2-[(2R)-2-(methoxymethyl)pyrrolidin-1-yl]ethyl}-1-methyl-1H-pyrazole-3-carboxamide

Example Compound 16

5-(5-fluoro-1H-indol-2-yl)-N-{2-[(3S)-3-hydroxypyrrolidin-1-yl]ethyl}-1-methyl-1H-pyrazole-3-carboxamide

TABLE 1

| Example Compound number | | Amine |
|---|---|---|
| 2 | 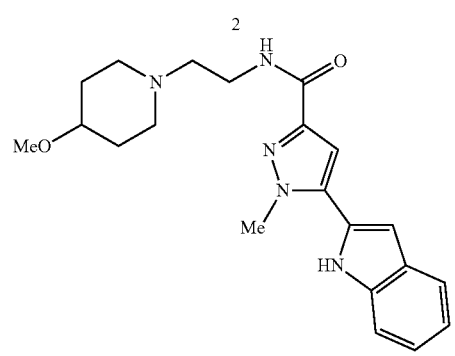 | |

TABLE 1-continued
| Example Compound number | Amine |
|---|---|
| 3 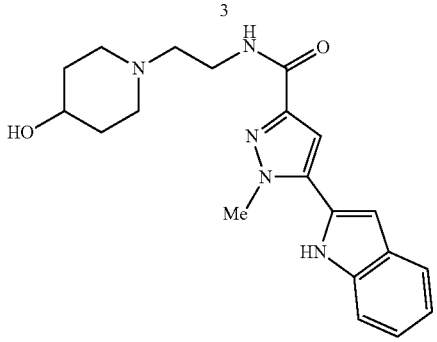 | 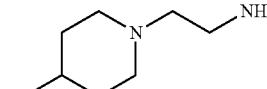 |
| 4 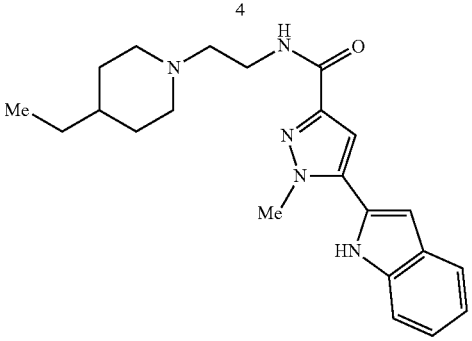 | 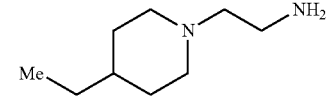 |
| 5 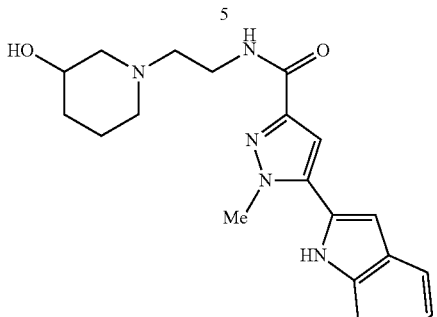 | 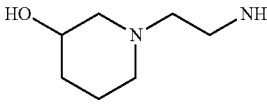 |
| 6 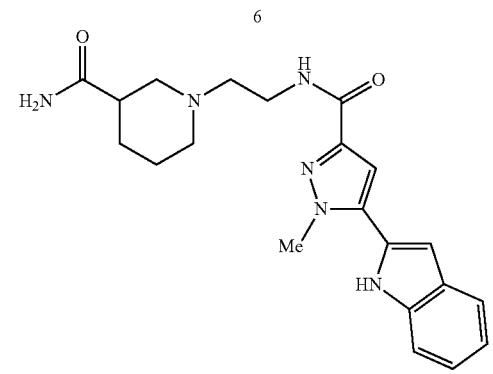 | 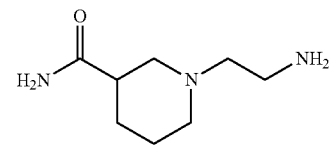 |

TABLE 1-continued

| Example Compound number | Amine |
|---|---|
| 7 (structure) | (structure) |
| 8 (structure) | (structure) |
| 9 (structure) | (structure) |
| 10 (structure) | (structure) |

TABLE 1-continued

| Example Compound number | Amine |
| --- | --- |
| 11 (4,4-difluoropiperidinyl-ethyl amide of 1-methyl-5-(1H-indol-2-yl)-pyrazole-3-carboxylic acid) | 2-(4,4-difluoropiperidin-1-yl)ethanamine |
| 12 (2,6-dimethylmorpholinyl-ethyl amide) | 2-(2,6-dimethylmorpholino)ethanamine |
| 13 (morpholinyl-propyl amide) | 3-morpholinopropan-1-amine |
| 14 ((S)-2-(methoxymethyl)pyrrolidinyl-ethyl amide of 1-methyl-5-(5-fluoro-1H-indol-2-yl)-pyrazole-3-carboxylic acid) | (S)-2-(2-(methoxymethyl)pyrrolidin-1-yl)ethanamine |

TABLE 1-continued

| Example Compound number | Amine |
|---|---|
| 15 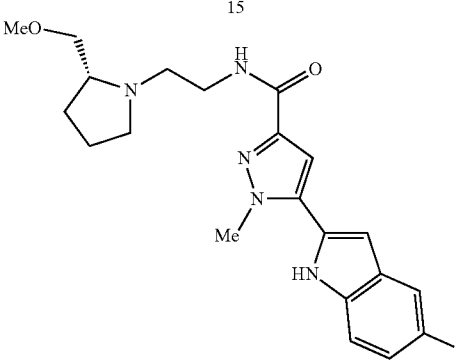 | 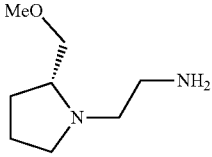 |
| 16 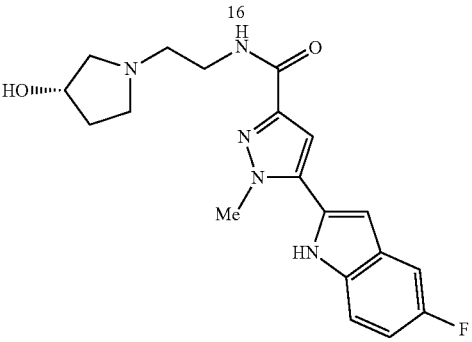 | 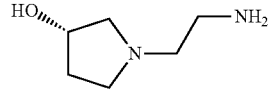 |

TABLE 2

| Example Compound number | MS (ESI) m/z | Example Compound number | MS (ESI) m/z |
|---|---|---|---|
| 2 | [M + H]$^+$ 382 | 3 | [M + H]$^+$ 368 |
| 4 | [M + H]$^+$ 380 | 5 | [M + H]$^+$ 368 |
| 6 | [M + H]$^+$ 395 | 7 | [M + H]$^+$ 394 |
| 8 | [M + H]$^+$ 366 | 9 | [M + H]$^+$ 338 |
| 10 | [M + H]$^+$ 366 | 11 | [M + H]$^+$ 388 |
| 12 | [M + H]$^+$ 382 | 13 | [M + H]$^+$ 368 |
| 14 | [M + H]$^+$ 400 | 15 | [M + H]$^+$ 400 |
| 16 | [M + H]$^+$ 372 | | |

Synthetic Method of Example Compound 17

Synthesis of 1-methyl-N-[2-(morpholin-4-yl)ethyl]-5-(quinolin-3-yl)-1H-pyrazole-3-carboxamide Intermediate 11

Synthesis of methyl 1-methyl-5-(quinolin-3-yl)-1H-pyrazol-3-carboxylate

Tris(dibenzylideneacetone)dipalladium(0) (540 mg, 0.59 mmol) was added to the mixed solution of the intermediate 5 (1.57 g, 5.90 mmol), 3-quinolineboronic acid (102 g, 5.90 mmol), potassium phosphate (1.88 g, 8.85 mmol) and 1,4-dioxane (65 mL) of tri(cyclohexyl)phosphine (165 mg, 0.59 mmol) and water (15 mL). The reaction mixture was stirred at 100° C. overnight (15 hours). After cooling down to the room temperature, the mixed solution was diluted with an ethyl acetate solvent, and was filtered through celite for the purpose of eliminating the catalyst. After the organic layer of filtrate was separated, aqueous layer was extracted again with an ethyl acetate solvent. After the combined organic layer was washed with a saturated sodium chloride solution, dried over sodium sulfate. After filtration, the residue was obtained. Purification of the residue with column chromatography (hexane-ethyl acetate=(1/1)(v/v) to (2/3)(v/v)) using silicagel afforded the intermediate 11 (873 mg, 55% yield) as slightly yellow crystal.

$^1$H-NMR (300 MHz, CDCl3) δ 8.99 (d, J=2.2 Hz, 1H), 8.23 (d, J=2.2 Hz, 1H), 8.18 (d, J=8.8 Hz, 1H), 7.79-7.75 (m, 2H), 7.54-7.52 (m, 1H), 7.04 (s, 1H), 4.05 (s, 3H), 3.98 (s, 3H).

MS(ESI)m/z; [M+H]$^+$268.

Intermediate 12

Synthesis of 1-methyl-5-(quinolin-3-yl)-1H-pyrazol-3-carboxylic acid

A methanol solution (30 mL) of the intermediate 11 (870 mg, 3.25 mmol) and 2M sodium hydroxide solution (4.20 mL, 8.20 mmol) was stirred at 75° C. for 2 hours. After removal of the solvent, the remaining solution was adjusted to PH6 to 7 with a hydrochloric acid solution. The precipitated solid was subject to suction filtration, dried in the presence of phosphorus pentoxide in vacuo, and afforded the intermediate 12 (790 mg, 96% yield) as a light brown crystal.

$^1$H-NMR (300 MHz, DMSO-d$_5$) δ 12.8 (br s, 1H), 9.11 (d, J=2.2 Hz, 1H), 8.69 (d, J=2.2 Hz, 1H), 8.1, 3-8.04 (m, 2H), 7.90-7.81 (m, 1H), 7.75-7.66 (m, 1H), 7.13 (s, 1H), 4.05 (s, 3H).

MS (ESI)m/z; [M+H]$^+$254, [M−H]$^−$252.

Synthetic method of Example Compound 17

Synthesis of 1-methyl-N-[2-(morpholin-1-yl)ethyl]-5-(quinolin-3-yl)-1H-pyrazole-3-carboxamide According to the similar way of the example compound 1, the example compound 17 (628 mg, 86% yield) was obtained as a white crystal from the intermediate 12 (506 mg, 2.00 mmol) and 4-(2-aminoethyl)morpholine (286 mg, 2.20 mmol).

$^1$H-NMR (300 MHz, CDCl$_3$) δ 8.99 (d, J=2.2 Hz, 1H), 8.21 (d, J=2.2 Hz, 1H), 8.17 (d, J=8.1 Hz, 1H), 7.90 (d, J=8.1 Hz, 1H), 7.94-7.76 (m, 1H), 7.70-7.60 (m, 1H), 7.34-7.22 (m, 1H), 7.01 (s, 1H), 4.00 (s, 3H), 3.79-3.72 (m, 4H), 3.63-3.54 (m, 2H), 2.66-2.48 (m, 6H).

MS (ESI)m/z; [M+H]$^+$366.

Examples synthesized by using the similar reaction described above are shown below:

Example Compound 18

1-methyl-N-[2-(piperidin-1-yl)ethyl]-5-(quinolin-3-yl)-1H-pyrazole-3-carboxamide

Example Compound 19

1-methyl-N-[2-(pyrrolidin-1-yl)ethyl]-5-(quinolin-3-yl)-1H-pyrazole-3-carboxamide

TABLE 3

| Example Compound number | | Amine |
|---|---|---|
| 18 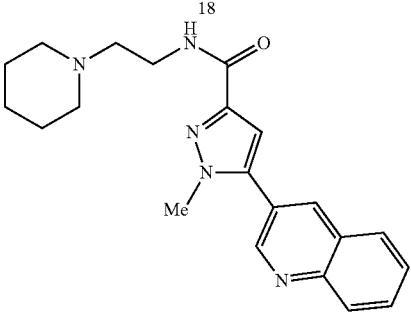 | MS (ESI) m/z [M + H]$^+$ 364 | 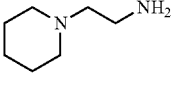 |
| 19 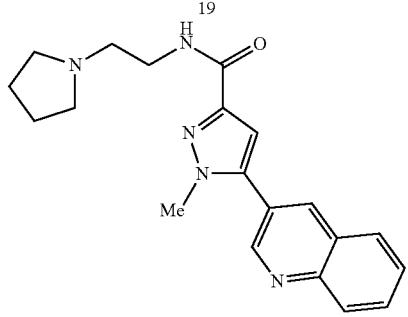 | MS (ESI) m/z [M + H]$^+$ 350 | 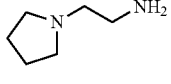 |

Example Compound 20

Synthesis of 1-methyl-N-[2-(pyrrolidin-1-yl)ethyl]-5-{1H-pyrrolo[3,2-b]pyridin-2-yl}-1H-pyrazole-3-carboxamide

Intermediate 13

Synthesis of tert-butyl 2-(dihydroxyboranyl)-1H-pyrrolo[3,2-13]-pyridine-1-carboxylate n-Butyl lithium (8.3 mL, 1.65 M, hexane solution) was added dropwise to the THF solution (10 ml) of diisopropylamine (1.39 g, 13.8 mmol) in ice-cold condition under the nitrogen atmosphere for 5 minutes. Starring the obtained mixture in ice-cold condition for 20 minutes afforded a THF solution of lithium diisopropylamide.

The THF solution of lithium diisopropylamide prepared above was added dropwise to the THF mixture (20 mL) of tert-butyl-1H-pyrrolo[3,2-b]pyridine-1-carboxylate 12 (2.00 g, 9.16 mmol) and boric acid triisopropyl ester (2.76 g, 14.66 mmol) at −20° C. under the nitrogen atmosphere for 1 hour. After the resulting mixture was stirred at −10° C. for 3 hours, a 10% potassium hydrogensulfate solution was added to the reaction solution and the resulting mixture was extracted with ethyl acetate. The obtained extract layer was washed with a saturated sodium chloride solution, and was dried over anhydrous magnesium sulfate. After filtration, the filtrate was concentrated under reduced pressure to isolate the crude intermediate 13. The obtained Intermediate 13 was suspended in diisopropyl ether. The obtained precipitation was filtered, and the crystalline intermediate 13 (1.90 g, 79% yield) was obtained.

$^1$H-NMR (300 MHz, DMSO-d$_6$) δ 8.45 (1H, d, J=4.4 Hz), 8.36 (2H, s), 8.33 (1H, d, J=8.8 Hz), 7.28 (1H, dd, J=8.1, 5.1 Hz), 6.72 (1H, s), 1.61 (9H, s).

MS (ESI)m/z: [M+H]$^+$263.

Intermediate 14

Synthesis of Methyl 5-{1-[(tert-butoxy)carbonyl]-1H-pyrrolo[3,2-b]pyridine-2-yl}-1-methyl-1H-pyrazole-3-carboxylate According to the generating method of intermediate 8, the intermediate 14 (0.37 g, 27% yield) was synthesized from the intermediate 13 (1.3 g, 5.0 mmol) and the intermediate 5 (10 g, 3.8 mmol).

$^1$H-NMR (300 MHz, DMSO-d$_6$) δ 8.61 (1H, d, J=5.1 Hz), 8.53 (1H, d, J=8.8 Hz), 7.34 (1H, dd, J=8.8, 5.1 Hz), 6.93 (2H, s), 3.96 (3H, s), 3.82 (3H, s), 1.41 (9H, s).

MS (ESI)m/z: [M+H]$^+$357.

Intermediate 15

Synthesis of 1-methyl-5-{1H-pyrrolo[3,2-b]pyridin-2-yl}-1H-pyrazol-3-carboxylic acid According to the similar method (hydrolysis) of the alternative synthesis described in the intermediate 7, the intermediate 15 (87 mg) was synthesized from the intermediate 14 (210 mg, 0.59 mmol) with 61% yield.

$^1$H-NMR (300 MHz, DMSO-d$_6$) δ 11.83 (1H, br s), 8.38 (1H, d, J=2.9 Hz), 7.80 (1H, d, J=8.1 Hz), 7.21 (1H, s), 7.18 (1H, dd, J=4.4, 8.1 Hz), 7.04 (1H, s), 4.15 (3H, s). No peak was observed caused by NH.

MS (ESI)m/z: [M+H]$^+$243.

Example Compound 20

Synthesis of 1-methyl-N-[2-(pyrrolidin-1-yl)ethyl]-5-{1H-pyrrolo[3,2-b]pyridin-2-yl}-1H-pyrazole-3-carboxamide The intermediate 15 (120 mg, 0.5 mmol) and N-(2-aminoethyl)pyrrolidine (59 mg, 0.5 mmol) was dissolved in DMF (4 mL). triethylamine (260 mg, 2.6 mmol) and N-(3-dimethylaminopropyl)-N'-ethylcarbodiimide hydrochloride (98 mg, 0.5 mmol) and 1-hydroxybenzotriazole monohydrate (39 mg, 0.3 mmol) were successively added to the resulting mixture at the room temperature. The obtained mixture was stirred at room temperature for 2 days. The solvent was removed under reduced pressure, and the resulting crude product was purified with a preparative HPLC system (the purification apparatus B) to afford crystalline product (15 mg, 9% yield).

MS (ESI)m/z: [M+H]$^+$339.

A preparative HPLC system (the purification apparatus A), which was used for the purification in the example compound 1, was used for further purification.

Example Compound 21

Synthesis of N-[2-(3-hydroxypiperidin-1-yl)ethyl]-1-methyl-5-{1H-pyrrolo[3,2-b]pyridin-2-yl}-1H-pyrazole-3-carboxamide According to the method of the example compound 20, the example compound 21 (16 mg, 34% yield) was obtained from the intermediate 15 (30 mg, 0.12 mmol) and 1-(2-aminoethyl)piperidin-3-ol (27 mg, 0.19 mmol).

MS (ESI) m/z: [M+H]$^+$369.

A preparative HPLC system (the purification apparatus A), which was used for the purification in the example compound 1, was used for further purification.

Example Compound 22

Synthesis of 1-methyl-5-{5-methyl-1H-pyrrolo[3,2-b]pyridin-2-yl}-N-[2-(morpholin-4-yl)ethyl]-1H-pyrazole-3-carboxamide

Intermediate 16

Synthesis of 5-iodo-1-methyl-1H-pyrazol-3-carboxylic acid

A 2M sodium hydroxide solution (56.4 mmol, 28.2 ml) was added to a methanol solution (100 mL) of the intermediate 5 (6.0 g, 22.6 mmol) and the mixture was heated to 50° C. Two hours later, the methanol solvent was removed under reduced pressure, and the remaining solution was adjusted to pH2 to 3 with a 2M HCl solution under ice-cold condition. After the obtained precipitated crystal was dissolved in ethyl acetate, the organic layer was separated, and then the aqueous layer was extracted with ethyl acetate twice. After the combined extracted organic layer was washed with a saturated sodium chloride solution, and dried over anhydrous sodium sulfate. After the filtration, the filtrate was concentrated under reduced pressure to afford a crude intermediate 16 (5.68 g, quantitative) as a light yellow solid.

$^1$H-NMR (270 MHz, DMSO-d$_6$) δ 12.81 (br s, 1H), 6.89 (s, 1H), 3.92 (s, 3H).

MS (ESI)m/z; [M+H]$^+$253, [M−H]$^-$251.

Intermediate 17

Synthesis of Synthesis of 5-iode1-methyl-N-[2-(morpholin-4-yl)ethyl]-1H-pyrazole-3-carboxamide 4-(2-amino-ethyl)morpholine (4.15 g, 31.9 mmol), triethylamine (12.1 mL, 86.9 mmol), 1-hydroxybenzotriazole monohydrate (8.9 g, 57.9 mmol) and N-(3-dimethylaminopropyl)-N'-ethylcarbodiimide hydrochloride (11.1 g, 57.9 mmol) were successively added to a dichloromethanee solution (150 mL) of the intermediate 16 (7.3 g, 29.0 mmol) at the room temperature. After the resulting mixture was stirred at the room temperature for 20 hours, saturated sodium bicarbonate solution was added to the reaction solution, and the aqueous layer was extracted with dichloromethanee. The obtained organic layer was dried over anhydrous sodium sulfate. After the filtration, the filtrate was concentrated under reduced pressure, and the crude intermediate 17 was isolated. Purification with column chromatography (ethyl acetate/methanol=9/1(v/v)) using silicagel afforded the intermediate 15 (9.8 g, 93% yield) as a white crystal.

$^1$H-NMR (270 MHz, CDCl$_3$) δ 6.95 (s, 1H), 3.95 (s, 3H), 3.80-3.64 (m, 4H), 3.62-3.40 (m, 2H), 2.57 (t, J=6.3 Hz, 2H), 2.54-2.37 (m, 4H). No peak was observed caused by NH.

MS (ESI) m/z; [M+H]$^+$365.

Intermediate 18

Synthesis of 1-methyl-N-[2-(morpholin-4-yl)ethyl]-5-[2-(trimethylsilyl)ethynyl]-1H-pyrazole-3-carboxamide Triethylamine (6.12 mL, 43.9 mmol) was added to a THF solution (45 mL) of the intermediate 17 (4.00 g, 10.98 mmol), copper iodide(I) (209 mg, 1.10 mmol), trimethylsilylacetylene (2.33 mL, 16.5 mmol) and dichlorobis(acetonitrile)palladium(II) chloride (770 mg, 1.10 mmol) under the nitrogen atmosphere, and the reaction mixture was stirred at the room temperature for 2 hours. After that, the resulting mixture was filtered through celite, and the obtained filtrate was concentrated under reduced pressure. The residue was purified with column chromatography (dichloromethanee/methanol=30/1 (v/v)) using silicagel to afford the intermediate 18 (3.67 g, 100% yield) as a yellow-brown solid.

$^1$H-NMR (300 MHz, CDCl$_3$) δ 7.22-7.14 (br s, 1H), 6.90 (s, 1H), 3.93 (s, 3H), 3.78-3.70 (m, 4H), 3.58-3.48 (m, 2H), 2.62-2.45 (m, 6H), 0.28 (s, 9H).

MS (ESI) m/z; [M+H]$^+$335.

Intermediate 19

Synthesis of 5-ethynyl1-methyl-N-[2-(morpholin-4-yl)ethyl]-1H-pyrazole-3-carboxamide A methanol solution (60 mL) of the intermediate 18 (3.43 g, 10.3 mmol) and potassium carbonate (2.13 g, 15.4 mmol) was stirred at the room temperature for 1.5 hours. After that, the reaction mixture was filtered through celite, and the obtained filtrate was concentrated under reduced pressure. The residue was diluted with a saturated sodium chloride solution ablution/water(1/1(V/V))(40 ml) and dichloromethanee (200 mL). After the extraction procedure, the organic layer was separated. After the obtained organic layer was dried over anhydrous sodium sulfate, the drying agent was filtered and the filtrate was concentrated under reduced pressure. The residue was purified with column chromatography (dichloromethanee/methanol=(30/1-20/1) (v/v)) using silicagel to afford the intermediate 19 (2.23 g, 83% yield) as light-brown solid.

$^1$H-NMR (270 MHz, CDCl$_3$) δ 7.20 (br s, 1H), 6.96 (s, 1H), 3.96 (s, 3H), 3.77-3.70 (m, 4H), 3.58-3.48 (m, 3H), 2.62-2.46 (m, 6H).

MS (ESI)m/z; [M+H]$^+$263.

Intermediate 20

Synthesis of 5-[2-(3-amino-6-methylpyridin-2-yl)ethynyl]-1-methyl-N-[2-(morpholin-4-yl)ethyl]-1H-pyrazole-3-carboxamide Paradium acetate (19 mg, 0.027 mmol) was added to acetonitril solution (5.0 mL) of the intermediate 19 (308 mg, 1.18 mmol), 3-amino-2-bromo-6-methylpyridine (200 mg, 107 mmol), 1,4-bis(diphenylphosphino)butane (dppb) (18.3 mg, 0.043 mmol) and Potassium carbonate (444 mg, 3.21 mmol) under the nitrogen atmosphere. The resulting mixture was stirred at 80° C. for 15 hours. After that, the resulting mixture was filtered through celite, and the obtained filtrate was concentrated under reduced pressure. The residue was purified with column chromatography (dichloromethanee/methanol=25/1-10/1(v/v)) using silicagel to afford the intermediate 20 (36.9 mg, 9.4% yield) as a dark-yellow crystal.

$^1$H-NMR (300 MHz, CDCl$_3$) δ 7.28-7.18 (br s, 1H), 7.03-6.98 (m, 3H), 4.14 (br s, 2H), 4.04 (s, 3H), 3.78-3.71 (m, 4H), 3.59-3.50 (m, 2H), 2.63-2.45 (m, 6H), 2.47 (s, 3H).

MS (ESI)m/z; [M+H]$^+$369.

Example Compound 22

Synthesis of 1-methyl-5-{5-methyl-1H-pyrrolo[3,2-b]pyridin-2-yl}-N-[2-(morpholin-4-yl)ethyl]-1H-pyrazole-3-carboxamide Potassium tert-buthoxide (56 mg, 0.5 mmol) was added to DMF (1 mL) solution of the intermediate 20(36.9 mg, 0.1 mmol) at the room temperature at a time. The resulting mixture was heated under starring at 35° C. for 2 hours. After the reaction completed, the resulting mixture was treated with water (0.5 mL) and the solvent was removed by concentration under reduced pressure. The obtained residue was purified with column chromatography (dichloromethanee/methanol=25/1-10/1(v/v)) using silicagel to afford the example compound 22 (31.3 mg, 84% yield) as a light yellow crystal.

$^1$H-NMR (300 MHz, CDCl$_3$) δ 10.4 (br s, 1H), 7.70 (d, J=8.8 Hz, 1H), 7.50-7.40 (m, 1H), 7.42 (s, 1H), 7.06 (d, J=8.8 Hz, 1H), 6.87 (s, 1H), 4.15 (s, 3H), 3.80-3.69 (m, 4H), 3.67-3.55 (m, 2H), 2.68 (s, 3H), 2.66-2.57 (m, 2H), 2.55-2.44 (m, 4H).

MS (ESI)m/z; [M+H]$^+$369, [M–H]$^-$367.

Example Compound 23

Synthesis of 5-{5,7-dimethyl-1H-pyrrolo[3,2-b]pyridin-2-yl}-1-methyl-N-[2-(morpholin-4-yl)ethyl]-1H-pyrazole-3-carboxamide

Intermediate 21

Synthesis of 5-[2-(3-amino-4,6-dimethylpyridin-2-yl)ethynyl]-1-methyl-N-[2-(morpholin-4-yl)ethyl]-1H-pyrazole-3-carboxamide According to synthetic method of the intermediate 20, the intermediate 21 (46.8 mg, 13.3% yield) was obtained as a dark-yellow amorphous from the intermediate 19 (240 mg, 0.915 mmol) and 3-amino-2-bromo-4,6-dimethylpyridine (184 mg, 0.915 mmol).

$^1$H-NMR (300 MHz, CDCl$_3$) δ 7.30-7.20 (m, 1H), 7.02 (s, 1H), 6.91 (s, 1H), 4.11 (br s, 2H), 4.04 (s, 3H), 3.80-3.71 (m, 4H), 3.60-3.50 (m, 2H), 2.65-2.48 (m, 6H), 2.43 (s, 3H), 2.19 (s, 3H).

MS (ESI)m/z: [M+H]$^+$383, [M+HCO$_2$]$^-$427.

Example Compound 23

Synthesis of 5-{5,7-dimethyl-1H-pyrrolo[3,2-b]pyridin-2-yl}-1-methyl-N-[2-(morpholin-4-yl)ethyl]-1H-pyrazole-3-carboxamide According to the similar synthetic method of the example compound 22, the example compound 23 (31.3 mg, 84% yield) was obtained as a light yellow crystal from the intermediate 21 (46.8 mg, 0.122 mmol).

$^1$H-NMR (300 MHz, CDCl$_3$) δ 9.75 (br s, 1H), 7.40-7.35 (m, 1H), 7.18 (s, 1H), 6.88 (s, 1H), 6.82 (s, 1H), 4.09 (s, 3H), 3.80-3.67 (m, 4H), 3.57-3.44 (m, 2H), 2.62 (s, 3H), 2.60-2.40 (m, 6H), 2.54 (s, 3H).

MS (ESI)m/z: [M+H]$^+$383, [M–H]$^-$381.

Example Compound 24

Synthesis of 1-methyl-N-[2-(morpholin-4-yl)ethyl]-5-{1H-pyrrolo[2,3-b]pyridin-2-yl}-1H-pyrazole-3-carboxamide

Intermediate 22

Synthesis of 5-[2-(2-aminopyridin-3-yl)ethynyl]-1-methyl-N-[2-(morpholin-4-yl)ethyl]-1H-pyrazole-3-carboxamide Triethylamine (404 mg, 4.0 mmol) was added to a THF solution (6 mL) of the intermediate 19 (262 mg, 1.00 mmol), 2-amino-3-iodopyridine (264 mg, 1.20 mmol), dichlorobis(acetonitrile)palladium(II) chloride (70.1 mg, 0.1 mmol) and copper(I) (19 mg, 0.1 mmol) under the nitrogen atmosphere. The reaction solution was stirred at the room temperature for 7.5 hours. After that, the resulting mixture was filtered through celite, and the obtained filtrate was concentrated under reduced pressure. The residue was purified with column chromatography (dichloromethanee/methanol=20/1(v/v)) using silicagel to afford the intermediate 22 (207 mg, 58.4% yield) as a yellow crystal.

$^1$H-NMR (300 MHz, CDCl$_3$) δ 8.14-8.08 (m, 1H), 7.65-7.60 (m, 1H), 7.27-7.20 (m, 1H), 6.99 (s, 1H), 6.73-6.65 (m, 1H), 5.06 (br s, 2H), 4.01 (s, 3H), 3.78-3.71 (m, 4H), 3.59-3.50 (m, 2H), 2.63-2.47 (m, 6H).

MS (ESI)m/z: [M+H]$^+$355, [M–H]$^-$353.

Example Compound 24

Synthesis of 1-methyl-N-[2-(morpholin-4-yl)ethyl]-5-{1H-pyrrolo[2,3-b]pyridin-2-yl}-1H-pyrazole-3-carboxamide According to the similar synthetic method of the example compound 22, the example compound 24 (51.5 mg, 26% yield) was obtained as a yellow crystal from the intermediate 22 (200 mg, 0.56 mmol).

$^1$H-NMR (300 MHz, CDCl$_3$) δ 12.2 (br s, 1H), 8.45-8.38 (m, 1H), 8.04-7.97 (m, 1H), 7.36 (s, 1H), 7.40-7.30 (m, 1H), 7.23-7.14 (m, 1H), 6.69 (s, 1H), 4.16 (s, 3H), 3.82-3.73 (m, 4H), 3.71-3.62 (m, 2H), 2.70-2.61 (m, 2H), 2.60-2.50 (m, 4H).
MS (ESI)m/z: [M+H]$^+$355, [M−H]$^-$353.

Example Compound 25

Synthesis of 1-methyl-N-[2-(morpholin-4-yl)ethyl]-5-{5H-pyrrolo[3,2-d]pyrimidin-6-yl}-1H-pyrazole-3-carboxamide Intermediate 23

Synthesis of 5-[2-(5-aminopyridin-4-yl)ethynyl]-1-methyl-N-[2-(morpholin-4-yl)ethyl]-1H-pyrazole-3-carboxamide According to the synthetic method of the intermediate 22, the intermediate 23 (112 mg, 41% yield) was obtained as a dark brown solid by heating under starring at 100° C. for 16 hours form the compound 19 (200 mg, 0.762 mmol) and 4-bromopyrimidin-5-amine (159 mg, 0.914 mmol).
$^1$H-NMR (300 MHz, CDCl$_3$) δ 8.64 (s, 1H), 8.34 (s, 1H), 7.09 (s, 1H), 4.41 (br s, 2H), 4.06 (s, 3H), 3.82-3.69 (m, 4H), 3.64-3.51 (m, 2H), 2.62-2.46 (m, 6H). No peak was observed caused by NH.
MS (ESI) m/z: [M+H]$^+$356, [M−H]$^-$354.

Example Compound 25

Synthesis of 1-methyl-N-[2-(morpholin-4-yl)ethyl]-5-{5H-pyrrolo[3,2-d]pyrimidin-6-yl}-1H-pyrazole-3-carboxamide According to the similar synthetic method of the example compound 22, the crude example compound 25 (41 mg, yield 37%) was obtained as a light brown solid from the intermediate 23 (112 mg, 0.315 mmol).
$^1$H-NMR (300 MHz, CDCl$_3$) δ 11.51 (br s, 1H), 9.03 (s, 1H), 9.00 (s, 1H), 7.65 (s, 1H), 6.94 (s, 1H), 4.22 (s, 3H), 3.80-3.62 (m, 6H), 2.67-2.42 (m, 6H). No peak was observed caused by NH.
MS (ESI)m/z: [M+H]$^+$356, [M−H]$^-$354.
A preparative HPLC system (the purification apparatus A), which was used for the purification in the example compound 1, was used for further purification.

Example Compound 26

Synthesis of 1-methyl-N-[2-(morpholin-4-yl)ethyl]-5-{7H-pyrrolo[2,3-d]pyrimidin-6-yl}-1H-pyrazole-3-carboxamide Intermediate 24

Synthesis of 5-[2-(4-aminopyridin-5-yl)ethynyl]-1-methyl-N-[2-(morpholin-4-yl)ethyl]-1H-pyrazole-3-carboxamide According to the similar synthetic method of the intermediate 22, the compound 19 (200 mg, 0.762 mmol) and 5-iodopyrimidine-4-amine (253 mg, 1.14 mmol) were heated under starring at 90° C. for 16 hours to afford the crude intermediate 24 (129 mg) as light yellow syrup.
$^1$H-NMR (300 MHz, CDCl$_3$) δ 8.56 (s, 1H), 8.44 (s, 1H), 7.32-7.28 (m, 1H), 7.00 (m, 1H), 6.08 (br s, 2H), 4.00 (s, 3H), 3.76-3.73 (m, 4H), 3.57-3.51 (m, 2H), 2.63-2.49 (m, 6H).
MS (ESI)m/z: [M+H]$^+$356, [M−H]$^-$354.

Example Compound 26

Synthesis of 1-methyl-N-[2-(morpholin-4-yl)ethyl]-5-{7H-pyrrolo[2,3-d]pyrimidin-6-yl}-1H-pyrazole-3-carboxamide According to the similar synthetic method of the example compound 22, the intermediate 24 (115 mg, 0.324 mmol) was heated under starring at 70° C. for 1 hour. Then crude example compound 26 (41 mg, 37% yield) was obtained as a light brown solid.
$^1$H-NMR (300 MHz, CDCl$_3$) δ 12.01 (br s, 1H), 9.03 (s, 1H), 8.90 (s, 1H), 7.89 (s, 1H), 7.55-7.51 (m, 1H), 6.77 (s, 1H), 4.22 (s, 3H), 3.96-3.90 (m, 2H), 3.78-3.75 (m, 4H), 2.72-2.51 (m, 6H).
MS (ESI)m/z: [M+H]$^+$356, [M−H]$^-$354.
A preparative HPLC system (the purification apparatus A), which was used for the purification in the example compound 1, was used for further purification.

Example Compound 27

Synthesis of 1-methyl-N-[2-(morpholin-4-yl)ethyl]-5-[5-(trifluoromethyl)-1H-pyrrolo[3,2-b]pyridin-2-yl]-1H-pyrazole-3-carboxamide Intermediate 25

Synthesis of 5-{2-[3-amino-6-(trifluoromethyl)pyridin-2-yl]ethynyl}-1-methyl-N-[2-(morpholin-4-yl)ethyl]-1H-pyrazole-3-carboxamide According to the similar synthetic method of the intermediate 20, the intermediate 19 (262 mg, 1.00 mmol) and 3-amino-2-iodo-6-trifluoromethylpyridine (288 mg, 1.00 mmol) were heated under starring at 80° C. for 14 hours and the crude product was obtained. The product was purified with column chromatography (dichloromethane/methanol=30/1-20/1(v/v)) using silicagel to afford the intermediate 25 (245 mg, 58% yield) as a white crystal.
$^1$H-NMR (300 MHz, CDCl$_3$) δ 7.48 (d, J=8.8 Hz, 1H), 7.28-7.20 (m, 1H), 7.15 (d, J=8.8 Hz, 1H), 7.05 (s, 1H), 4.67 (br s, 2H), 4.05 (s, 3H), 3.80-3.69 (m, 4H), 3.59-3.49 (m, 2H), 2.63-2.45 (m, 6H).
MS (ESI)m/z: [M+H]$^+$423, [M−H]$^-$421.

Example Compound 27

Synthesis of 1-methyl-N-[2-(morpholin-4-yl)ethyl]-5-[5-(trifluoromethyl)-1H-pyrrolo[3,2-b]pyridin-2-yl]-1H-pyrazole-3-carboxamide According to the similar synthetic method of the example compound 22, the crude product was obtained as a white crystal from the intermediate 25 (240 mg, 0.578 mmol) and potassium tert-butoxide (324 mg, 2.89 mmol). The product was purified with column chromatography (dichloromethane/methanol=15/1(v/v)) using silicagel to afford the intermediate 27 (187 mg, 78% yield) as a white crystal.
$^1$H-NMR (300 MHz, DMSO-d$_6$) δ 12.3 (br s, 1H), 8.17-8.08 (m, 1H), 8.03 (d, J=8.8 Hz, 1H), 7.64 (d, J=8.8 Hz, 1H), 7.23 (s, 1H), 7.21 (s, 1H), 4.17 (s, 3H), 3.62-3.52 (m, 4H), 3.4-3.30 (m, 2H), 2.54-2.36 (m, 6H).
MS (ESI)m/z: [M+H]$^+$383, [M−H]$^-$381.

Example Compound 28

Synthesis of 1-methyl-5-{5-methyl-1H-pyrrolo[2,3-b]pyridin-2-yl}-N-[2-(morpholin-4-yl)ethyl]-1H-pyrazole-3-carboxamide

Intermediate 26

Synthesis of 5-[2-(2-amino-5-methylpyridin-3-yl)ethynyl]-1-methyl-N-[2-(morpholin-4-yl)ethyl]-1H-pyrazole-3-carboxamide According to the similar synthetic method of the intermediate 20, the intermediate 19 (393 mg, 1.50 mmol) and 2-amino-3-iodo-5-methylpyridine (421 mg, 1.80 mmol) were heated under starring at 80° C. for 14 hours, and the crude product was obtained. The product was purified with column chromatography (dichloromethane/methanol 30/1-20/1(v/v)) using silicagel to afford the intermediate 26 (245 mg, 58% yield) as a white crystal.

$^1$H-NMR (300 MHz, CDCl$_3$) δ 7.94 (d, J=2.2 Hz, 1H), 7.46 (d, J=2.2 Hz, 1H), 7.30-7.18 (m, 1H), 6.98 (s, 1H), 4.88 (br s, 2H), 4.00 (s, 3H), 3.78-3.70 (m, 4H), 3.60-3.50 (m, 2H), 2.64-2.46 (m, 6H), 2.21 (s, 3H).
MS (ESI)m/z: [M+H]$^+$369.

Example Compound 28

Synthesis of 1-methyl-5-{5-methyl-1H-pyrrolo[2,3-b]pyridin-2-yl}-N-[2-(morpholin-4-yl)ethyl]-1H-pyrazole-3-carboxamide According to the similar synthetic method of the example compound 22, the crude product was obtained from the intermediate 26 (460 mg, 1.25 mmol) and potassium tert-butoxide (1200 mg, 10.7 mmol). The product was purified with column chromatography (dichloromethane/methanol=50/1(v/v)) using amine-silicagel and was recrystallized from methanol and diisopropyl ether to afford the example compound 28 (229 mg, 50% yield) as a white crystal.

$^1$H-NMR (300 MHz, CDCl$_3$) δ 11.8 (br s, 1H), 8.25 (d, J=1.5 Hz, 1H), 7.78 (br s, 1H), 7.38-7.27 (m, 1H), 7.34 (s, 1H), 6.59 (s, 1H), 4.14 (s, 3H), 3.80-3.62 (m, 6H), 2.68-2.50 (m, 6H), 2.47 (s, 3H).
MS (ESI)m/z: [M+H]$^+$369.

Example Compound 29

Synthesis of 5-{5-fluoro-1H-pyrrolo[2,3-b]pyridin-2-yl}-1-methyl-N-[2-(morpholin-4-yl)ethyl]-1H-pyrazole-3-carboxamide

Intermediate 27

5-[2-(2-amino-5-fluoropyridin-3-yl)ethynyl]-1-methyl-N-[2-(morpholin-4-yl)ethyl]-1H-pyrazole-3-carboxamide Triethylamine (309 mg, 3.05 mmol) was added to THF (10 mL) solution of the intermediate 19 (200 mg, 0.76 mmol), 5-fluoro3-iodopyridin-2-amine (218 mg, 0.915 mmol), dichlorobis(triphenylphosphine)palladium(II) dichloride (54 mg, 0.076 mmol), copper iodide(I) (14.5 mg, 0.076 mmol) and the mixture was stirred at the room temperature for two days. The reaction solution was concentrated under reduced pressure, and the obtained oily brown residue was purified with column chromatography (ethyl acetate as a solvent) using amine silicagel to afford the intermediate 27 (187 mg, 66% yield) as a white solid.

$^1$H-NMR (300 MHz, CDCl$_3$) δ 8.00 (d, J=2.9 Hz, 1H), 7.39 (dd, J=2.9, 8.0 Hz, 1H), 7.01 (s, 1H), 4.91 (br s, 2H), 4.01 (s, 3H), 3.74 (t, J=4.4 Hz, 4H), 3.54 (dd, J=5.9, 11.7 Hz, 2H), 2.59 (t, J=6.6 Hz, 2H), 2.50-2.20 (m, 4H). No peak caused by amide NH was observed.
MS (ESI) m/z: [M+H]$^+$373.

Example Compound 29

Synthesis of 5-{5-fluoro-1H-pyrrolo[2,3-b]pyridin-2-yl}-1-methyl-N-[2-(morpholin-4-yl)ethyl]-1H-pyrazole-3-carboxamide According to the similar synthetic method of the example compound 22, the crude product was obtained from the intermediate 27 (180 mg, 0.48 mmol) and potassium tert-butoxide (271 mg, 2.41 mmol). The product was purified with column chromatography (dichloromethane/methanol=10/1(v/v)) using silicagel and was recrystallized from methanol and diisopropyl ether to afford the intermediate 29 (110 mg, 61% yield) as a white crystal.

$^1$H-NMR (300 MHz, CDCl3) δ 11.30 (br s, 1H), 8.23 (d, J=2.2 Hz, 1H), 7.64 (dd, J=2.9, 8.8 Hz, 1H), 7.58 (s, 1H), 7.41 (br s, 1H), 6.66 (d, J=2.2 Hz, 1H), 4.17 (s, 3H), 3.83-3.70 (m, 6H), 2.66 (t, J=5.9 Hz, 2H), 2.56-2.50 (m, 4H).
MS (ESI)m/z: [M+H]$^+$373, [M−H]$^-$371.

Example Compound 30

Synthesis of 5-{5-cyano-1H-pyrrolo[3,2-b]pyridin-2-yl}-1-methyl-N-[2-(morpholin-4-yl)ethyl]-1H-pyrazole-3-carboxamide

Intermediate 28

5-[2-(3-amino-6-cyanopyridin-2-yl)ethynyl]-1-methyl-N-[2-(morpholin-4-yl)ethyl]-1H-pyrazole-3-carboxamide According to the similar synthetic method of the intermediate 20, the intermediate 19 (262 mg, 1.00 mmol) and 3-amino-2-iodo-6-cyanopyridine (245 mg, 1.00 mmol) were heated under starring at 80° C. for 14 hours, and the crude product was obtained. The product was purified with column chromatography (dichloromethane/methanol=20/1(v/v)) using silicagel to afford the intermediate 28 (231 mg, 61% yield) as a light brown solid.

$^1$H-NMR (300 MHz, DMSO-d$_6$) δ 8.20-8.12 (m, 1H), 7.68 (d, J=8.8 Hz, 1H), 7.18 (d, J=8.8 Hz, 1H), 7.11 (s, 1H), 6.83 (br s, 2H), 4.02 (s, 3H), 3.60-3.53 (m, 4H), 3.40-3.30 (m, 2H), 2.48-2.35 (m, 6H).
MS (ESI)m/z: [M+H]$^+$380.

Example Compound 30

5-{5-cyano-1H-pyrrolo[3,2-b]pyridin-2-yl}-1-methyl-N-[2-(morpholin-4-yl)ethyl]-1H-pyrazole-3-carboxamide According to the similar synthetic method of the example compound 22, the crude product was obtained from the intermediate 28 (227 mg, 0.60 mmol) and potassium tert-butoxide (674 mg, 6.00 mmol). The product was purified with column chromatography (dichloromethane/methanol=15/1(v/v)) using silicagel and was recrystallized from methanol and diisopropyl ether to afford the example compound 30 (229 mg, 50% yield) as a white crystal.

$^1$H-NMR (300 MHz, DMSO-$d_6$) δ 12.5 (br s, 1H), 8.20-8.12 (m, 1H), 8.00 (d, J=8.8 Hz, 1H), 7.76 (d, J=8.8 Hz, 1H), 7.22 (total 2H due to overlapping different (s, 1H) peaks), 4.17 (s, 3H), 3.62-3.52 (m, 4H), 3.43-3.30 (m, 2H), 2.55-2.35 (m, 6H).

MS (ESI) m/z: [M+H]$^+$380, [M−H]$^-$378.

Example Compound 31

Synthesis of 5-{6-fluoro-1H-pyrrolo[3,2-b]pyridin-2-yl}-1-methyl-N-[2-(morpholin-4-yl)ethyl]-1H-pyrazole-3-carboxamide Intermediate 29

5-[2-(5-fluoropyridin-3-nitropyridin-2-yl)ethynyl]-N-[2-(morpholin-4-yl)ethyl]-1H-pyrazole-3-carboxamide According to the similar synthetic method of the example compound 29, the intermediate 29 (307 mg, 50% yield) was obtained as a brownish-yellow solid from the intermediate 19 (400 mg, 1.53 mmol), 2-chloro-5-fluoro-3-nitropyridine (323 mg, 1.83 mmol), bis(triphenylphosphine)palladium(II) dichloride (176 mg, 0.15 mmol), copper iodide(I) (29 mg, 0.15 mmol) and triethylamine (617 mg, 6.10 mmol).

$^1$H-NMR (300 MHz, CDCl$_3$) δ 8.81 (d, J=2.2 Hz, 1H), 8.24 (dd, J=2.2, 7.3 Hz, 1H), 7.18 (s, 1H), 4.13 (s, 3H), 3.75 (t, J=5.1 Hz, 4H), 3.58-3.52 (m, 2H), 2.59 (t, J=5.9 Hz, 2H), 2.58-2.49 (m, 4H). No peak caused by amide NH was observed.

Intermediate 30

5-[2-(3-amino-5-fluoropyridin-2-yl)ethynyl]-1-methyl-N-[2-(morpholin-4-yl)ethyl]-1H-pyrazole-3-carboxamide A methanol solution of the intermediate 29 (690 mg, 1.72 mmol), tin chloride (II) (4877 mg, 25.7 mmol), ammonium chloride (1376 mg, 25.7 mmol) and water (927 mg, 51.4 mmol) was stirred at 80° C. for 16 hours. After cooling down to the room temperature, the mixture was adjusted to pH12 with a 2M sodium hydroxide solution. The obtained mixture was filtered through celite, and was washed with methanol. The filtrate was concentrated under reduced pressure and the residue was diluted with dichloromethanee and was washed with a saturated sodium chloride solution, and dried over anhydrous sodium sulfate. After the drying agent was filtered, the obtained residue was concentrated under reduced pressure to afford the crude intermediate 30 (405 mg, 63%) as a yellow solid.

MS (ESI) m/z: [M+H]$^+$373, [M−H]$^-$371.

Example Compound 31

5-{6-fluoro-1H-pyrrolo[3,2-b]pyridin-2-yl}-1-methyl-N-[2-(morpholin-4-yl)ethyl]-1H-pyrazole-3-carboxamide According to the similar synthetic method of the example compound 22, the crude product was obtained from the intermediate 30 (400 mg, 107 mmol) and potassium tert-butoxide (603 mg, 5.37 mmol). The product was purified with column chromatography (dichloromethane/methanol=20/1(v/v)) using silicagel and was recrystallized from methanol to afford the example compound 31 (71 mg, 18% yield) as a white solid.

$^1$H-NMR (300 MHz, CDCl$_3$) δ 11.23 (br s, 1H), 8.36 (s, 1H), 7.46 (d, J=8.8 Hz, 1H), 7.22 (s, 1H), 6.87 (s, 1H), 4.14 (s, 3H), 3.77-3.73 (m, 4H), 3.60-3.50 (m, 2H), 2.63-2.50 (m, 6H). No peak was observed caused by NH of pyrrolo[3,2-b]pyridine.

MS (ESI)m/z: [M+H]$^+$373, [M−H]$^-$371.

Example Compound 32

Synthesis of 1-methyl-N-[2-(morpholin-4-yl)ethyl]5-{5H-pyrrolo[2,3-b]pirazin-6-yl}-1H-pyrazole-3-carboxamide Intermediate 31

5-[2-(3-amino-pirazin-2-yl)ethynyl]-1-methyl-N-[2-(morpholin-4-yl)ethyl]-1H-pyrazole-3-carboxamide According to the similar synthetic method of the intermediate 20, the intermediate 19 (393 mg, 1.50 mmol) and 2-amino-3-chloropyrazine (233 mg, 1.80 mmol) were heated under starring at 80° C. for 14 hours and the crude product was obtained. The product was purified with column chromatography (dichloromethane/methanol=20/1-15/1(v/v)) using silicagel to afford the intermediate 31 (272 mg, 51% yield) as a light yellow solid.

$^1$H-NMR (300 MHz, CDCl$_3$) δ 8.04 (d, J=2.2 Hz, 1H), 7.99 (d, J=2.2 Hz, 1H), 7.30-7.20 (m, 1H), 7.07 (s, 1H), 5.13 (br s, 2H), 4.05 (s, 3H), 3.80-3.70 (m, 4H), 3.60-3.50 (m, 2H), 2.65-2.45 (m, 6H).

MS (ESI)m/z: [M+H]$^+$380, [M−H]$^-$378.

Example Compound 32

1-methyl-N-[2-(morpholin-4-yl)ethyl]5-{5H-pyrrolo[2,3-b]pirazin-6-yl}-1H-pyrazole-3-carboxamide According to the similar synthetic method of the example compound 22, the crude product was obtained from the intermediate 31 (267 mg, 0.75 mmol) and potassium tert-butoxide (420 mg, 3.76 mmol). The product was purified with column chromatography (dichloromethane/methanol=20/1-15/1(v/v)) using silicagel and was recrystallized from methanol and diisopropyl ether to afford the example compound 32 (183 mg, yield 69%) as a white crystal.

$^1$H-NMR (300 MHz, DMSO-$d_6$) δ 12.6 (br s, 1H), 8.46 (d, J=2.9 Hz, 1H), 8.31 (d, J=2.9 Hz, 1H), 8.18-8.09 (m, 1H), 7.25 (s, 1H), 7.13 (s, 1H), 4.17 (s, 3H), 3.62-3.53 (m, 4H), 3.43-3.30 (m, 2H), 2.55-2.35 (m, 6H).

MS (ESI)m/z: [M+H]$^+$356, [M−H]$^-$354.

Example Compound 33

Synthesis of 5-{5-cyano-1H-pyrrolo[2,3-b]pyridin-2-yl}-1-methyl-N-[2-(morpholin-4-yl)ethyl]-1H-pyrazole-3-carboxamide Intermediate 32

5-[2-(2-amino-5-cyanopyridin-3-yl)ethynyl]-1-methyl-N-[2-(morpholin-4-yl)ethyl]-1H-pyrazole-3-carboxamide According to the similar synthetic method of the intermediate 20, the intermediate 19 (393 mg, 1.50 mmol) and 2-amino-3-iodo-5-cyanopyridine (441 mg, 1.80 mmol) were heated under starring at 80° C. for 14 hours, and the crude product was obtained. The product was purified with column chromatography (dichloromethane/methanol=15/1(v/v)) using silicagel to afford the intermediate 32 (122 mg, 21% yield) as a light yellow solid.

$^1$H-NMR (300 MHz, DMSO-d$_6$) δ 8.43 (d, J=2.2 Hz, 1H), 8.16 (d, J=2.2 Hz, 1H), 8.18-8.08 (m, 1H), 7.50 (br s, 2H), 7.02 (s, 1H), 4.00 (s, 3H), 3.60-3.53 (m, 4H), 3.40-3.30 (m, 2H), 2.48-2.35 (m, 6H).

MS (ESI)m/z: [M+H]$^+$380, [M−H]$^-$378.

Example Compound 33

5-{5-cyano-1H-pyrrolo[2,3-b]pyridin-2-yl}-1-methyl-N-[2-(morpholin-4-yl)ethyl]-1H-pyrazole-3-carboxamide According to the similar synthetic method of the example compound 22, the crude product was obtained from the intermediate 32 (122 mg, 0.32 mmol) and potassium tert-butoxide (360 mg, 3.20 mmol). The product was purified with column chromatography (dichloromethane/methanol=15/1(v/v)) using silicagel and was recrystallized from methanol and diisopropyl ether to afford the example compound 33 (57 mg, 47% yield) as a white crystal.

$^1$H-NMR (300 MHz, DMSO-d$_6$) δ 12.9 (br s, 1H), 8.68 (d, J=2.2 Hz, 1H), 8.60 (d, J=2.2 Hz, 1H), 8.16-8.08 (m, 1H) 7.22 (s, 1H), 7.04 (s, 1H) 4.14 (s, 3H), 3.62-3.53 (m, 4H), 3.42-3.30 (m, 2H), 2.55-2.35 (m, 6H).

MS (ESI)m/z: [M+H]$^+$380, [M−H]$^-$378.

Example Compound 34

Synthesis of 5-{imidazo[1,2-a]pyridin-2-yl}-1-methyl-N-[2-(morpholin-4-yl)ethyl]-1H-pyrazole-3-carboxamide Intermediate 33

Synthesis of ethyl 5-acetyl1-methyl-1H-pyrazol-3-carboxylate

A DMF solution (10 mL) of ethyl 5-acetyl 1H-pyrazol-3-carboxylate (1.50 g, 8.23 mmol, reference: U.S. Pat. No. 5,470,862) was added dropwise to a DMF suspension (10 mL) of 60% (w/w; in oil) sodium hydride (442 mg, 11.5 mmol) in ice-cold condition. The resulting mixture was stirred at the room temperature for 10 minutes, and iodomethane (103 mL, 16.5 mmol) was added to the reaction solution, and was stirred at the room temperature for 30 minutes. After that, the reaction solution was added to water (20 mL) and the aqueous layer was extracted with ether (80 mL×2). After the obtained organic layer was dried over magnesium sulfate, the drying agent was filtered, and the filtrate was concentrated under reduced pressure. The residue was purified with column chromatography (hexane/ethyl acetate=10/1-6/1(v/v)) using silicagel to afford the intermediate 33 (180 mg, 11% yield) as a white crystal.

$^1$H-NMR (300 MHz, CDCl$_3$) δ 7.36 (s, 1H), 4.43 (q, J=7.3 Hz, 2H), 4.24 (s, 3H), 2.56 (s, 3H), 1.42 (t, J=7.3 Hz, 3H).

MS (ESI)m/z: [M+H]$^+$197.

Intermediate 34

Synthesis of ethyl 5-(2-bromoacetyl)-1-methyl-1H-pyrazol-3-carboxylate

Phenyltrimethylammonium bromide (148 mg, 0.40 mmol) was added to a THF solution (1 mL) of the intermediate 33 (79 mg, 0.40 mmol), and the mixture was stirred at the room temperature for 1.5 hours. The obtained reaction solution was added to water (20 mL). The aqueous layer was extracted with ether (20 mL×2). After the obtained organic layer was dried over magnesium sulfate, the drying agent was filtered, and the filtrate was concentrated under reduced pressure. The residual solid was washed with a small amount of isopropyl ether/hexane=1/2(v/v), and the intermediate 34 (114 mg, quantitative) was obtained as a white crystal.

$^1$H-NMR (300 MHz, CDCl$_3$) δ 7.45 (s, 1H), 4.44 (q, J=7.3 Hz, 2H), 4.31 (s, 2H), 4.26 (s, 3H), 1.42 (t, J=7.3 Hz, 3H).

MS (ESI)m/z: [M+H]$^+$275 & 277.

Intermediate 35

Synthesis of ethyl 5-{imidazo[1,2-a]pyridin-2-yl}-1-methyl-1H-pyrazol-3-carboxylate A methanol solution (2 mL) of the intermediate 34 (114 mg, 0.41 mmol) and 2-aminopyridine (39 mg, 0.41 mmol) was heated at reflux for 20 hours. After cooling, the reaction solution was added to a saturated sodium bicarbonate solution (20 mL) and the aqueous layer was extracted with dichloromethane (20 mL×2). The obtained organic layer was dried over magnesium sulfate. After the drying agents were filtered, the filtrate was concentrated under reduced pressure. The residue was purified with column chromatography (hexane/ethyl acetate=1/3(v/v)) using silicagel to afford the intermediate 35 (64 mg, 57% yield) as a light yellow solid.

$^1$H-NMR (300 MHz, CDCl$_3$) δ 8.16 (d, J=6.6 Hz, 1H), 7.81 (s, 1H), 7.65 (d, J=8.8 Hz, 1H), 7.28-7.20 (m, 1H), 7.09 (s, 1H), 6.87 (t, J=7.3 Hz, 1H), 4.43 (q, J=6.6 Hz, 2H), 4.34 (s, 3H), 1.43 (t, J=6.6 Hz, 3H).

MS (ESI)m/z: [M+H]$^+$271.

Intermediate 36

Synthesis of 5-{imidazo[1,2-a]pyridin-2-yl}-1-methyl-1H-pyrazol-3-carboxylic acid A 2M sodium hydroxide solution (0.25 mL, 0.50 mmol) was added to a methanol solution (1 mL) of the intermediate 35 (60 mg, 0.22 mmol), and the mixture was stirred at 70° C. for 1 hour. After cooling, a 2M HCl solution (0.25 mL, 0.50 mmol) was added to the reaction solution, and the resulting mixture was concentrated under reduced pressure to afford the intermediate 36 (54 mg) of a white crystal as a mixture of sodium chloride. The intermediate was used for the following reaction without any further purification.

$^1$H-NMR (300 MHz, CDCl$_3$) δ 8.57 (d, J=7.3 Hz, 1H), 8.42 (s, 1H), 7.64 (d, J=10.2 Hz, 1H), 7.33 (t, 10.3 Hz, 1H), 7.00 (s, 1H), 6.98 (t, J=7.3 Hz, 1H), 4.25 (s, 3H). No peak was obsessed caused by COOH MS (ESI)m/z: [M+H]$^+$243, [M−H]$^-$241.

Example Compound 34

Synthesis of 5-{imidazo[1,2-a]pyridin-2-yl}-1-methyl-N-[2-(morpholin-4-yl)ethyl]-1H-pyrazole-3-carboxamide Hexafluorophosphate O-benzotriazole-1-yl-N,N,N',N'-tetramethyluronium (126 mg, 0.33 mmol) was added to acetonitril solution (1 mL) of the intermediate 36 (54 mg), 4-(2-amino-ethyl)morpholine (32 mg, 0.24 mmol), and triethylamine (0.09 mL, 0.67 mmol), and the mixture was stirred at the room temperature. After that, the resulting solution was concentrated under reduced pressure. The residue was purified with column chromatography (dichloromethane/methanol=30/1(v/v)) using silicagel treated with amine to afford the crude colorless oily-product (79 mg).
$^1$H-NMR (300 MHz, CDCl$_3$) δ 8.17 (d, J=7.3 Hz, 1H), 7.83 (s, 1H), 7.63 (d, J=9.5 Hz, 1H), 7.30-7.20 (m, 1H), 7.04 (s, 1H), 6.86 (t, J=6.6 Hz, 1H), 6.15 (br s, 1H), 4.30 (s, 3H), 3.78-3.68 (m, 4H), 3.61-3.53 (m, 2H), 2.65-2.45 (m, 6H).
MS (ESI) m/z: [M+H]$^+$355.
A preparative HPLC system (the purification apparatus A), which was used for the purification in the example compound 1, was used for further purification.

Example Compound 35

Synthesis of 5-(1,3-benzothiazol-2-yl)-1-methyl-N-[2-(morpholin-4-yl)ethyl]-1H-pyrazole-3-carboxamide A DMSO solution (0.7 mL) of the intermediate 17 (100 mg, 0.275 mmol), benzothiazole (31 mg, 0.229 mmol), copper iodide(I) (44 mg, 0.229 mmol), triphenylphosphine (12 mg, 0.046 mmol) and tripotassium phosphate (97 mg, 0.458 mmol) was stirred at 160° C. for 1 hour under the nitrogen atmosphere. The resulting residue was purified with column chromatography (dichloromethane/methanol=10/1(v/v)) and was treated with SCX (strong cation exchange cartridge) in a similar manner to the example compound 1 to afford the crude product 35 (100 mg).
A preparative HPLC system (the purification apparatus A), which was used for the purification in the example compound 1, was used for further purification.
MS (ESI)m/z: [M+H]$^+$372.

Example Compound 36

Synthesis of 5-{5-fluoro1-methyl-1H-pyrrolo[2,3-b]pyridin-2-yl}-1-methyl-N-[2-(morpholin-4-yl)ethyl]-1H-pyrazole-3-carboxamide Methyl iodide (14.2 mg, 0.10 mmol) was added to an acetonitril solution (5 mL) The example compound 29 (30 mg, 0.08 mmol) and caesium carbonate (52 mg, 0.16 mmol). The reaction solution was stirred at 60° C. for 3 hours. After cooling down to the room temperature, the reaction solution was diluted with dichloromethane. After the resulting solution was washed with water and a saturated sodium chloride solution, and was dried over sodium sulfate. After the drying agent was filtered, the filtrate was concentrated under reduced pressure and the crude product (32 mg) was obtained as a yellow amorphous. A preparative HPLC system (the purification apparatus A), which was used for the purification in the example compound 1, was used for further purification.
MS (ESI) m/z: [M+H]$^+$387.

Example Compound 37

5-(5-fluoro-1H-indol-2-yl)-N-{2-[(2R)-2-(hydroxymethyl)pyrrolidin-1-yl]ethyl}-1-methyl-1H-pyrazole-3-carboxamide

Intermediate 37

Synthesis of N-(2,2-dimethoxyethyl)-5-(5-fluoro-1H-indol-2-yl)-1-methyl-1H-pyrazole-3-carboxamide Hexafluorophosphate O-benzotriazole-1-yl-N,N,N',N'-tetramethyluronium (505 mg, 1.33 mmol) was added to an acetonitril solution (10 mL) of the intermediate 10 (230 mg, 0.89 mmol), amino-acetaldehyde diethyl aceta (93 mg, 0.89 mmol), triethylamine (0.50 mL, 3.55 mmol) at the room temperature. The reaction solution was stirred at the room temperature for 16 hours. The reaction solution was diluted with ethyl acetate. After the resulting solution was washed with water, the organic layer was dried over magnesium sulfate. After the drying agent was filtered, the filtrate was concentrated under reduced pressure. The residue was purified with column chromatography (hexane/ethyl acetate=1/2(v/v)) using silicagel to afford the intermediate 37 (307 mg, quantitative) as a white solid.
$^1$H-NMR (300 MHz, CDCl$_3$) δ 9.28 (s, 1H), 7.42-7.39 (m, 1H), 7.32-7.26 (m, 1H), 7.20-7.12 (m, 2H), 7.05-6.98 (m, 1H), 6.68 (d, J=1.5 Hz, 1H), J=5.9 Hz, 1H), 4.11 (s, 3H), 3.64 (t, J=5.9 Hz, 2H), 3.42 (s, 6H).
MS (ESI)m/z: [M−H]$^-$345.

Intermediate 38

Synthesis of 5-(5-fluoro-1H-indol-2-yl)-1-methyl-N-(2-oxoethyl)-1H-pyrazole-3-carboxamide A 2M HCl solution (5 mL) was added to a THF solution (5 mL) of the intermediate 37 (294 mg, 0.85 mmol) and the resulting solution was stirred at 50° C. for 2 hours. After cooling, the reaction solution was neutralized with adding a 2M sodium hydroxide solution (5 mL), and was extracted with ethyl acetate. The obtained organic layer was washed with a saturated sodium chloride solution, and was dried over magnesium sulfate. After the drying agents were filtered, the filtrate was concentrated under reduced pressure to afford the intermediate 38 (300 mg, quantitative) as a white solid. The Intermediate was used for the following reaction without any further purification.
MS (ESI)m/z: [M+H]+301.

Example Compound 37

5-(5-fluoro-1H-indol-2-yl)-N-{2-[(2R)-2-(hydroxymethyl)pyrrolidin-1-yl]ethyl}-1-methyl-1H-pyrazole-3-carboxamide A THF solution of (4.2 mL) the intermediate 38 (30 mg, 0.10 mmol), (R)-(−)-2-pyrrolidinemethanol (15 mg, 0.15 mmol) and acetic acid (0.15 mL) was stirred at the room temperature for 10 minutes. After that, a THF solution (0.2 mL) of sodium triacetoxyborohydride (63 mg, 0.30 mmol) was added to the solution, and the resulting solution was stirred overnight at the room temperature. After the reaction solution was concentrated, the residue was completely dissolved with adding ethyl acetate (0.7 mL) and a 2M sodium hydroxide solution (0.5 mL). After the obtained organic layer was loaded to SCX (strong cation exchange cartridge), washed with methanol (5 mL), and was finally eluted with ammonia-methanol (1M, 4 mL). The crude product obtained by the concentration was purified with a preparative HPLC (the purification apparatus A written in the beginning of EXAMPLES).

MS (ESI) m/z: [M+H]$^+$386.

Examples synthesized by using the similar reaction described above are shown below Example Compound 38

5-(5-fluoro-1H-indol-2-yl)-N-{2-[(3R)-3-(hydroxy-pyrrolidin-1-yl]ethyl}-1-methyl-1H-pyrazole-3-carboxamide Example Compound 39

5-(5-fluoro-1H-indol-2-yl)-N-{2-[(3S)-3-(hydroxypiperidin-1-yl]ethyl}-1-methyl-1H-pyrazole-3-carboxamide Example Compound 40

5-(5-fluoro-1H-indol-2-yl)-1-methyl-N-{2-[(1S,4S)-2-oxa-5-azabicyclo[2.2.1]heptan-5-yl]ethyl}-1H-pyrazole-3-carboxamide Example Compound 41

N-[2-(3,3-difluoroazetidin-1-yl)ethyl]-5-(5-fluoro-1H-indol-2-yl)-1-methyl-1H-pyrazole-3-carboxamide Example Compound 42

5-(5-fluoro-1H-indol-2-yl)-N-{2-[(2S)-2-(hydroxymethyl)pyrrolidin-1-yl]ethyl}-1-methyl-1H-pyrazole-3-carboxamide Example Compound 43

5-(5-fluoro-1H-indol-2-yl)-N-{2-[(3R)-3-fluoropyrrolidin-1-yl]ethyl}-1-methyl-1H-pyrazole-3-carboxamide Example Compound 44

5-(5-fluoro-1H-indol-2-yl)-N-{2-[(3S)-3-fluoropyrrolidin-1-yl]ethyl}-1-methyl-1H-pyrazole-3-carboxamide Example Compound 45

5-(5-fluoro-1H-indol-2-yl)-N-[2-(4-fluoropiperidin-1-yl]ethyl}-1-methyl-1H-pyrazole-3-carboxamide Example Compound 46

5-(5-fluoro-1H-indol-2-yl)-1-methyl-N-[2-(1,4-oxazepam-4-yl)ethyl}-1H-pyrazole-3-carboxamide Example Compound 47

N-[2-(azetidin1-yl)ethyl]-5-(5-fluoro-1H-indol-2-yl)-1-methyl-1H-pyrazole-3-carboxamide

TABLE 4

| Example Compound number | | Amine |
|---|---|---|
| 38 | 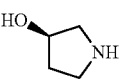 | 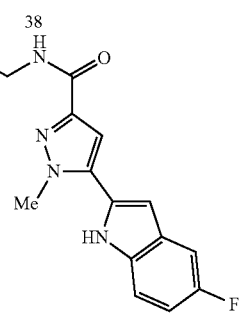 |
| 39 | 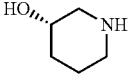 | 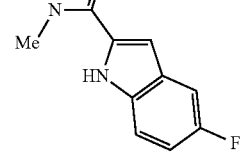 |
| 40 |  |  |
| 41 | 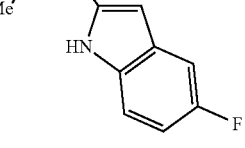 | 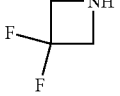 |

TABLE 4-continued

| Example Compound number | Amine |
|---|---|
| 42 | (S)-prolinol (HOCH2-pyrrolidine) |
| 43 | (3S)-3-fluoropyrrolidine |
| 44 | (3R)-3-fluoropyrrolidine |
| 45 | 4-fluoropiperidine |
| 46 | 1,4-oxazepane |
| 47 | azetidine |

TABLE 5

| Example Compound number | MS (ESI) m/z | Example Compound number | MS (ESI) m/z |
|---|---|---|---|
| 38 | [M + H]+ 372 | 39 | [M + H]+ 386 |
| 40 | [M + H]+ 384 | 41 | [M + H]+ 378 |
| 42 | [M + H]+ 386 | 43 | [M + H]+ 374 |
| 44 | [M + H]+ 374 | 45 | [M + H]+ 388 |
| 46 | [M + H]+ 386 | 47 | [M + H]+ 342 |

Alternative Synthetic Method of Example Compound 17

Synthesis of 1-methyl-N-[2-(morpholin-4-yl)ethyl]-5-(quinolin-3-yl)-1H-pyrazole-3-carboxamide According to the similar synthetic method of the intermediate 11 above, tris(dibenzylideneacetone)dipalladium(0) (66 mg, 0.0723 mmol) was added to the 1,4-dioxane (20 mL)-water (3 mL) mixed solution of the intermediate 17 (526 mg, 1.44 mmol), 3-quinolineboronic acid (250 mg, 1.44 mmol), potassium phosphate (458 mg, 2.16 mmol) and of tricyclohexylphosphine (40.4 mg, 0.14 mmol). The reaction solution was stirred at 100° C. overnight (15 hours). The obtained residue was purified with column chromatography (dichloromethane/methanol=20/1(v/v)) using silicagel to afford a white crystal. Then the example compound 17 (204 mg, 39% yield) was obtained as a white crystal by recrystallization from hexane-ethyl acetate.

Examples synthesized by using the similar reaction described above or using the reaction condition in intermediate 8 are shown below:

Example Compound 48

1-methyl-N-[2-(morpholin-4-yl)ethyl]-5-(quinolin-6-yl)-1H-pyrazole-3-carboxamide

Example Compound 49

1-methyl-N-[2-(morpholin-4-yl)ethyl]-5-(quinolin-7-yl)-1H-pyrazole-3-carboxamide

Example Compound 50

1-methyl-N-[2-(morpholin-4-yl)ethyl]-5-(naphthalen-2-yl)-1H-pyrazole-3-carboxamide

Example Compound 51

5-(6-methoxynaphthalen-2-yl)-1-methyl-N-[2-(morpholin-4-yl)ethyl]-1H-pyrazole-3-carboxamide

Example Compound 52

5-(7-methoxynaphthalen-2-yl)-1-methyl-N-[2-(morpholin-4-yl)ethyl]-1H-pyrazole-3-carboxamide

Example Compound 53

5-(1-benzothiophen-3-yl)-1-methyl-N-[2-(morpholin-4-yl)ethyl]-1H-pyrazole-3-carboxamide

Example Compound 54

1-methyl-N-[2-(morpholin-4-yl)ethyl]-5-(quinoxalin-6-yl)-1H-pyrazole-3-carboxamide

TABLE 6

| Example Compound number | Chemical reagent |
|---|---|
| 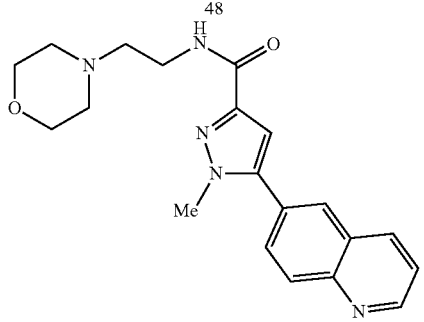 48 | 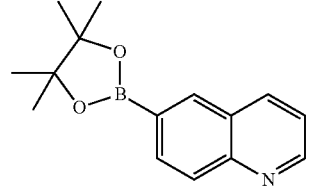 |
| 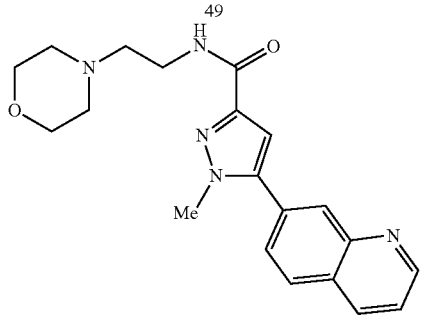 49 | 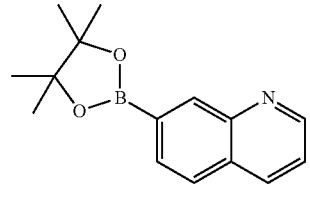 |
| 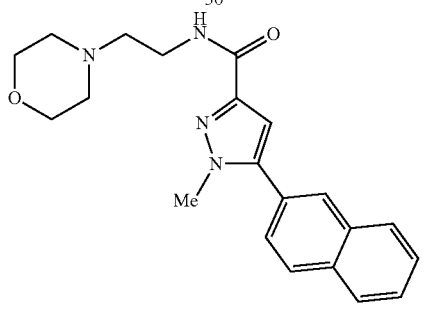 50 | 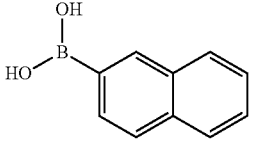 |

TABLE 6-continued
| Example Compound number | Chemical reagent |
|---|---|
| 51 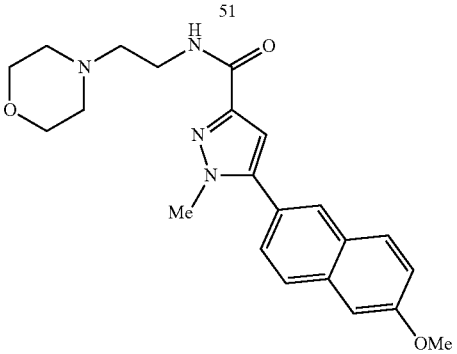 | 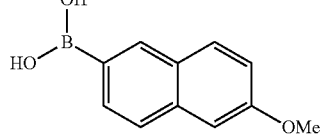 |
| 52 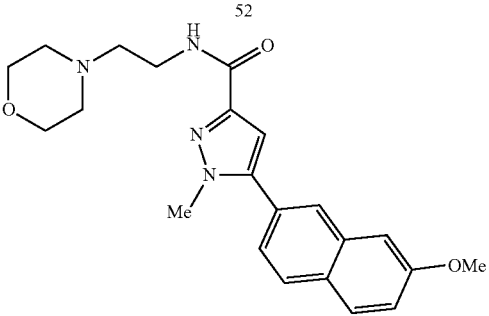 | 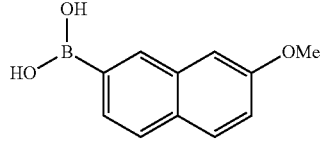 |
| 53 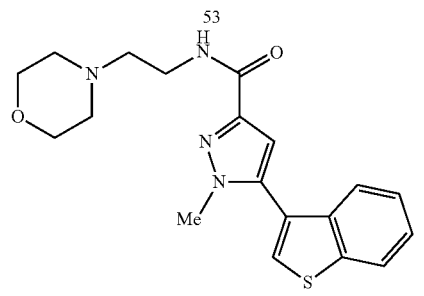 | 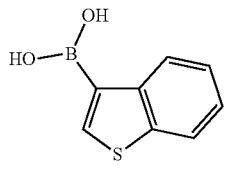 |
| 54 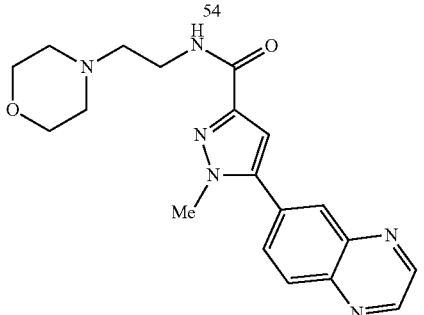 | 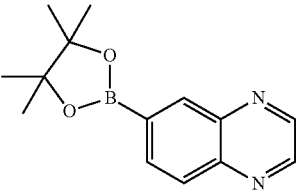 |

TABLE 7

| Example Compound number | MS (ESI) m/z | Example Compound number | MS (ESI) m/z |
|---|---|---|---|
| 48 | [M + H]+ 366 | 49 | [M + H]+ 366 |
| 50 | [M + H]+ 365 | 51 | [M + H]+ 395 |
| 52 | [M + H]+ 395 | 53 | [M + H]+ 371 |
| 54 | [M + H]+ 367 | | |

Synthesis of Example Compound 55
Synthesis of 5-(1H-indol-3-yl)-1-methyl-N-[2-(morpholin-4-yl)ethyl]-1H-pyrazole-3-carboxamide Intermediate 39
Synthesis of 5-[1-(benzenesulfonyl)-1H-indol-3-yl]-1-methyl-N-[2-(morpholin-4-yl)ethyl]-1H-pyrazole-3-carboxamide The intermediate 17 (200 mg, 0.55 mmol), palladium acetate (25 mg, 0.11 mmol), and triphenylphosphine (58 mg, 0.22 mmol) was dissolved in dioxane/toluene solution (3.3/1 (v/v), 5.2 mL) and the resulting mixture was stirred at the room temperature for 10 minutes. After that, 1-(phenylsulfonyl)-3-indoleboronic acid (215 mg, 0.71 mmol), water (1.2 mL), and sodium carbonate (233 mg, 2.20 mmol) was added to the reaction solution, and the resulting mixture was heated at reflux for 16 hours. After cooling, the reaction solution was diluted with ethyl acetate. Sodium sulfate was added to the resulting solution for removing water and the resulting mixture was filtered. After the filtrate was concentrated under reduced pressure, the residue was pretreated with column chromatography (ethyl acetate) using silicagel. After that, the obtained organic layer was loaded to SCX (strong cation exchange cartridge), washed with methanol, and was finally eluted with ammonia-methanol (1M). The eluate was concentrated under reduced pressure to afford the intermediate 39 (271 mg, quantitative) as a crude product. The intermediate was used for the following reaction without any further purification.
MS (ESI) m/z: [M+H]+494.

Example Compound 55

Synthesis of 5-(1H-indol-3-yl)-1-methyl-N-[2-(morpholin-4-yl)ethyl]-1H-pyrazole-3-carboxamide The intermediate 39 (271 mg) was dissolved in methanol (5 mL), and a 2M sodium hydroxide solution (5 mL) was added to the solution, the resulting solution was stirred at 70° C. for 30 minutes. After cooling, water (10 mL) was added to the reaction solution, and the resulting mixture was extracted with dichloromethane (50 mL) three times. After the combined organic layer was dried over magnesium sulfate, the drying agent was filtered, and the filtrate was concentrated under reduced pressure. The residue was purified with column chromatography (dichloromethane/methanol=10/1(v/v)) using silicagel to give the crude product (169 mg) as light brown solid. A preparative HPLC system (the purification apparatus A), which was used for the purification in the example compound 1, was used for further purification.
MS (ESI)m/z: [M+H]+354.

Synthesis of Example Compound 56

1-methyl-5-(1-methyl-1H-indol-3-yl)-N-[2-(morpholin-4-yl)ethyl]-1H-pyrazole-3-carboxamide The example compound 55 (50 mg) was dissolved in acetonitril (1 mL) and cesium carbonate (138 mg, 0.42 mmol) and methyl iodide (0.013 mL, 0.21 mmol) was added to the resulting solution, and the mixture was heated at reflux for 1 hour. After cooling, the insoluble substances were removed by filtration, and the filtrate was concentrated under reduced pressure. The residue was purified with column chromatography (dichloromethane/methanol=10/1(v/v)) using silicagel to afford the crude product (45 mg) as colorless syrup. A preparative HPLC system (the purification apparatus A), which was used for the purification in the example compound 1, was used for further purification.
MS (ESI)m/z: [M+H]+368.

Intermediates and examples synthesized by using the similar reaction described above are shown below:

TABLE 8

| Intermediate/Example Compound number | boronic acid |
|---|---|
| Intermediate 40 [M + H]+ 536 | |

TABLE 8-continued
| Intermediate/Example Compound number | boronic acid |
|---|---|
| Example Compound number 57 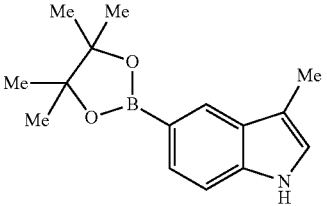 [M + H]+ 368 | 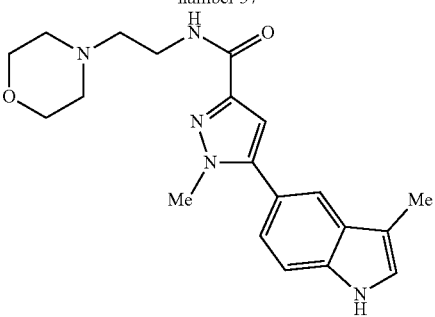 |
| Intermediate 41 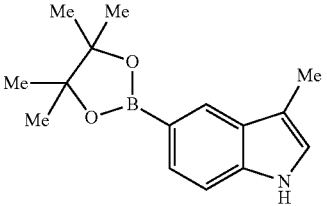 [M + H]+ 354 | 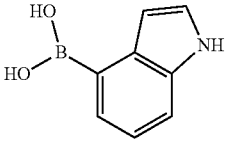 |
| Intermediate 42 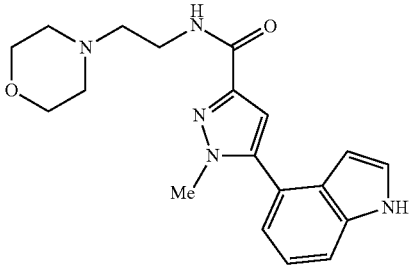 [M + H]+ 495 | 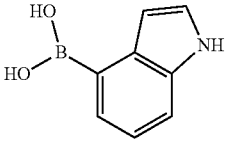 |
| Intermediate 43 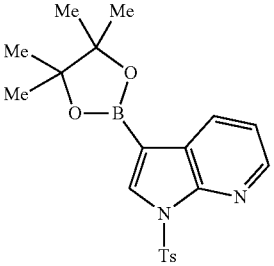 [M + H]+ 538 | 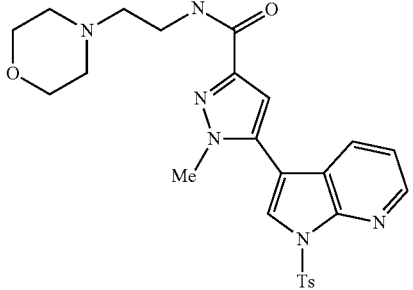 |

TABLE 8-continued

| Intermediate/Example Compound number | boronic acid |
| --- | --- |
| Intermediate 44<br>[M + H]+ 526 | |
| Intermediate 45<br>[M + H]+ 526 | |
| Intermediate 46<br>[M + H]+ 526 | |
| Intermediate 47<br>[M + H]+ 538 | |

TABLE 8-continued

| Intermediate/Example Compound number | boronic acid |
|---|---|
| Intermediate 48 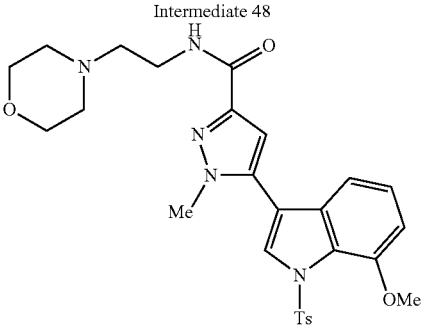 [M + H]+ 538 | 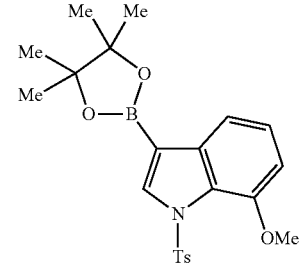 |

Example Compound 57

1-methyl-5-(3-methyl-1H-indol-5-yl)-N-[2-(morpholin-4-yl)ethyl]-1H-pyrazole-3-carboxamide Example Compound 58

1-methyl-5-(2-methyl-1H-indol-5-yl)-N-[2-(morpholin-4-yl)ethyl]-1H-pyrazole-3-carboxamide Example Compound 59

1-methyl-N-[2-(morpholin-4-yl)ethyl]-5-{1H-pyrrolo[2,3-b]pyridin-3-yl}-1H-pyrazole-3-carboxamide Example Compound 60

5-(5-methoxy-1H-indol-3-yl)-1-methyl-N-[2-(morpholin-4-yl)ethyl]-1H-pyrazole-3-carboxamide Example Compound 61

5-(5-fluoro-1H-indol-3-yl)-1-methyl-N-[2-(morpholin-4-yl)ethyl]-1H-pyrazole-3-carboxamide Example Compound 62

5-(1,2-dimethyl-1H-indol-5-yl)-1-methyl-N-[2-(morpholin-4-yl)ethyl]-1H-pyrazole-3-carboxamide Example Compound 63

5-(1,3-dimethyl-1H-indol-5-yl)-1-methyl-N-[2-(morpholin-4-yl)ethyl]-1H-pyrazole-3-carboxamide Example Compound 64

1-methyl-5-{1-methyl-1H-pyrrolo[2,3-b]pyridin-3-yl)}-N-[2-(morpholin-4-yl)ethyl]-1H-pyrazole-3-carboxamide Example Compound 65

5-(5-methoxy1-methyl-1H-indol-3-yl)-1-methyl-N-[2-(morpholin-4-yl)ethyl]-1H-pyrazole-3-carboxamide Example Compound 66

5-(5-fluoro1-methyl-1H-indol-3-yl)-1-methyl-N-[2-(morpholin-4-yl)ethyl]-1H-pyrazol-3-carboxamide Example Compound 67

1-methyl-5-(1-methyl-1H-indol-4-yl)-N-[2-(morpholin-4-yl)ethyl]-1H-pyrazole-3-carboxamide Example Compound 68

5-[1-(2-methoxyethyl)-1H-indol-3-yl]-1-methyl-N-[2-(morpholin-4-yl)ethyl]-1H-pyrazole-3-carboxamide Example Compound 69

5-(1-ethyl1H-indol-3-yl)-1-methyl-N-[2-(morpholin-4-yl)ethyl]-1H-pyrazole-3-carboxamide Example Compound 70

5-(4-fluoro-1H-indol-3-yl)-1-methyl-N-[2-(morpholin-4-yl)ethyl]-1H-pyrazole-3-carboxamide Example Compound 71

5-(6-fluoro-1H-indol-3-yl)-1-methyl-N-[2-(morpholin-4-yl)ethyl]-1H-pyrazole-3-carboxamide Example Compound 72

5-(6-methoxyl H-indol-3-yl)-1-methyl-N-[2-(morpholin-4-yl)ethyl]-1H-pyrazole-3-carboxamide Example Compound 73

5-(7-methoxyl H-indol-3-yl)-1-methyl-N-[2-(morpholin-4-yl)ethyl]-1H-pyrazole-3-carboxamide Example Compound 74

5-[1-(2-methoxyethyl)-2-methyl-1H-indol-5-yl]-1-methyl-N-[2-(morpholin-4-yl)ethyl]-1H-pyrazole-3-carboxamide Example Compound 75

5-[1-(2-hydroxyethyl)-2-methyl-1H-indol-5-yl]-1-methyl-N-[2-(morpholin-4-yl)ethyl]-1H-pyrazole-3-carboxamide Examples synthesized by using the similar reaction described above are shown below: wherein, easily recognized for those skilled in the arts, substituted alkyl halides corresponding the examples can be used instead of methyl iodide.

TABLE 9

| Example compound number |
| --- |
| 57 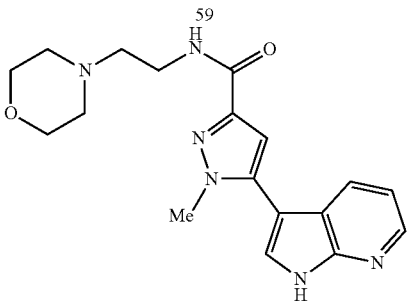 [M + H]+ 368 |
| 58 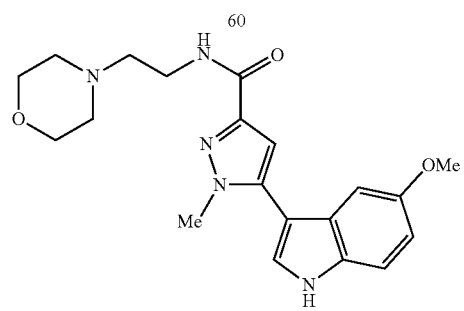 [M + H]+ 368 |

TABLE 9-continued

| Example compound number |
| --- |
| 59 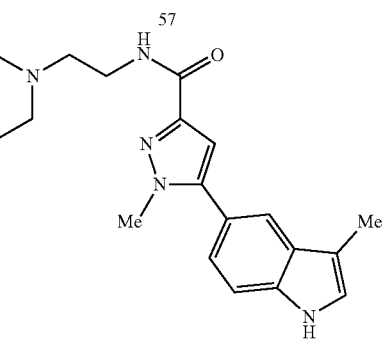 [M + H]+ 355 |
| 60 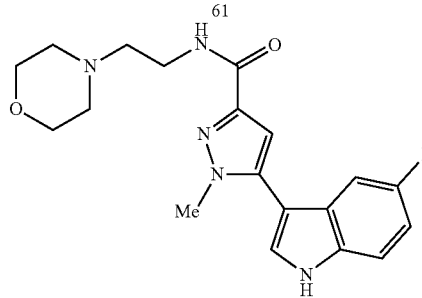 [M + H]+ 384 |
| 61 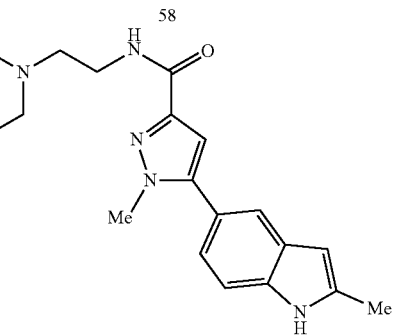 [M + H]+ 372 |
| 62 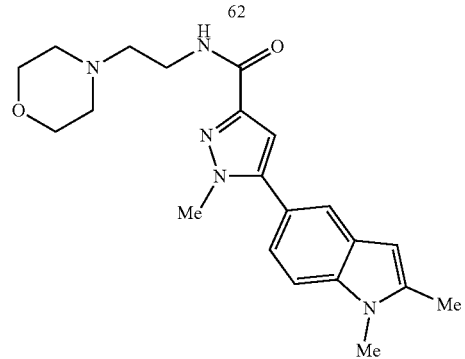 [M + H]+ 382 |

TABLE 9-continued
Example compound number
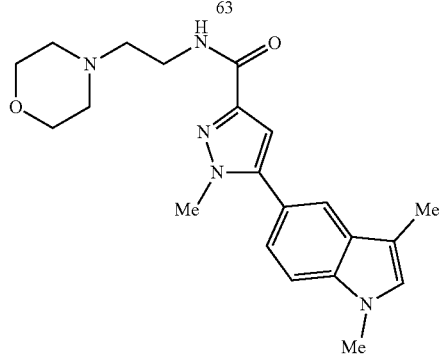
63
[M + H]+
382
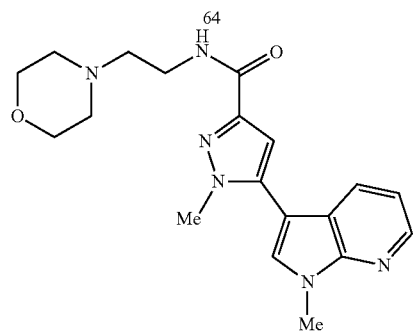
64
[M + H]+
369
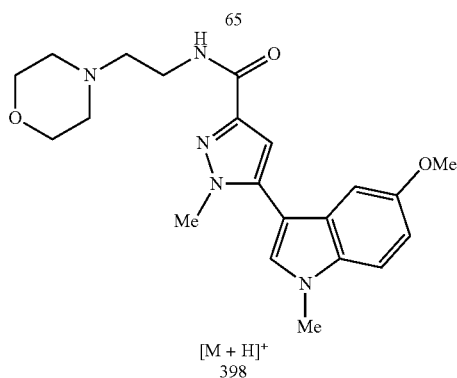
65
[M + H]+
398
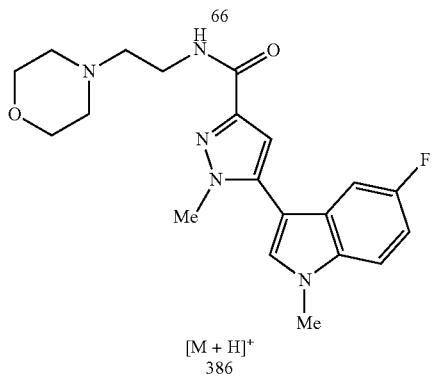
66
[M + H]+
386
TABLE 9-continued
Example compound number
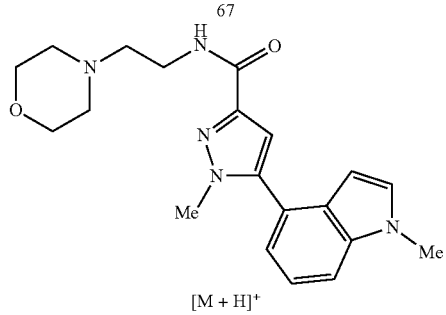
67
[M + H]+
368
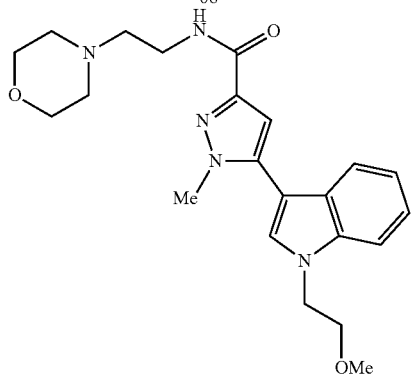
68
[M + H]+
412
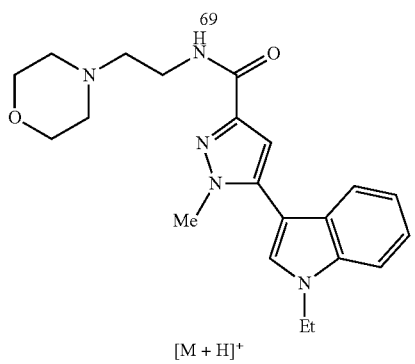
69
[M + H]+
382
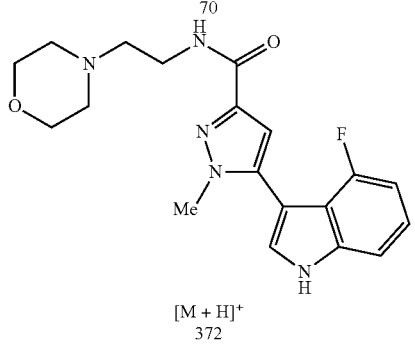
70
[M + H]+
372

TABLE 9-continued

Example compound number

71
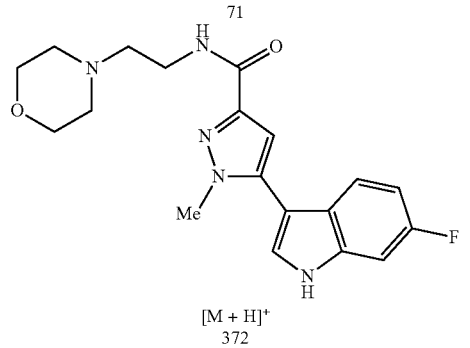
[M + H]+
372

72
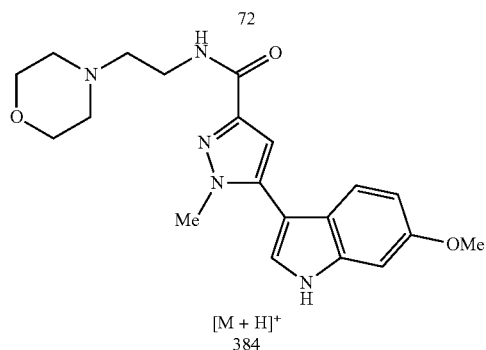
[M + H]+
384

73
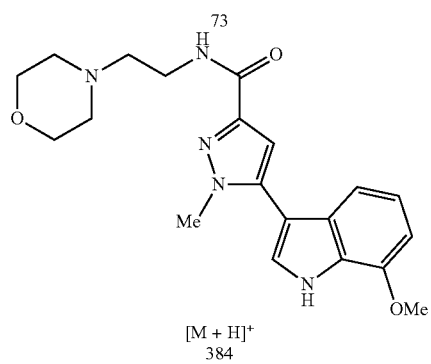
[M + H]+
384

74
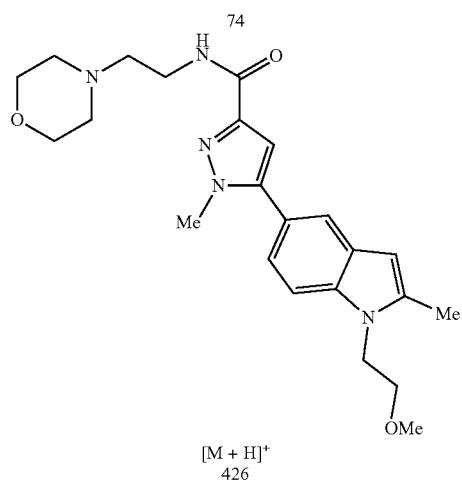
[M + H]+
426

75
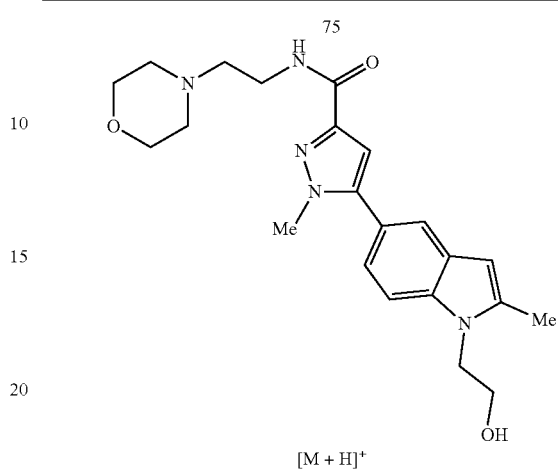
[M + H]+
412

Example Compound 76

Synthesis of 5-(4-methanesulfonyl-1H-indol-2-yl)-1-methyl-N-[2-(morpholin-4-yl)ethyl]-1H-pyrazole-3-carboxamide

Intermediate 49

Synthesis of 1-(benzenesulfonyl)-4-(methylsulfanyl)-1H-indole

Sodium methanethiolate (1300 mg, 18.16 mmol) and a 1N HCl-diethyl ether solution (20 mL) was added in an ice bath to a THF (50 mL) solution of 1-(benzenesulfonyl)-4,5,6,7-tetrahydro-1H-indol-4-one (1250 mg, 4.54 mmol), which was prepared from 4,5,6,7-tetrahydro-1H-4-one in reference to the patent literature (JP-7-247263A), and the mixture was stirred at the room temperature overnight. Then diethylether (30 mL) was added to the mixture. The resulting mixture was washed with a saturated sodium bicarbonate solution (50 mL), and was dried over anhydrous magnesium sulfate. After the drying agent was filtrated, the obtained filtrate was concentrated under reduced pressure to afford an oily-residue. The oily residue was dissolved in toluene (15 mL), and DDQ (1500 mg, 6.81 mmol) was added to the mixture. The mixture was heated at reflux for 2 hours. After cooling, the resulting mixture was concentrated under reduced pressure to afford the crude oily intermediate 49. The obtained crude intermediate 49 was purified with column chromatography (hexane-ethylacetate=10:1(v/v)) using silicagel to afford the intermediate 49 (690 mg, 50% yield) as a white semisolid.

$^1$H-NMR (300 MHz, CDCl$_3$) δ 7.88-7.79 (m, 3H), 7.58 (d, J=4.0 Hz, 1H), 7.57-7.50 (m, 1H), 7.46-7.41 (m, 2H), 7.43-7.24 (m, 1H), 7.08 (d, J=7.3 Hz, 1H), 6.78 (d, J=3.7 Hz, 1H), 3.58 (s, 3H).

MS (ESI) m/z: [M+H]+304.

Intermediate 50

Synthesis of [1-(benzenesulfonyl)-4-(methylsulfanyl)-1H-indol-2-yl]borandiol n-Butyllithium (2.5 mL, 4.12 mmol, 1.65M cyclohexane solution) was added dropwise to a THF (5 mL) solution of diisopropylamine (417 mg, 0.58 mmol) in an ice bath, and the mixture was stirred for 20 minutes, which afforded lithium diisopropylamide. Lithium diisopropylamide prepared above was added in an ice bath dropwise to a THF (25 mL) solution of the intermediate 49 (833 mg, 2.75 mmol) and triisopropylboronic acid ester (620 mg, 3.29 mmol) which was separately prepared. Two hours later, the same amount of lithium diisopropylamide was further added dropwise in an ice bath. After the mixture was stirred in an ice bath for 1 hour, a 1M HCl solution was added to the mixture, and the solution was adjusted to pH3. The resulting solution was extracted with ethyl acetate (25 mL×2), and the combined mixture was dried over anhydrous magnesium sulfate. After the drying agent was filtered, the obtained filtrate was concentrated under the reduced pressure. The obtained residue was purified with column chromatography (hexane/ethyl acetate) using silicagel to afford the crude intermediate 50 (953 mg, 100% yield) as a yellow semisolid.

Intermediate 51

Synthesis of 5-[1-benzenesulfonyl)-4-methylsulfanyl)-1H-indol-2-yl]-1-methyl-N-[2-(morpholin-4-yl)ethyl]-1H-pyrazole-3-carboxamide According to the similar manner to the synthesis of the intermediate 8 in the example compound 1, the intermediate 51 (390 mg, 29% yield) was obtained as a white semisolid from the intermediate 17 (909 mg, 2.50 mmol), the intermediate 50 (953 mg, 2.74 mmol), palladium acetate(II) (56 mg, 0.25 mmol), triphenylphosphine (262 mg, 1.00 mmol), and sodium carbonate (661 mg, 6.24 mmol).

MS (ESI)m/z: [M+H]$^+$539.

Intermediate 52

Synthesis of 5-[1-(benzenesulfonyl)-4-(methanesulfonyl)-1H-indol-2-yl]-1-methyl-N-[2-(morpholin-4-yl)ethyl]-1H-pyrazole-3-carboxamide Oxone-persulfate compound (683 mg, 1.11 mmol) was added to a dioxane/water (8 mL/3 mL) solution of the intermediate 51 (200 mg, 0.37 mmol) at the room temperature. The reaction solution was stirred at the room temperature for 2.5 hours. The reaction solution was dried over anhydrous magnesium sulfate. After the drying agent was filtered, the obtained filtrate was concentrated under reduced pressure to afford the yellow-oily crude intermediate 52 (61 mg, 29% yield).

MS (ESI)m/z: [M+H]$^+$572.

Example Compound 76

Synthesis of 5-(4-methanesulfonyl-1H-indol-2-yl)-1-methyl-N-[2-(morpholin-4-yl)ethyl]-1H-pyrazole-3-carboxamide Tetrabutylammoniumfluoride monohydrate (140 mg, 0.53 mmol) was added to a THF (5 mL) solution of the intermediate 52 (61 mg, 0.11 mmol), and the mixture was heated at reflux for 3 hours. After cooling down to the room temperature, the residue obtained under reduced pressure was purified with SCX (strong cation exchange cartridge) in the similar manner to the example compound 1 to afford the crude product 76 as a yellow solid. Further purification with column chromatography (dichloromethane/methanol=10/1(v/v)) using silicagel to afford the example compound 76 (17 mg, 37% yield) as a yellow solid.

MS (ESI)m/z: [M+H]$^+$432.

Example Compound 77

Synthesis of 5-(4-acetamido-1H-indol-2-yl)-1-methyl-N-[2-(morpholin-4-yl)ethyl]-1H-pyrazole-3-carboxamide

Example Compound 78

Synthesis of 5-(4-methanesulfonamido-1H-indol-2-yl)-1-methyl-N-[2-(morpholin-4-yl)ethyl]-1H-pyrazole-3-carboxamide

Intermediate 55

Synthesis of 5-(1H-4-amino-indol-2-yl)-1-methyl-N-[2-(morpholin-4-yl)ethyl]-1H-pyrazole-3-carboxamide dihydrochloride

Intermediate 53

Synthesis of 1-(tert-butyl)-4-(di-tert-butyl)amino-2-indoleboronic acid n-Butyllithium (0.63 mL, 1.65M, hexane solution) was added dropwise to cooled a THF solution (5 mL) of diisopropylamine (105 mg, 104 mmol) in ice-cold condition for 5 minutes under the nitrogen atmosphere. The resulting mixture was stirred for 20 minutes, which afforded a THF solution of lithium diisopropylamide.

A THF solution of lithium diisopropylamide prepared above was added in an ice bath dropwise to a THF (5 mL) solution of 1-(tert-butyl)-4-(di-tert-butyl)aminoindole (300 mg, 0.694 mmol) and triisopropyl borate (157 mg, 0.832 mmol) which was separately prepared. After the reaction solution was stirred in an ice bath for 1 hour, the solution was adjusted to pH3 with adding a 1M HCl solution. The resulting solution was extracted with ethyl acetate (15 mL×2), and the combined solution was dried over anhydrous magnesium sulfate to afford the crude product 53 of 1-(tert-butyl)-4-(ditert-butyl)amino-2-indoleboronic acid. The crude product was used for the next reaction without any further purification.

Intermediate 54

Synthesis of 5-[1-(tert-butyl)-4-(di-tert-butyl)aminoindol-2-yl]-1-methyl-N-[2-(morpholin-4-yl)ethyl]-1H-pyrazole-3-carboxamide An intermediate 17 (178 mg, 0.49 mmol), palladium acetate (14 mg, 0.063 mmol), and triphenylphosphine (52 mg, 0.20 mmol) were dissolved in a dioxane/toluene solution (3.3/1 (v/v), 5.2 mL), and the mixture was stirred at the room temperature for 10 minutes. After that, 1-(tert-butyl)-4-(di-tert-butyl)amino-2-indoleboronic acid 53 (256 mg, 0.54 mmol), water (5 mL), and sodium carbonate (129 mg, 1.22 mmol) were added to the reaction solution, and the mixture was heated at reflux for 1.5 hours. After cooling, the reaction solution was diluted with ethyl acetate, and sodium sulfate was added to the solution for removing water. Then the resulting solution was filtered. After the filtrate was concentrated under reduced pressure, the product was purified with column chromatography (ethyl acetate) using amine-coated silicagel to afford 5-{1-(tert-butyl)-4-(ditert-butyl)amino-indol-2-yl}-1-methyl-N-[2-(morpholin-4-yl)ethyl]-1H-pyrazole-3-carboxamide 54 and 5-{-4-(ditert-butyl)aminoindol-2-yl}-1-methyl-N-[2-(morpholin-4-yl)ethyl]-1H-pyrazole-3-carboxamide was obtained as the mixture (127 mg, colorless solid). This mixture was not subject to any further isolation and was used for the next reaction.

Intermediate 55

Synthesis of 5-(1H-4-amino-indol-2-yl)-1-methyl-N-[2-(morpholin-4-yl)ethyl]-1H-pyrazole-3-carboxamide dihydrochloride The mixture (127 mg) that contains the intermediate 54 above and a 10% HCl-methanol solution (15 mL) in 100 mL of flask was starred under the nitrogen atmosphere at room temperature for 16 hours. The resulting solution was concentrated under reduced pressure, and 5-(1H-4-aminoindol-2-yl)-1-methyl-N-[2-(morpholin-4-yl)ethyl]-1H-pyrazole-3-carboxamide dihydrochloride salt 55 was obtained (99 mg, quantitative).

$^1$H-NMR (300 MHz, CD$_3$OD) δ 7.50-7.47 (m, 1H), 7.23-7.08 (m, 4H), 4.10 (s, 3H), 4.03-3.99 (m, 2H), 3.87-3.76 (m, 4H), 3.67-3.63 (m, 2H), 3.43-3.40 (m, 2H), 3.29-3.19 (m, 2H). No other protons were observed because of the overlapping with solvent peaks based on CD$_3$OD.

MS (ESI) m/z: [M+H]$^+$369.

Example compounds below are substantially in the same manner as the process F-3 described above, and was prepared under the condition selected from the process F-3.

Example Compound 77

Synthesis of 5-(4-acetamido-1H-indol-2-yl)-1-methyl-N-[2-(morpholin-4-yl)ethyl]-1H-pyrazole-3-carboxamide Example Compound 78

5-(4-methanesulfonamido-1H-indol-2-yl)-1-methyl-N-[2-(morpholin-4-yl)ethyl]-1H-pyrazole-3-carboxamide The example compound 77 and compound 78 in the following table were prepared in the presence of base (triethylamine) in 1,2-dichloroethane solution by using the each reagent (acetyl chloride or acetic anhydride, methanesulfonyl chloride) and the intermediate 55. A preparative HPLC system (the purification apparatus A), which was used for the purification in the example compound 1, was used for further purification.

Example Compound 79

Synthesis of 5-(1-methanesulfonyl-1H-indol-3-yl)-1-methyl-N-[2-(morpholin-4-yl)ethyl]-1H-pyrazole-3-carboxamide Example Compound 80

Synthesis of 5-(1-methanesulfonyl-3-methyl-1H-indol-5-yl)-1-methyl-N-[2-(morpholin-4-yl)ethyl]-1H-pyrazole-3-carboxamide The example compound 79 and compound 80 in the following table were prepared in the presence of base (sodium hydride) in a DMF solution by using the each reagent (methanesulfonyl chloride) and the intermediate 55. A preparative HPLC system (the purification apparatus A), which was used for the purification in the example compound 1, was used for further purification.

The reagents and examples are shown below.

TABLE 10

| Example Compound number | Reagent |
|---|---|
| 77 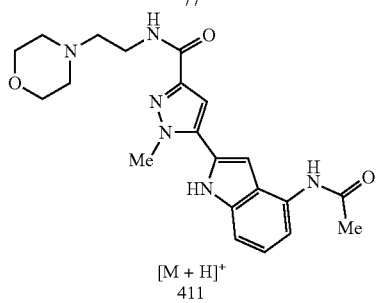 [M + H]$^+$ 411 | 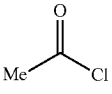 |
| 78 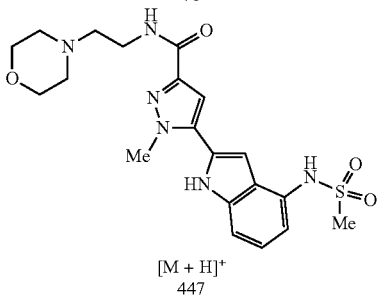 [M + H]$^+$ 447 | 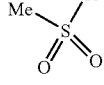 |
| 79 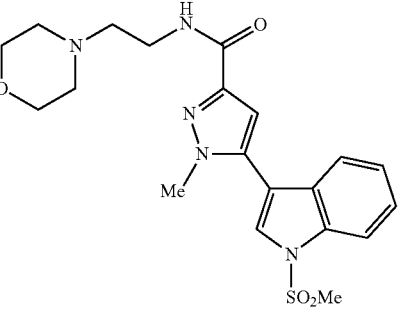 [M + H]$^+$ 432 | 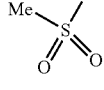 |

TABLE 10-continued

| Example Compound number | Reagent |
|---|---|
| 80 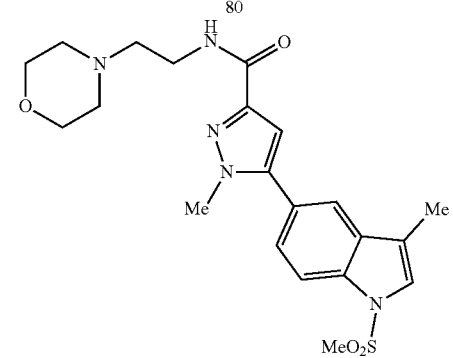 [M + H]+ 446 | 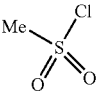 |

Example Compound 81

Synthesis of 1-methyl-5-(3-methyl-1H-indol-1-yl)-N-[2-(morpholin-4-yl)ethyl]-1H-pyrazole-3-carboxamide 3-Methylindole (27 mg, 0.21 mmol), cesium carbonate (179 mg, 0.55 mmol) and copper iodide(I) (52 mg, 0.28 mmol) were added to an intermediate 17 (50 mg, 0.14 mmol) solution dissolved in DMF (1 mL), and the mixture was stirred at 110° C. for 20 hours. After cooling, insoluble substances were removed by filtering, the filtrate was concentrated under reduced pressure. The residue was pretreated with column chromatography (dichloromethane/ethanol (10/1)(v/v)) using silicagel treated with amine and was then loaded to SCX (strong cation exchange cartridge), washed with methanol (10 mL) and was finally eluted with ammonia-methanol (1M, 8 mL). The crude product obtained by the concentration was purified with a preparative HPLC (the purification apparatus A written in the beginning of EXAMPLES).
MS (ESI)m/z: [M+H]$^+$368.

Example Compound 82

Synthesis of 5-{5-cyano-1H-pyrrolo[2,3-b]pyridin-2-yl}-N-[2-(3,3-difluoroazetidin-1-yl)ethyl]-1-methyl-1H-pyrazole-3-carboxamide

Intermediate 56

Synthesis of N-(2,2-diethoxyethyl)-5-iodine-1-methyl-1H-pyrazole-3-carboxamide

According to the similar synthetic method of the example compound 1, triethylamine (3.32 ml, 23.80 mmol) was added to an anhydrous DMF mixture solution (50 mL) of the intermediate 16 (2.00 g, 7.94 mmol), aminoacetaldehyde diethyl acetal (1.27 g, 9.52 mmol) and HBTU (4.52 g, 11.9 mmol), and the mixture was stirred at the room temperature. The resulting residue was purified with column chromatography (hexane/ethylacetateethyl acetate=2:1(v/v)) using silicagel to afford the intermediate 56 (3.84 g) as a light yellow oil.
$^1$H-NMR (300 MHz, CDCl$_3$) δ 6.99 (br s, 1H), 6.94 (s, 1H), 4.61-4.55 (m, 1H), 3.94 (s, 3H), 3.80-3.68 (m, 2H), 3.64-3.50 (m, 4H), 1.23 (t, J=7.0 Hz, 6H).

Intermediate 57

Synthesis of N-[2-(3,3-difluoroazetidin-1-yl)ethyl]-5-iodo-1-methyl-1H-pyrazole-3-carboxamide The reaction mixture of a THF (50 mL) solution of the intermediate 56 (3.84 g, 10.45 mmol) and a 2M HCl solution (25 mL) was stirred at 50° C. for 2 hours. After cooling down the room temperature, the reaction mixture was adjusted to more than pH10 with a saturated sodium bicarbonate solution and was extracted with ethyl acetate twice. The obtained organic layer was washed with a saturated sodium chloride solution, and was dried over sodium hydrochloride. After the drying agent was filtered, the filtrate was concentrated under reduced pressure to afford a light yellow solid. Sodium triacetoxyborohydride (6.64 g, 31.35 mmol) was added in several portions to the mixture of 1,2-dichloroethan (50 mL) of the crude aldehyde intermediate and 3,3-difluoroazetidin monohydrochloride (1.35 g, 10.45 mmol) and ethyl acetate (10 mL). After the resulting mixture was stirred at the room temperature for 15 hours, the reaction mixture was adjusted to more than pH10 with saturated sodium bicarbonate solution, and the solution was extracted with dichloromethanee three times. The resulting organic layer was washed with a saturated sodium chloride solution, and dried over sodium sulfate. After the drying agent was filtered, the filtrate was concentrated under reduced pressure. The obtained residue was purified with column chromatography (dichloromethane/methanol=40/1-30/1(v/v)) using silicagel to afford the intermediate 57 (2.93 g, 76% yield) as a colorless-oil.
$^1$H-NMR (300 MHz, CDCl$_3$) δ 7.05 (br s, 1H), 6.94 (s, 1H), 3.95 (s, 3H), 3.70-3.58 (m, 4H), 3.47-3.39 (m, 2H), 2.80-2.74 (m, 2H).
MS (ESI)m/z: [M+H]$^+$371.

Intermediate 58

Synthesis of N-[2-(3,3-difluoroazetidin-1-yl)ethyl]-1-methyl-5-[2-(trimethylsilyl)ethynyl]-1H-pyrazole-3-carboxamide According to the same synthetic method of the intermediate 18 described in the example compound 22, triethylamine (3.46 mL, 24.86 mmol) was added to an anhydrous THF solution (30 mL) of the intermediate 57 (2.30 g, 6.21 mmol), trimethylsilylacetylene (1.32 mL, 9.32 mmol), copper(I) iodide (118 mg, 0.621 mmol) and dichlorobis(acetonitrile) palladium (II) chloride (436 mg, 0.621 mmol), and the resulting mixture was stirred at the room temperature for 1.5 hours. After the regular treatment, the residue was purified with column chromatography (hexane/ethyl acetate=3: 2-1:1(v/v)) using silicagel to afford the intermediate 58 (1.76 g, 83% yield) as a yellowish brown-oil. And the resulting intermediate 58 was used for the next step without getting any physical data.

Intermediate 59

Synthesis of N-[2-(3,3-difluoroazetidin-1-yl)ethyl]-5-ethynyl1-methyl-1H-pyrazole-3-carboxamide A methanol mixture (30 mL) of the intermediate 58 (1.76 g, 5.17 mmol) and potassium carbonate (107 g, 7.75 mmol) was stirred at the room temperature for 2 hours. After the reaction was completed, potassium carbonate was filtered. The filtrate was concentrated under reduced pressure. The resulting residue was diluted with dichloromethanee again, and was washed with water followed by a saturated sodium chloride solution. Then the solution was dried over sodium sulfate. After the drying agent was filtered, the filtrate was concentrated under reduced pressure. The resulting residue was purified with column chromatography (hexane/ethyl acetate=1:2 (v/v)) using silicagel to afford the intermediate 59 (1.32 g, 95% yield) as a light yellow solid.

$^1$H-NMR (300 MHz, CDCl$_3$) δ 7.12 (br s, 1H), 6.95 (s, 1H), 3.96 (s, 3H), 3.70-3.54 (m, 5H), 3.48-3.40 (m, 2H), 2.82-2.74 (m, 2H).

MS (ESI) m/z: [M+H]$^+$269.

Intermediate 60

Synthesis of 5-[2-(2-amino-5-cyanopyridin-3-yl)ethynyl]-N-[2-(3,3-difluoroazetidin-1-yl)ethyl]-1-methyl-1H-pyrazole-3-carboxamide According to the synthetic method of the intermediate 20, the intermediate 59 (300 mg, 1.12 mmol) and 2-amino-3-iode-5-cyanopyridine (329 mg, 1.34 mmol) were heated under starring at 85° C. for 14 hours, and the intermediate 60 (29.0 mg, 6.7% yield) was obtained as a light yellow solid.

MS (ESI)m/z: [M+H]$^+$386, [M−H]$^-$384.

Example Compound 82

Synthesis of 5-{5-cyano-1H-pyrrolo[2,3-b]pyridin-2-yl}-N-[2-(3,3-difluoroazetidin-1-yl)ethyl]-1-methyl-1H-pyrazole-3-carboxamide According to the similar method for the synthetic process of the example compound 22, the example compound 82 (21 mg, 72% yield) was obtained as a light yellow solid from the intermediate 60 (29 mg, 0.075 mmol).

$^1$H-NMR (300 MHz, DMSO-d$_6$) δ 12.85 (br s, 1H), 8.68 (d, J=2.2 Hz, 1H), 8.59 (d, J=2.2 Hz, 1H), 8.20-8.12 (m, 1H), 7.23 (s, 1H), 7.04 (s, 1H), 4.14 (s, 3H), 3.68-3.53 (m, 4H), 3.31-3.20 (m, 2H), 2.73-2.63 (m, 2H)

MS (ESI) m/z: [M+H]$^+$355, [M−H]$^-$353.

Example Compound 83

Synthesis of N-[2-(3,3-difluoroazetidin-1-yl)ethyl]-1-methyl-5-{1H-pyrrolo[2,3-b]pyridin-2-yl}-1H-pyrazole-3-carboxamide Intermediate 61

Synthesis of 5-[2-(2-aminopyridin-3-yl)ethynyl]-N-[2 (3,3-difluoroazetidin-1-yl)ethyl]-1-methyl-1H-pyrazole-3-carboxamide According to the synthetic method of the intermediate 18, the intermediate 59 (250 mg, 1.12 mmol) and 3-iode-2-aminopyridine (226 mg, 1.03 mmol) were stirred at the room temperature for 3 hours to afford the intermediate 61 (50.3 mg, 15% yield) as a light yellow solid.

MS (ESI)m/z: [M+H]$^+$361.

Example Compound 83

Synthesis of N-[2-(3,3-difluoroazetidin-1-yl)ethyl]-1-methyl-5-{1H-pyrrolo[2,3-b]pyridin-2-yl}-1H-pyrazole-3-carboxamide According to the similar method for synthetic process of the example compound 22, the example compound 83 (37.9 mg, 75% yield) was obtained as a light yellow solid from the intermediate 61 (50 mg, 0.075 mmol).

$^1$H-NMR (300 MHz, DMSO-d$_6$) δ 12.19 (br s, 1H), 8.31-8.26 (m, 1H), 8.15-8.08 (m, 1H), 8.05-7.98 (m, 1H), 7.18-7.08 (m, 2H), 6.89 (s, 1H), 4.12 (s, 3H), 3.66-3.54 (m, 4H), 3.30-3.20 (m, 2H), 2.72-2.63 (m, 2H).

MS (ESI)m/z: [M+H]$^+$361, [M−H]$^-$359.

Example Compound 84

Synthesis of 5-{6-fluoroimidazo[1,2-a]pyridin-2-yl}-1-methyl-N-[2-(morpholin-4-yl)ethyl]-1H-pyrazole-3-carboxamide Intermediate 62

Synthesis of ethyl 5-{6-fluoroimidazo[1,2-a]pyridin-2-yl}-1-methyl-1H-pyrazol-3-carboxylate According to the similar synthetic method of the intermediate 35 in the example compound 34, a methanol solution (2 mL) of the intermediate 34 (114 mg, 0.41 mmol) and 2-amino-5-fluoropyridine (39 mg, 0.41 mmol) was heated under starring for 20 hours. The residue was purified with column chromatography (hexane/ethyl acetate=1/3(v/v)) using silicagel to afford the intermediate 62 (101 mg, 48% yield) as a light yellow solid.

$^1$H-NMR (300 MHz, CDCl$_3$) δ 8.11-8.09 (m, 1H), 7.81 (s, 1H), 7.65-7.60 (m, 1H), 7.21-7.14 (m, 1H), 7.07 (s, 1H), 4.43 (t, J=7.3 Hz, 2H), 4.33 (s, 3H), 1.42 (t, J=7.3 Hz, 3H).

MS (ESI) m/z: [M+H]$^+$289.

Intermediate 63

Synthesis of 5-{6-fluoroimidazo[1,2-a]pyridin-2-yl}-1-methyl-1H-pyrazol-3-carboxylic acid According to the similar synthetic method of the intermediate 36 in the example compound 34, a 2M sodium hydroxide solution (0.175 mL, 0.350 mmol) was added to a methanol solution (5 mL) of the intermediate 62 (101 mg, 0.350 mmol), and the resulting mixture was stirred at 70° C. for 1 hour. After neutralization with a 2M HCl solution, the intermediate 63 (67 mg, 73% yield) was obtained as a white crystal. The intermediate was used for the following reaction without any further purification.

$^1$H-NMR (300 MHz, DMSO-d$_5$) δ 8.75 (br s, 1H), 8.38 (s, 1H), 8.23 (s, 1H), 7.70-7.65 (m, 1H), 7.39-7.33 (m, 1H), 7.06 (s, 1H), 4.24 (s, 3H).

MS (ESI)m/z: [M+H]$^+$261.

Example Compound 84

Synthesis of 5-{6-fluoroimidazo[1,2-a]pyridin-2-yl}-1-methyl-N-[2-(morpholin-4-yl)ethyl]-1H-pyrazole-3-carboxamide According to the similar synthetic method of the example compound 1, the crude example compound 84 (52.3 mg, 54% yield) was obtained as a white crystal from the intermediate 63 (67 mg, 0.257 mmol) and 4-(2-aminoethyl)morpholine (36.9 mg, 0.283 mmol). A preparative HPLC system (the purification apparatus A), which was used for the purification in the example compound 1, was used for further purification.
MS (ESI)m/z: [M+H]$^+$373.

Example Compound 85

Synthesis of 5-{7-fluoroimidazo[1,2-a]pyridin-2-yl}-1-methyl-N-[2-(morpholin-4-yl)ethyl]-1H-pyrazole-3-carboxamide Intermediate 64

Synthesis of ethyl 5-{7-fluoroimidazo[1,2-a]pyridin-2-yl}-1-methyl-1H-pyrazol-3-carboxylate According to the similar synthetic method of the intermediate 35 in the example compound 34, a methanol solution (2 mL) of the intermediate 34 (114 mg, 0.41 mmol) and 2-amino-4-fluoropyridine (39 mg, 0.41 mmol) was heated under starring for 20 hours. Then the residue was purified with column chromatography (hexane/ethyl acetate=1/3(v/v)) using silicagel to afford the intermediate 64 (120 mg, 57% yield) as a light yellow solid.
$^1$H-NMR (300 MHz, CDCl$_3$) δ 8.10 (br s, 1H), 7.81 (s, 1H), 7.65-7.60 (m, 1H), 7.22-7.15 (m, 1H), 7.07 (s, 1H), 4.46-4.40 (t, J=7.3 Hz, 2H), 4.33 (s, 3H), 1.42 (t, J=7.3 Hz, 3H).
MS (ESI)m/z: [M+H]$^+$289.

Intermediate 65

Synthesis of 5-{7-fluoroimidazo[1,2-a]pyridin-2-yl}-1-methyl-1H-pyrazol-3-carboxylic acid According to the similar synthetic method of the intermediate 36 in the example compound 34, a 2M sodium hydroxide solution (0.21 mL, 0.416 mmol) was added to a methanol solution (5 mL) of the intermediate 64 (120 mg, 0.416 mmol), and the resulting mixture was stirred at 70° C. for 1 hour. After neutralization with a 2M HCl solution, the intermediate 65 (67 mg) was obtained as a white crystal. The intermediate was used for the following reaction without any further purification.
$^1$H-NMR (300 MHz, DMSO-d$_6$) δ 8.81-8.79 (m, 1H), 8.41 (s, 1H), 7.75-7.70 (m, 1H), 7.46-7.39 (m, 1H), 7.07 (s, 1H), 4.23 (s, 3H).
MS (ESI)m/z: [M+H]$^+$261.

Example Compound 85

Synthesis of 5-{7-fluoroimidazo[1,2-a]pyridin-2-yl}-1-methyl-N-[2-(morpholin-4-yl)ethyl]-1H-pyrazole-3-carboxamide According to the similar synthetic method of the example compound 1, the crude example compound 85 (102 mg) was obtained as a white crystal from the intermediate 65 (67 mg, 0.257 mmol) and 4-(2-aminoethyl)morpholine (36.9 mg, 0.283 mmol). A preparative HPLC system (the purification apparatus A), which was used for the purification in the example compound 1, was used for further purification.
MS (ESI)m/z: [M+H]$^+$373.

Example Compound 86

Synthesis of 5-{6-cyanoinnidazo[1,2-a]pyridin-2-yl}-1-methyl-N-[2-(morpholin-4-yl)ethyl]-1H-pyrazole-3-carboxamide Intermediate 66

Synthesis of ethyl 5-{6-bromoimidazo[1,2-a]pyridin-2-yl}-1-methyl-1H-pyrazol-3-carboxylate According to the similar synthetic method of the intermediate 35 in the compound 34, an ethanol solution (10 mL) of the intermediate 34 (235 mg, 0.854 mmol) and 2-amino-5-bromopyridine (148 mg, 0.854 mmol) was heated at reflux for 20 hours, and then the residue was purified with column chromatography (hexane/ethyl acetate=1/4(v/v) dichloromethane/methanol=30/1(v/v)) using silicagel to afford the intermediate 66 (106 mg, 36% yield) was obtained as a light yellow solid.
$^1$H-NMR (300 MHz, CDCl$_3$) δ 8.32 (s, 1H), 7.77 (s, 1H), 7.56-7.53 (m, 1H), 7.32-7.27 (m, 1H), 7.09-7.08 (m, 1H), 4.4, 4-4.39 (m, 2H), 4.34-4.33 (m, 3H), 1.42 (t, J=7.3 Hz, 3H)
MS (ESI)m/z: [M+H]$^+$349 & 351.

Intermediate 67

Synthesis of 5-{6-bromoimidazo[1,2-a]pyridin-2-yl}-1-methyl-1H-pyrazol-3-carboxylic acid According to the similar synthetic method of the intermediate 36 in the example compound 34, a 2M sodium hydroxide solution (0.304 mL, 0.608 mmol) was added to a methanol solution (15 mL) of the intermediate 66 (106 mg, 0.304 mmol), and the resulting mixture was stirred at 70° C. for 1 hour. After neutralization with 2M HCl solution, the intermediate 67 (66.7 mg) was obtained as white solid. The intermediate was used for the following reaction without any further purification.
$^1$H-NMR (300 MHz, DMSO-d$_6$) δ 8.93 (s, 1H), 8.38 (s, 1H), 7.65 (d, J=10.4 Hz, 1H), 7.50 (d, J=10.4 Hz, 1H), 7.10 (s, 1H), 4.23 (s, 3H)
MS (ESI)m/z: [M+H]$^+$321 & 323.

Intermediate 68

Synthesis of 5-{6-bromoimidazo[1,2-a]pyridin-2-yl}-1-methyl-N-[2-(morpholin-4-yl)ethyl]-1H-pyrazole-3-carboxamide According to the similar synthetic method of the example compound 1, the crude intermediate 68 (77 mg, 0.078 mmol) was obtained from the intermediate 67 (67 mg, 0.209 mmol) and 4-(2-aminoethyl)morpholine (29.9 mg, 0.23 mmol). Then, the residue was purified with SCX, and intermediate 68 (74.9 mg, 83% yield) was obtained as white solid.
MS (ESI)m/z: [M+H]$^+$433 & 435.

Example Compound 86

Synthesis of 5-{6-cyanoimidazo[1,2-a]pyridin-2-yl}-1-methyl-N-[2-(morpholin-4-yl)ethyl]-1H-pyrazole-3-carboxamide An anhydrous DMF mixture (4 mL) of the intermediate 68 (74.9 mg, 0.173 mmol) and zinc cyanide (12.5 mg, 0.107 mmol) and tetrakis(triphenylphosphine)palladium (20.0 mg, 0.017 mmol) was stirred at 100° C. for 20 hours. After cooling down to the room temperature, water was added to the reaction solution, and the resulting mixture was extracted with ethyl acetate/toluene (9/1) solution. As most of the compounds were transferred to aqueous layer, aqueous layer was concentrated under reduced pressure again. The resulting solid residue was fractionated with a small amount of methanol. The obtained solid was dried under reduced pressure to afford the crude example compound 86 (58.0 mg, 88% yield) as a white solid. A preparative HPLC system (the purification apparatus A), which was used for the purification in the example compound 1, was used for further purification.

MS (ESI)m/z: [M+H]$^+$380, [M−H]$^-$378.

Example Compound 87

Synthesis of N-[2-(3,3-difluoroazetidin-1-yl)ethyl]-1-methyl-5-(quinolin-3-yl)-1H-pyrazole-3-carboxamide According to the similar synthetic method for the intermediate 11 in the example compound 17, 1,4-dioxane solution of (10 mL) the intermediate 57 (224 mg, 0.605 mmol) and 3-quinolineboronic acid (122 mg, 0.666 mmol) was heated under starring at 100° C. for 15 hours, the resulting residue was purified with column chromatography (dichloromethane/methanol=30/1-20/1(v/v)) using silicagel to afford the example compound 81 (181 mg, 80% yield) as the light brown solid. The example compound (181 mg) was purified by recrystallization from ethyl acetate and hexane solution to afford the example compound 87 (121 mg).

$^1$H-NMR (300 MHz, CDCl$_3$) δ 9.00-8.97 (m, 1H), 8.23-8.14 (m, 2H), 7.93-7.77 (m, 2H), 7.69-7.60 (m, 1H), 7.19 (br s, 1H), 7.01 (s, 1H), 4.00 (s, 3H), 3.73-3.61 (m, 4H), 3.54-3.45 (m, 2H), 2.86-2.78 (m, 2H).

MS (ESI)m/z: [M+H]$^+$372.

Example Compound 88

Synthesis of 5-{7-cyanoimidazo[1,2-a]pyridin-2-yl}-1-methyl-N-[2-(morpholin-4-yl)ethyl]-1H-pyrazole-3-carboxamide

Intermediate 69

Synthesis of 5-acetyl1-methyl-1H-pyrazol-3-carboxylic acid

According to the similar synthetic method for the intermediate 16 in the example compound 22, a 2M sodium hydroxide solution (2.55 mL, 5.10 mmol) was added to a methanol solution (12 mL) of the intermediate 33 (500 mg, 2.55 mmol), and the resulting mixture was stirred at the room temperature for 16 hours. After neutralization with a 2M HCl solution, the residue was washed with cool water to afford the intermediate 69 (220 mg, 51% yield) as a white solid.

MS (ESI)m/z: [M+H]$^+$169, [M−H]$^-$167.

Intermediate 70

Synthesis of 5-acetyl N-(2,2-diethoxyethyl)-1-methyl-1H-pyrazole-3-carboxamide

According to the similar synthetic method for the intermediate 56 in the example compound 82, triethylamine (397 mg, 3.93 mmol) was added to anhydrous DMF mixed solution (5 mL) of the intermediate 69 (220 mg, 1.31 mmol) and aminoacetaldehyde diethyl acetal (192 mg, 1.44 mmol), HBTU (595 mg, 1.57 mmol). The resulting mixture was stirred at the room temperature for 3 hours. After the regular treatment, the resulting residue was purified with column chromatography (hexane/ethyl acetate=2/1(v/v)) using silicagel to afford the intermediate 70 (351 mg, 95% yield) as a white solid.

MS(ESI)m/z: [M−H]$^-$282.27.

Intermediate 71

Synthesis of 5-(2-bromoacetyl)-N-(2,2-diethoxyethyl)-1-methyl-1H-pyrazole-3-carboxamide According to the similar synthetic method of the intermediate 34 in Example compound 34, phenyltrimethylammonium bromide (466 mg, 1.24 mmol) was added to a THF solution (5 mL) of the intermediate 70 (351 mg, 1.24 mmol), the resulting mixture was stirred at the room temperature. After the regular treatment, the obtained residue was purified with column chromatography (hexane/ethyl acetate=3/1(v/v)) using silicagel to afford the intermediate 71 (223 mg, 50% yield) as a white solid.

MS (ESI)m/z: [M+H]$^+$362 & 364, [M−H]$^-$360 & 362.

Intermediate 72

Synthesis of 5-{7-cyanoimidazo[1,2-a]pyridin-2-yl}-N-(2,2-diethoxyethyl)-1-methyl-1H-pyrazole-3-carboxamide According to the similar synthetic method for the intermediate 35 in the example compound 34, an ethanol solution (10 mL) of the intermediate 71 (222.9 mg, 0.615 mmol) and 2-amino-4-cyanopyridine (73.3 mg, 0.615 mmol) was heated under starring for 15 hours. The residue was purified with column chromatography (dichloromethane/methanol=30/1 (v/v)) using silicagel to afford the intermediate 72 (174.1 mg, 74% yield) as a light yellow solid.

MS (ESI)m/z: [M+H]$^+$337.

Example Compound 88

Synthesis of 5-{7-cyanoimidazo[1,2-a]pyridin-2-yl}-1-methyl-N-[2-(morpholin-4-yl)ethyl]-1H-pyrazole-3-carboxamide According to the similar synthetic method of the intermediate 57 in the example compound 82, the reaction mixture of a THF solution (5 mL) of the intermediate 72 (174.1 mg, 0.455 mmol) and a 2M HCl solution (2.5 mL) was stirred at 50° C. for 1 hour. After cooling down to the room temperature, the reaction solution was adjusted to more than pH10 with a 2M sodium hydroxide solution (2.5 mL), and the resulting solution was extracted with ethyl acetate. The obtained organic layer was washed with a saturated sodium chloride solution, and the solution was dried over sodium sulfate. After the drying agent was filtered, the filtrate was concentrated under reduced pressure, and a light yellow solid was obtained. Sodium triacetoxyborohydride (289.3 mg, 1.365 mmol) was added to the mixture of the crude aldehyde intermediate and 1,2-dichloroethane (5 mL) of morpholine (39.2 mg, 0.455 mmol) and acetic acid (1 mL) at the room temperature. After the resulting mixture was stirred at the room temperature for 15 hours, the reaction mixture was adjusted to more than pH10 with a sodium bicarbonate solution, and the solution was extracted with dichloromethane three times, the obtained organic layer was washed with a saturated sodium chloride solution, and was dried over sodium sulfate. After the drying agent was filtered, the filtrate was concentrated under reduced pressure. The residue was purified with column chromatography(dichloromethane/methanol=30/1-10/1 (v/v)) using silicagel. Then, Example compound 88 (7 mg, 4% yield) was obtained as light orange solid. MS (ESI)m/z: [M+H]$^+$380.

The lists of intermediates for synthesizing the example compound are shown in the following table 11-1 to 11-4.

TABLE 11-1

| Intermediate number | Structure |
|---|---|
| 2 | 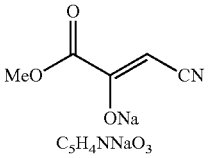 C$_5$H$_4$NNaO$_3$ |
| 3 | MeNHNH$_2$·H$_2$SO$_4$ |
| 4 | 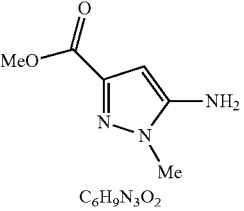 C$_6$H$_9$N$_3$O$_2$ |
| 5 | 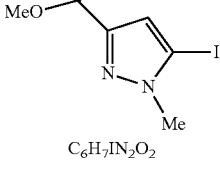 C$_6$H$_7$IN$_2$O$_2$ |
| 6 | 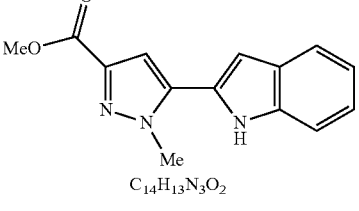 C$_{14}$H$_{13}$N$_3$O$_2$ |
| 7 | 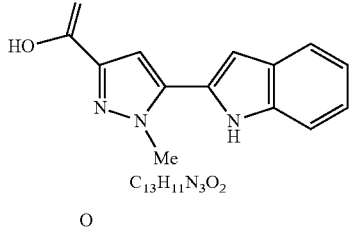 C$_{13}$H$_{11}$N$_3$O$_2$ |
| 8 | 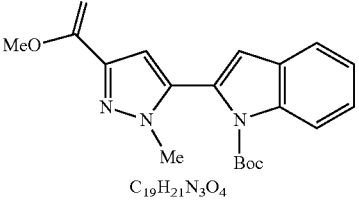 C$_{19}$H$_{21}$N$_3$O$_4$ |

TABLE 11-1-continued

| Intermediate number | Structure |
|---|---|
| 9 | 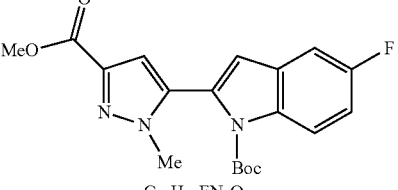 C$_{19}$H$_{20}$FN$_3$O$_4$ |
| 10 | 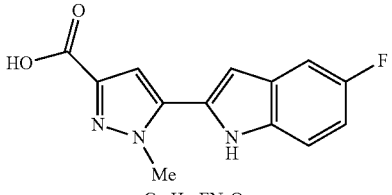 C$_{13}$H$_{10}$FN$_3$O$_2$ |
| 11 | 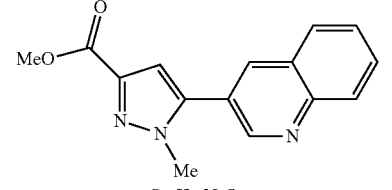 C$_{15}$H$_{13}$N$_3$O$_2$ |
| 12 | 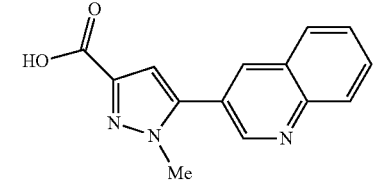 C$_{14}$H$_{11}$N$_3$O$_2$ |
| 13 | 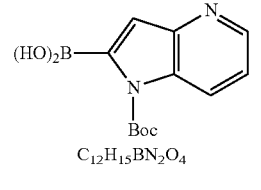 C$_{12}$H$_{15}$BN$_2$O$_4$ |
| 14 | 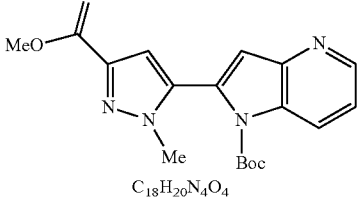 C$_{18}$H$_{20}$N$_4$O$_4$ |
| 15 | 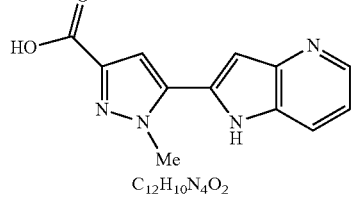 C$_{12}$H$_{10}$N$_4$O$_2$ |

TABLE 11-1-continued
| Intermediate number | Structure |
|---|---|
| 16 | 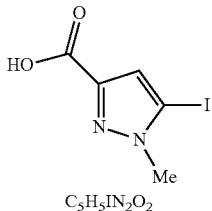<br>$C_5H_5IN_2O_2$ |
| 17 | 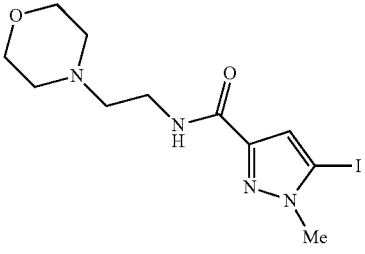<br>$C_{11}H_{17}IN_4O_2$ |
| 18 | 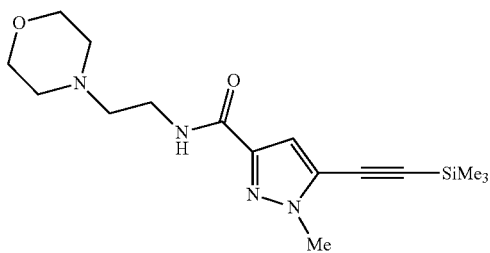<br>$C_{16}H_{26}N_4O_2Si$ |
| 19 | 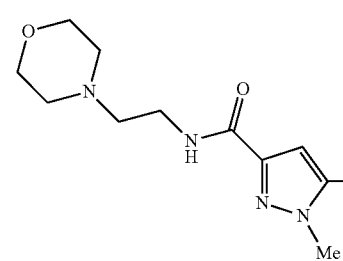<br>$C_{13}H_{18}N_4O_2$ |
TABLE 11-2
| Intermediate number | Structure |
|---|---|
| 20 | 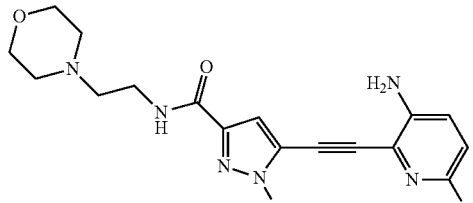<br>$C_{19}H_{24}N_6O_2$ |
TABLE 11-2-continued
| Intermediate number | Structure |
|---|---|
| 21 | 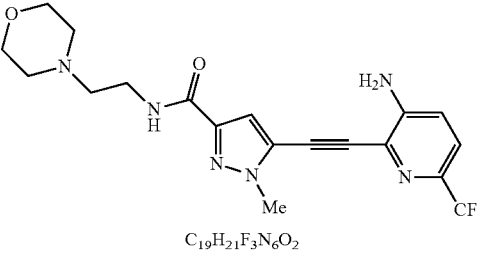<br>$C_{20}H_{26}N_6O_2$ |
| 22 | 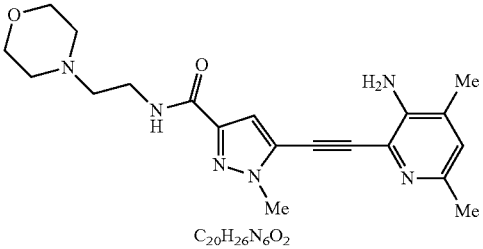<br>$C_{18}H_{22}N_6O_2$ |
| 23 | 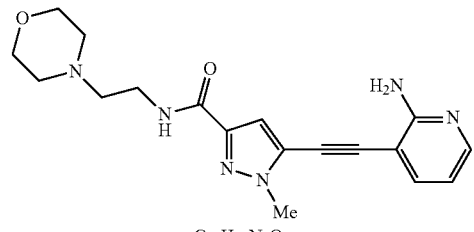<br>$C_{17}H_{21}N_7O_2$ |
| 24 | 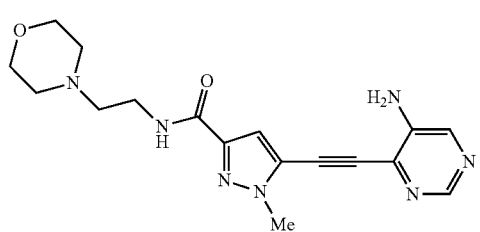<br>$C_{17}H_{21}N_7O_2$ |
| 25 | 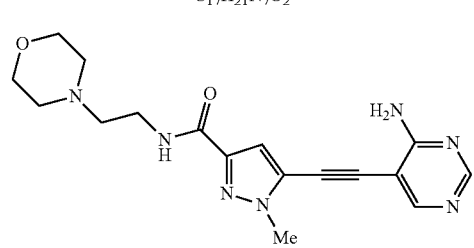<br>$C_{19}H_{21}F_3N_6O_2$ |
| 26 | 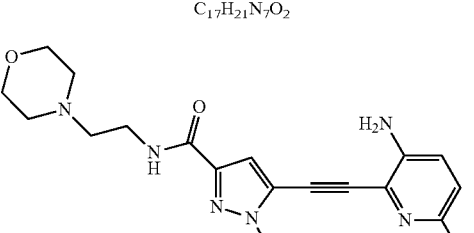<br>$C_{19}H_{24}N_6O_2$ |

TABLE 11-2-continued
| Intermediate number | Structure |
|---|---|
| 27 | 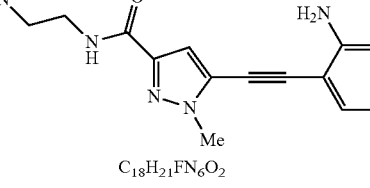 C_{18}H_{21}FN_6O_2 |
| 28 | 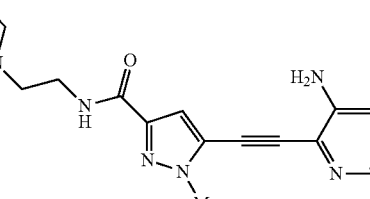 C_{19}H_{21}N_7O_2 |
| 29 | 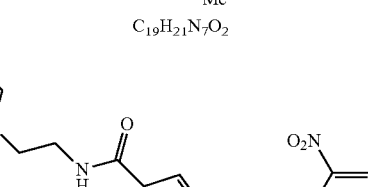 C_{18}H_{19}FN_6O_4 |
| 30 | 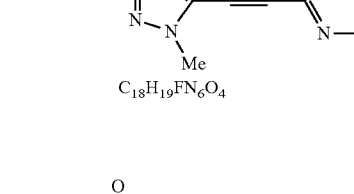 C_{18}H_{21}FN_6O_2 |
| 31 | 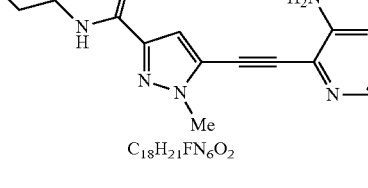 C_{17}H_{21}N_7O_2 |
| 32 | 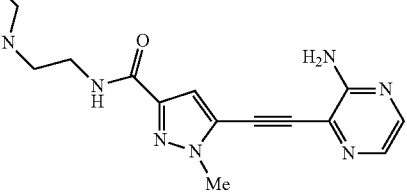 C_{19}H_{21}N_7O_2 |
TABLE 11-2-continued
| Intermediate number | Structure |
|---|---|
| 33 | 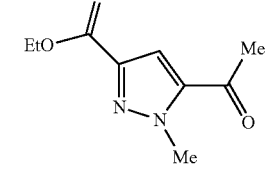 C_9H_{12}N_2O_3 |
| 34 | 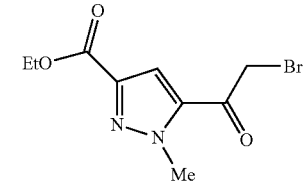 C_9H_{11}BrN_2O_3 |
| 35 | 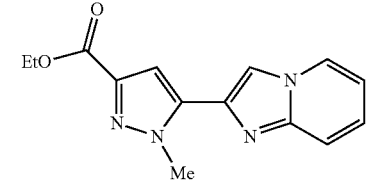 C_{14}H_{14}N_4O_2 |
| 36 | 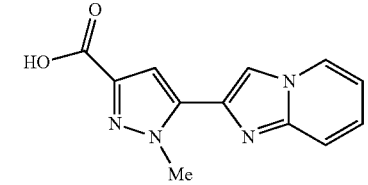 C_{12}H_{10}N_4O_2 |
| 37 | 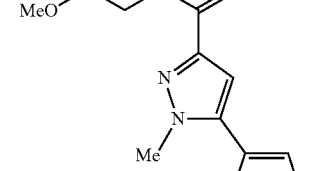 C_{17}H_{19}FN_4O_3 |

TABLE 11-3
| Intermediate number | Structure |
|---|---|
| 38 | 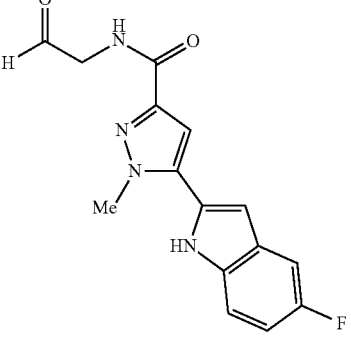 C₁₅H₁₃FN₄O₂ |
| 39 | 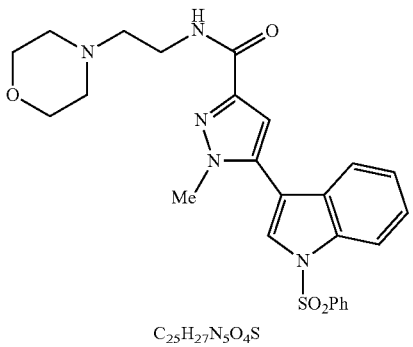 C₂₅H₂₇N₅O₄S |
| 49 | 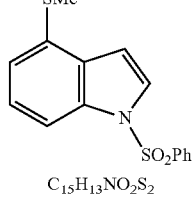 C₁₅H₁₃NO₂S₂ |
| 50 | 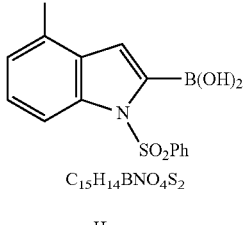 C₁₅H₁₄BNO₄S₂ |
| 51 | 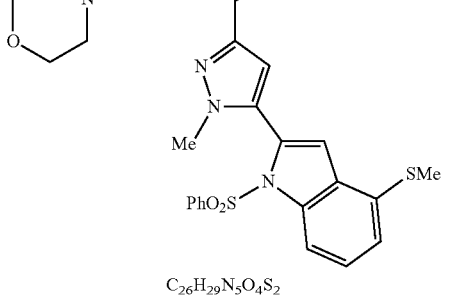 C₂₆H₂₉N₅O₄S₂ |
| 52 | 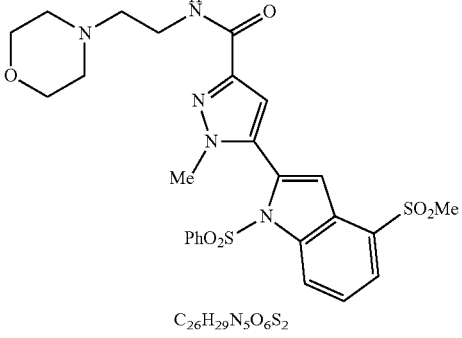 C₂₆H₂₉N₅O₆S₂ |
| 53 | 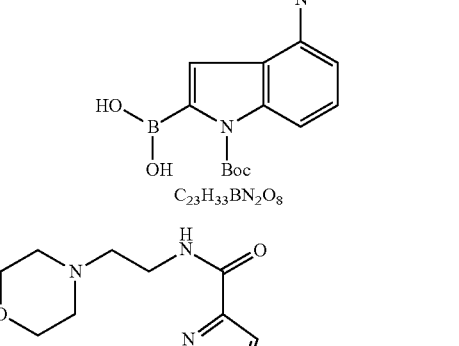 C₂₃H₃₃BN₂O₈ |
| 54 | 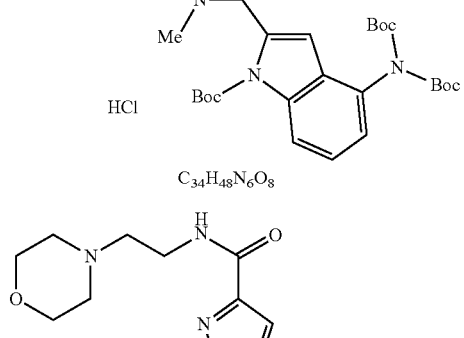 HCl C₃₄H₄₈N₆O₈ |
| 55 | 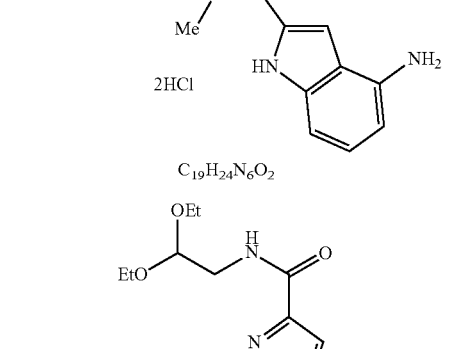 2HCl C₁₉H₂₄N₆O₂ |
| 56 | 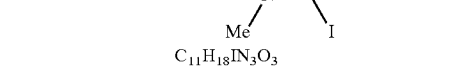 C₁₁H₁₈IN₃O₃ |

TABLE 11-3-continued
| Intermediate number | Structure |
|---|---|
| 57 | 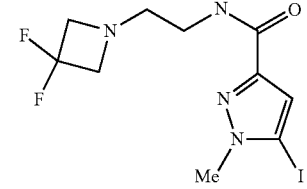<br>C₁₀H₁₃F₂IN₄O |
| 58 | 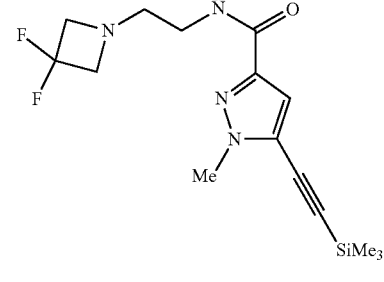<br>C₁₅H₂₂F₂N₄OSi |
| 59 | 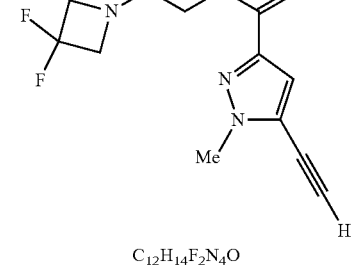<br>C₁₂H₁₄F₂N₄O |
| 60 | 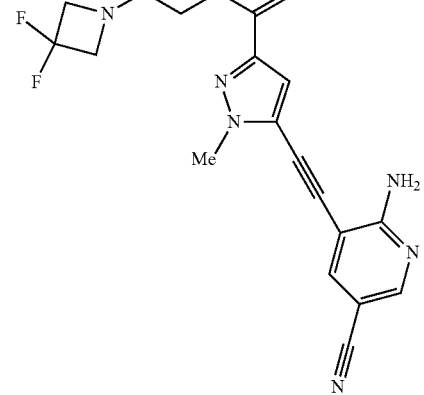<br>C₁₈H₁₇F₂N₇O |
TABLE 11-3-continued
| Intermediate number | Structure |
|---|---|
| 61 | 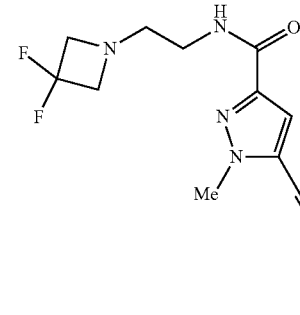<br>C₁₇H₁₈F₂N₆O |
| 62 | 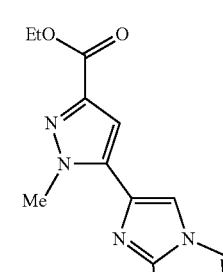<br>C₁₄H₁₃FN₄O₂ |
| 63 | 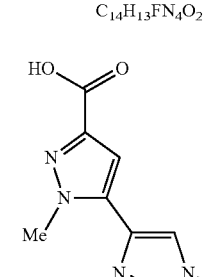<br>C₁₂H₉FN₄O₂ |
| 64 | 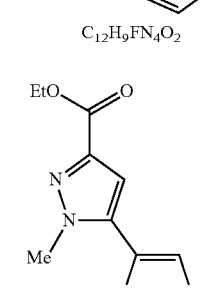<br>C₁₄H₁₃FN₄O₂ |

TABLE 11-4

| Intermediate number | Structure |
|---|---|
| 65 | 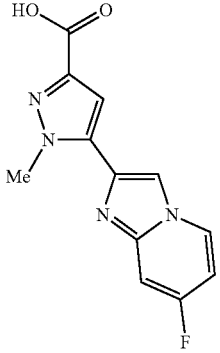 C₁₂H₉FN₄O₂ |
| 66 | 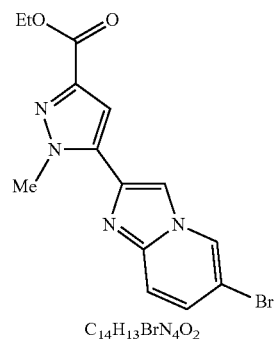 C₁₄H₁₃BrN₄O₂ |
| 67 | 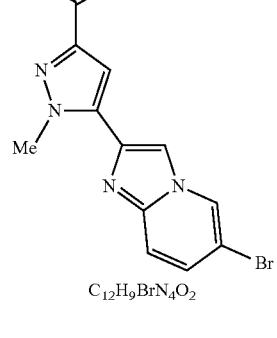 C₁₂H₉BrN₄O₂ |
| 68 | 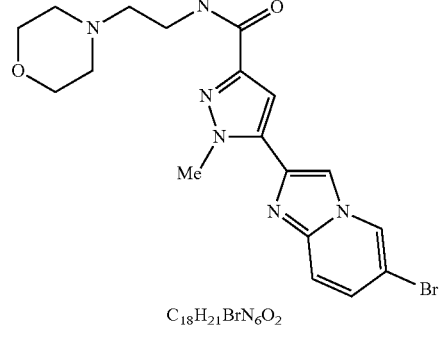 C₁₈H₂₁BrN₆O₂ |

TABLE 11-4-continued

| Intermediate number | Structure |
|---|---|
| 69 | 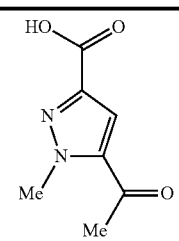 C₇H₈N₂O₃ |
| 70 | 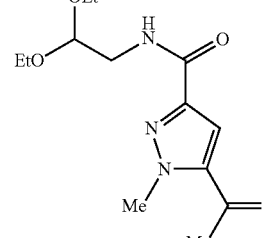 C₁₃H₂₁N₃O₄ |
| 71 | 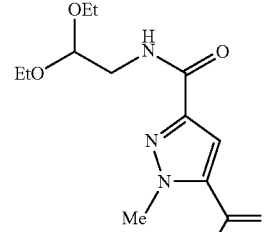 C₁₃H₂₀BrN₃O₄ |
| 72 | 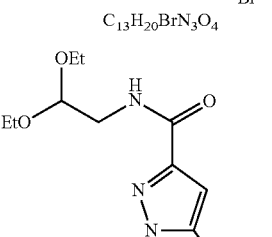 C₁₉H₂₂N₆O₃ |

[Human 5-HT2B Binding Assay]

The 5-HT2B receptor binding affinities of the compounds of this invention are determined by the following procedures.

Human 5-HT$_{2B}$ transfected CHO—K1 cells were got from Euroscreen (cat No.: ES-314-F) and grown in-house. The collected cells were suspended in 50 mM HEPES (pH 7.4) supplemented with protease inhibitor cocktail (SIGMA, 1:100 dilution) and 1 mM EDTA, and homogenized using a Polytron PT1200 disrupter set at full power for 30 seconds on ice. The homogenates were centrifuged at 1,000 rpm at 4° C. for 5 min and the supernatants were frozen at −80° C. for 10 min. The frozen supernatants were then re-suspended in 50 mM HEPES (pH 7.4), homogenized and centrifuged once more in the same manner. The supernatants were centrifuged at 25,000 rpm at 4° C. for 60 min. The pellets were then re-suspended in 50 mM HEPES (pH 7.4), homogenized, divided and stored at −80° C. until use. An aliquot of membrane fractions was used for protein concentration determination using BCA protein assay kit (PIERCE) and ARVOsx plate reader (Wallac).

For the receptor binding experiments, 20 microL of test compounds were incubated with 100 microL of [$^3$H]-mesulergine (GE healthcare, 10 nM) and 80 microL of membrane homogenate (20 microg protein) for 120 min at room temperature. Nonspecific binding was determined by 10 microM mianserin (SIGMA) at the final concentration. All incubations were terminated by rapid vacuum filtration over 0.2(v/v) % PEI soaked glass filter papers using Filtrate harvester (PerkinElmer) followed by five washes with 50 mM HEPES (pH 7.4). Receptor-bound radioactivity was quantified by liquid scintillation counting using TopCount (Perkin Elmer).

As a result of the experiment, all compounds of examples showed human 5-HT$_{2B}$ receptor affinity.

[Calcium Influx Assay Using Human 5-HT$_{2B}$ Transfected CHO—K1 Cells]

The 5-HT$_{2B}$ receptor binding affinities of the compounds of this invention are determined by the following procedures. Human 5-HT$_{2B}$ transfected CHO—K1 cells were got from Euroscreen and grown. The cells were grown at 37° C. and 5% CO$_2$ in UltraCHO medium (Cambrex) supplemented with 400 microg/mL G418, 250 microg/mL zeocin, 100 U/mL penicillin, 100 microg/mL streptomycin and 1(v/v) % dialyzed FBS (fetal bovine serum). After growing to 60-80% confluence, the culture medium of the cells was replaced with KRH buffer (1.8 mM CaCl$_2$, 1 mM MgSO$_4$, 115 mM NaCl, 5.4 mM KCl, 11 mM $_D$-glucose, 0.96 mM NaH$_2$PO$_4$, 25 mM HEPES, adjusted to pH 7.4 with NaOH) including 5 microM Fura-2 AM. The cells were incubated for 120 min at room temperature. After incubation, the cells were detached with 0.05 (w/w) % Trypsin/1 mM EDTA and washed with PBS. Then these cells were suspended in KRH buffer to give 1.0× 10$^6$ cells/mL.

Compounds of this invention were prepared in 384-well plates (50 microL/well). The 34 microL of cell suspension (3.4×10$^4$ cells) was distributed into each well of 384-well black assay plate with transparent bottom. The assay plates were settled on the FDSS6000 (Hamamatsu Photonics), and the signal monitoring was started. Thirty seconds later, 6 microL of the serial dilutions of compounds were added to each well automatically, and the FDSS6000 continued to monitor in further 4.5 min for the examination of antagonistic activity. Then the cells were incubated for 10 min at room temperature under the dark. The assay plates were re-settled on the FDSS6000, and the signal monitoring was started. Thirty seconds later, 20 microL of 9 nM 5-HT was added to each well automatically, and the FDSS6000 continued to monitor in further 4.5 min for the examination of IC$_{50}$ values of the test compounds. This experiment was referred to Br. J. Pharmacol., 1999 September; 128(1): 13-20.

5-HT$_{2B}$ receptor antagonistic activities (IC50, nM) of all 88 compounds of examples shown by the following Table 12 to Table 15 were from 0.1 nM to 100 nM.

TABLE 12

Example compound number

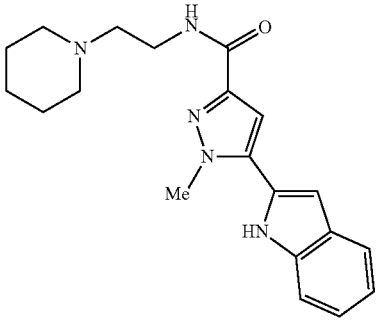

1

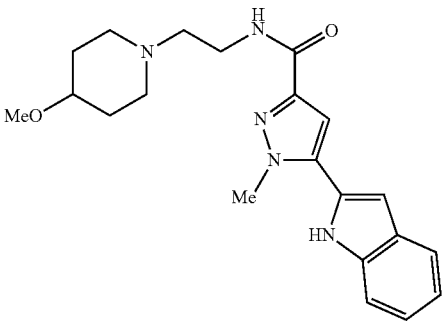

2

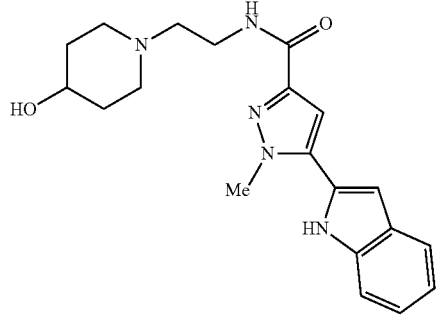

3

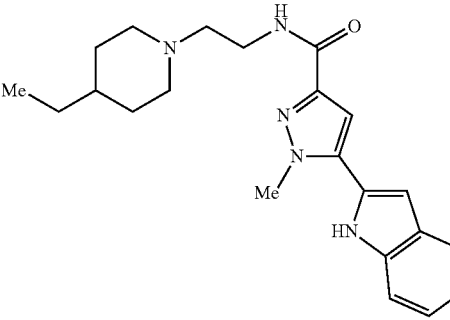

4

TABLE 12-continued
| Example compound number |
|---|
| 5 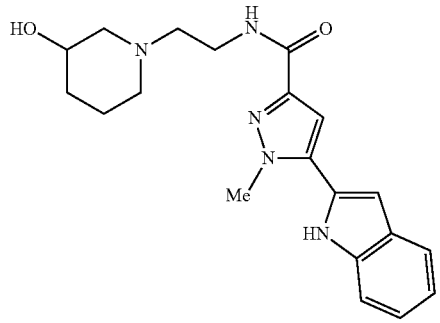 |
| 6 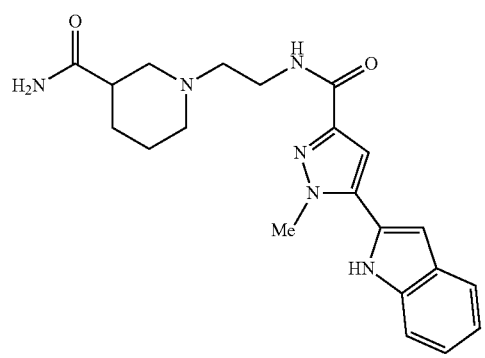 |
| 7 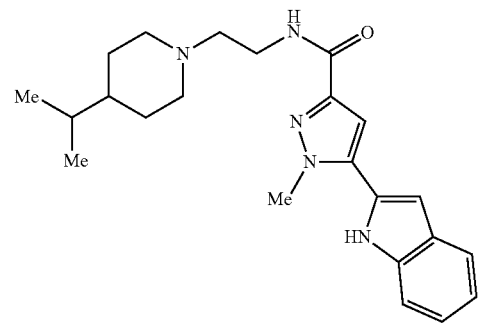 |
| 8 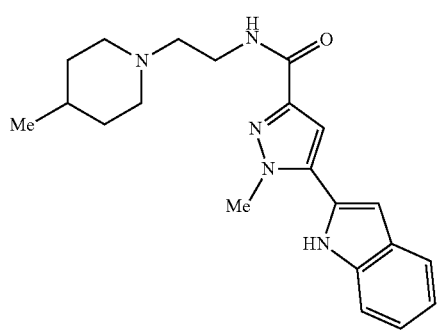 |
TABLE 12-continued
| Example compound number |
|---|
| 9 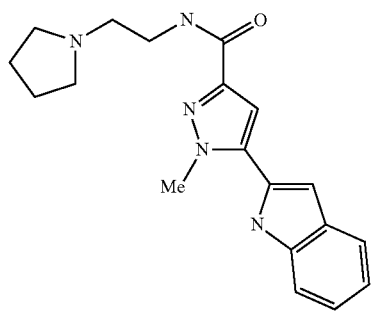 |
| 10 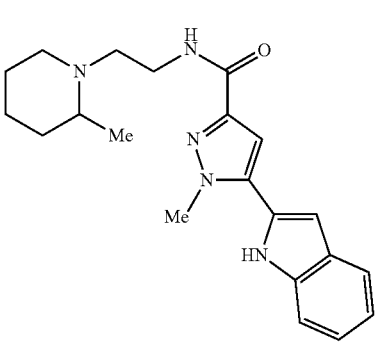 |
| 11 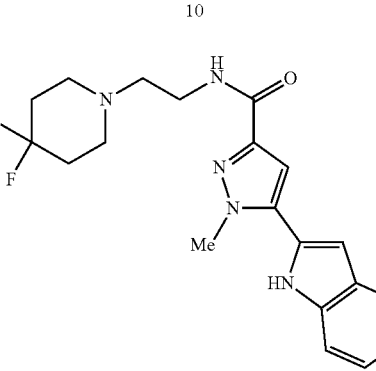 |
| 12 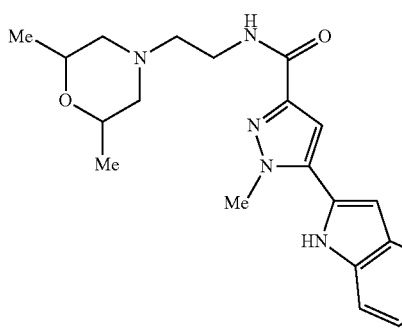 |

TABLE 12-continued
Example compound number
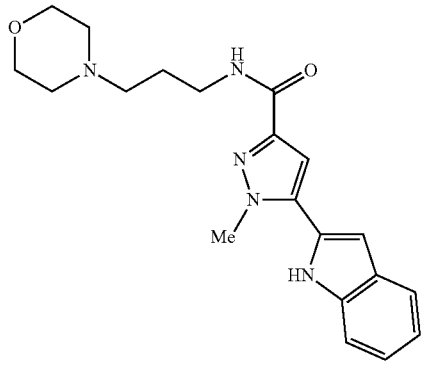
13
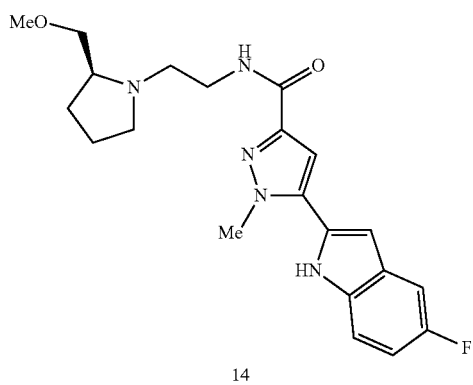
14
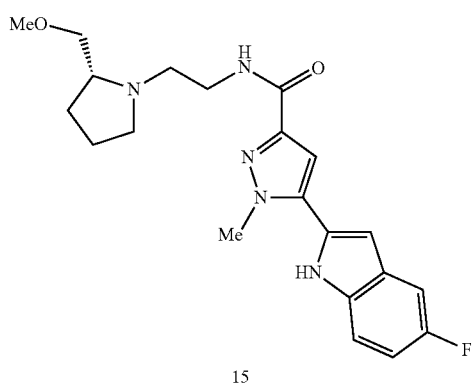
15
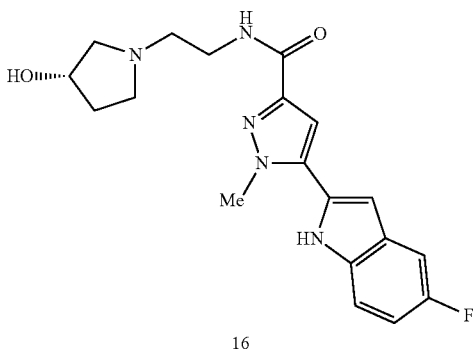
16
TABLE 12-continued
Example compound number
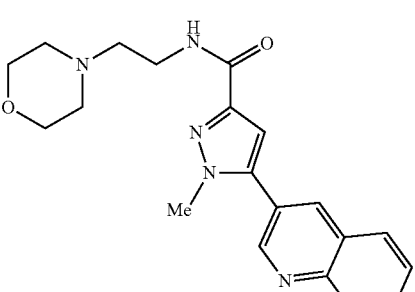
17
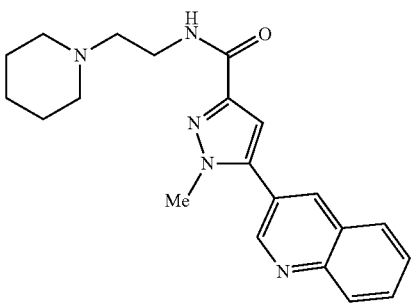
18
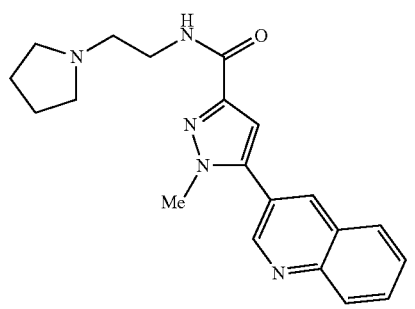
19
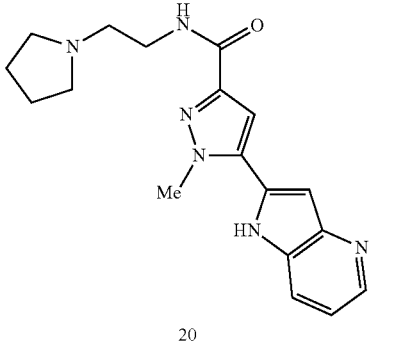
20

TABLE 12-continued
Example compound number
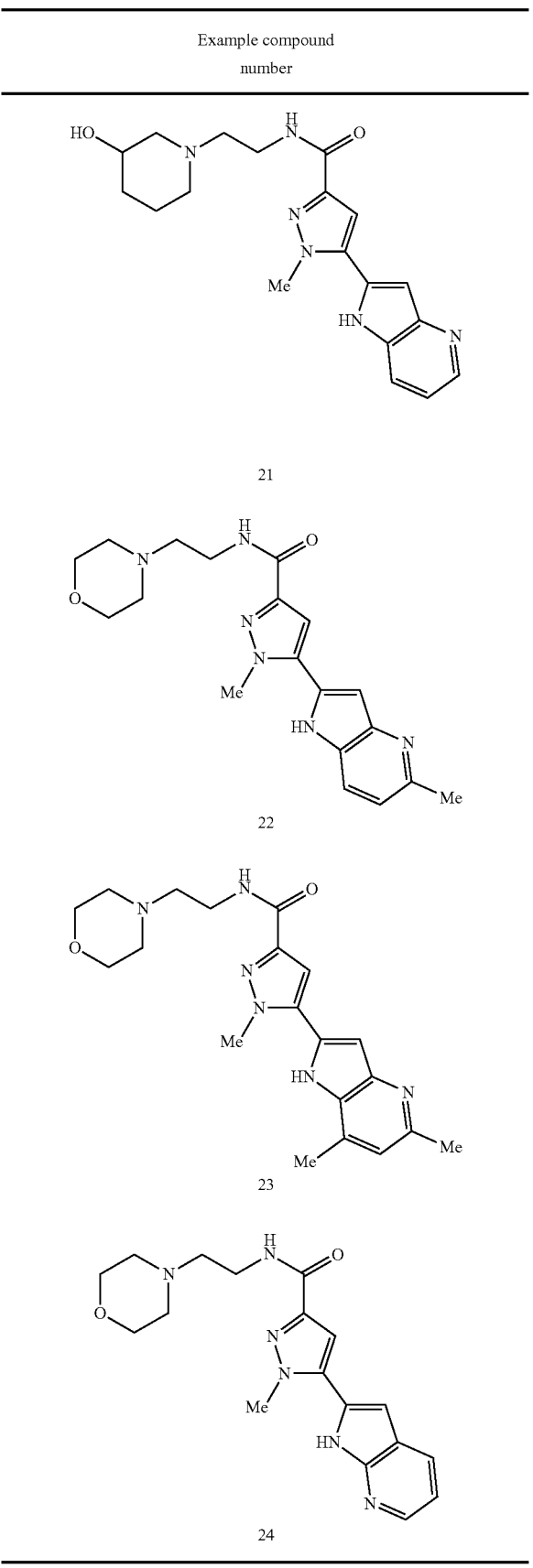
TABLE 13
Example compound number
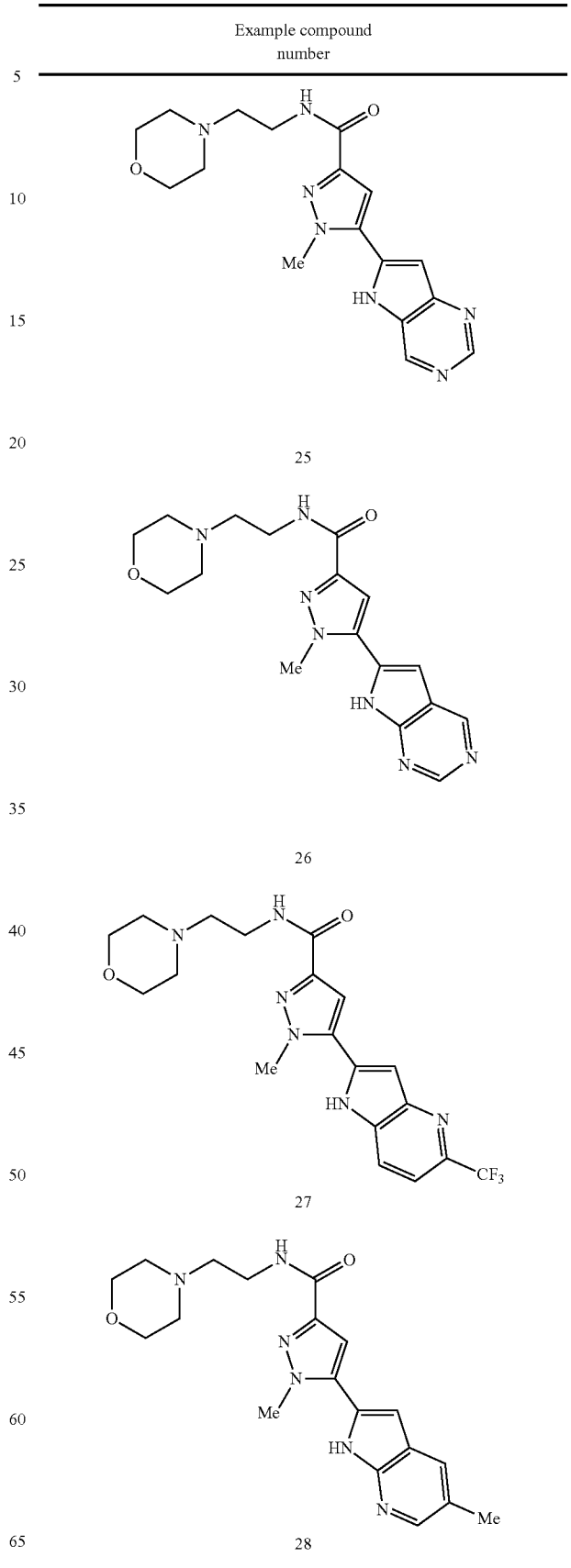

TABLE 13-continued
Example compound number
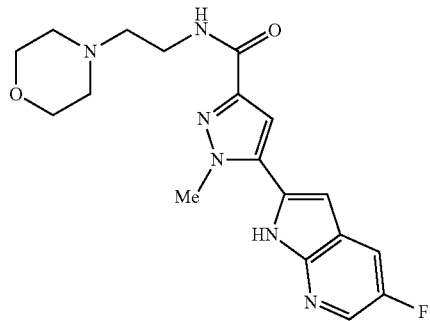
29
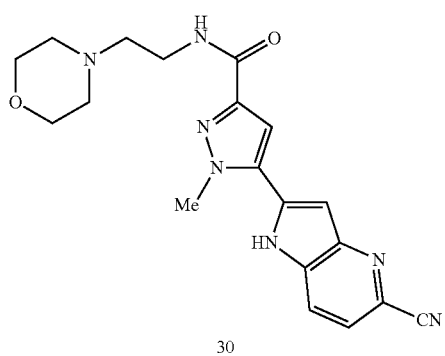
30
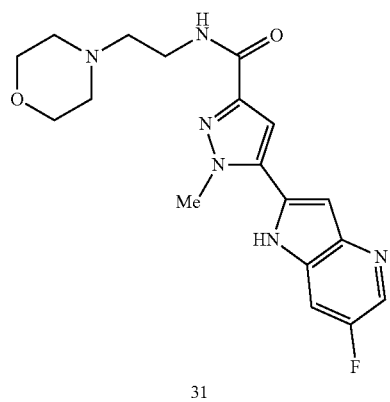
31
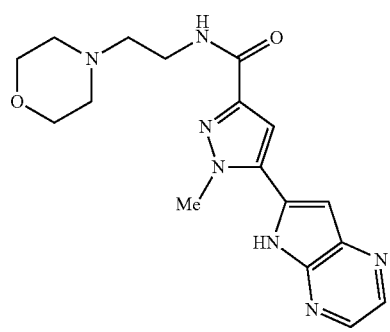
32
TABLE 13-continued
Example compound number
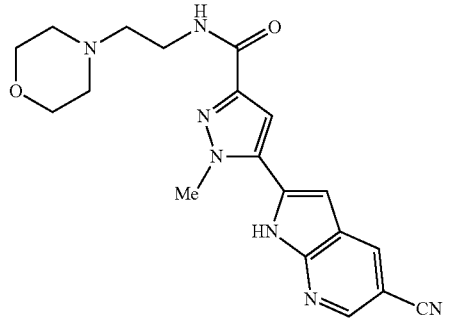
33
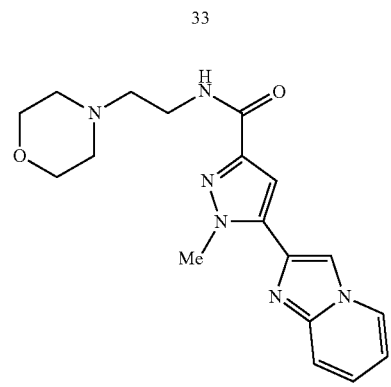
34
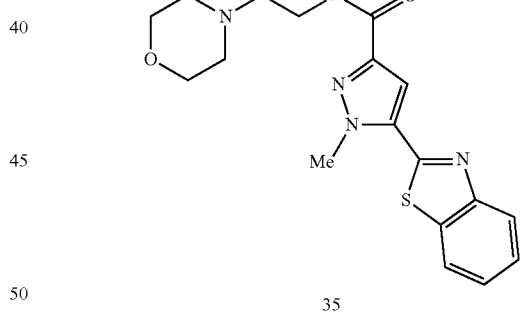
35
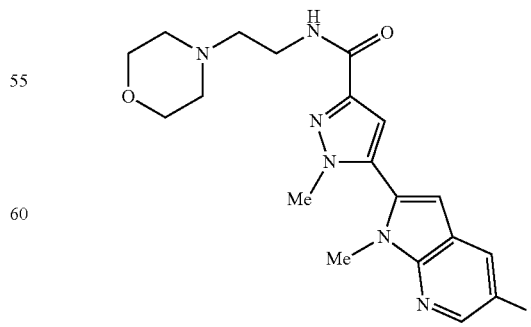
36

TABLE 13-continued
Example compound number
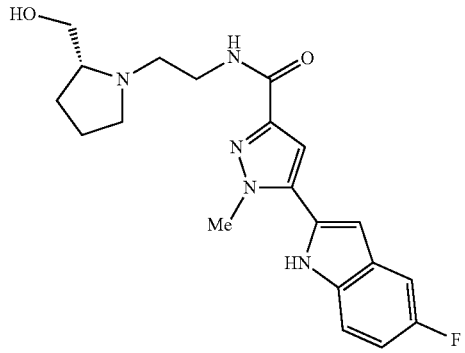
37
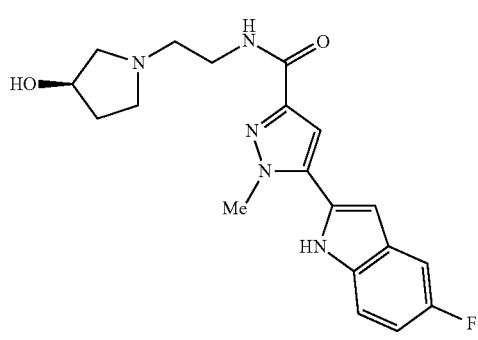
38
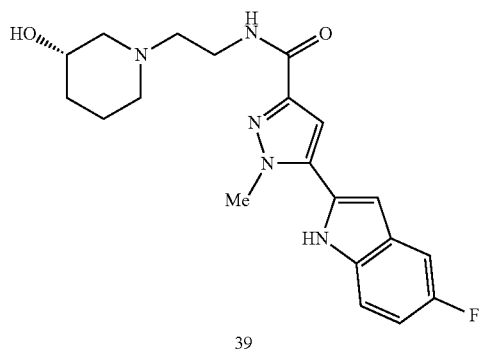
39
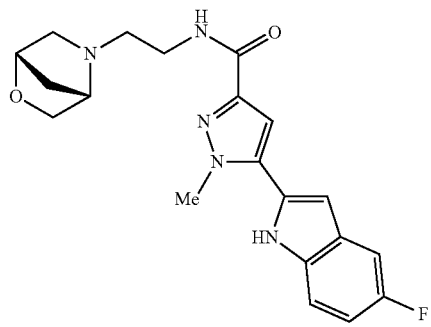
40
TABLE 13-continued
Example compound number
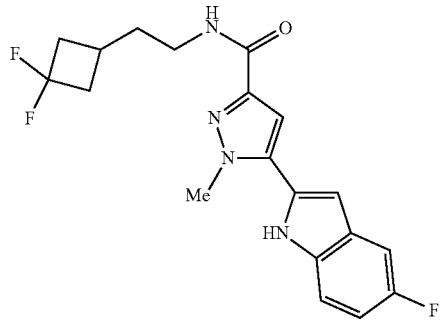
41
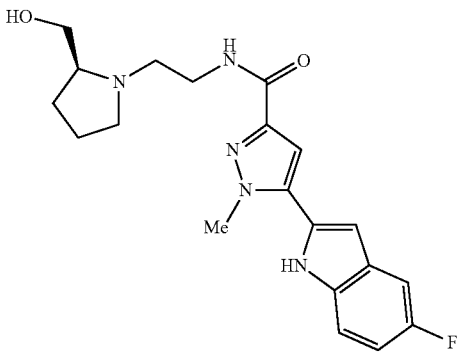
42
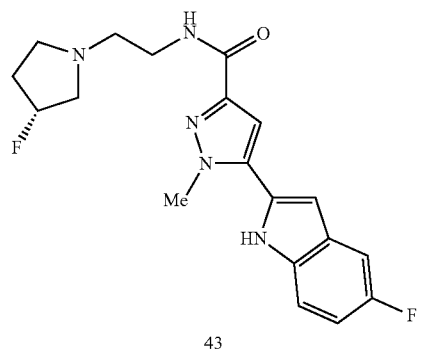
43
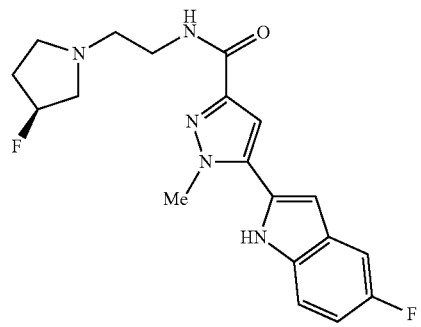
44

TABLE 13-continued
| Example compound number |
|---|
| 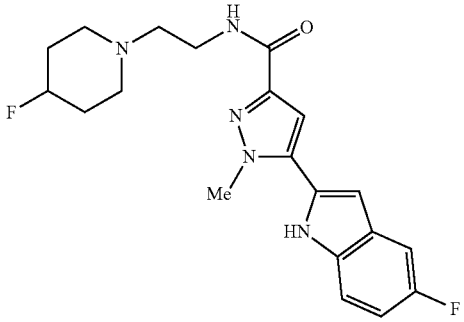 45 |
| 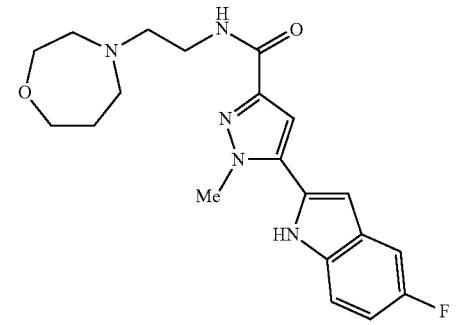 46 |
| 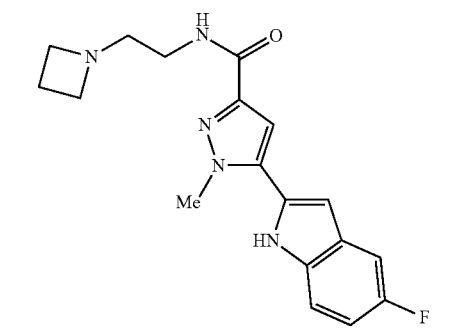 47 |
| 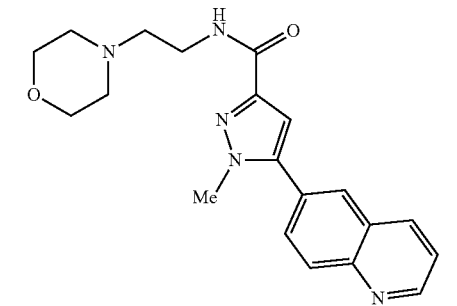 48 |
TABLE 14
| Example compound number |
|---|
| 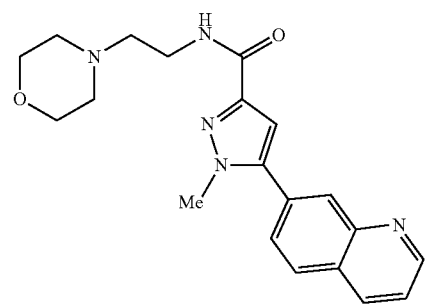 49 |
| 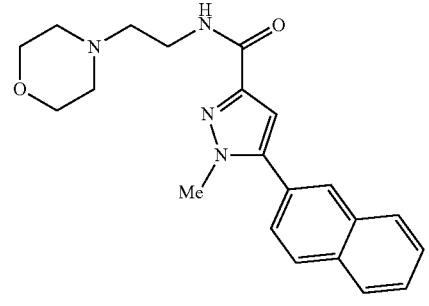 50 |
| 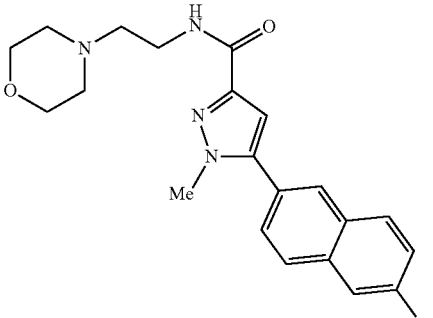 51 |
| 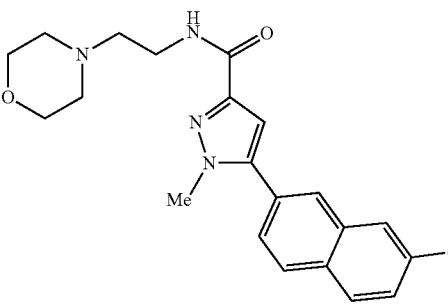 52 |

TABLE 14-continued
Example compound number
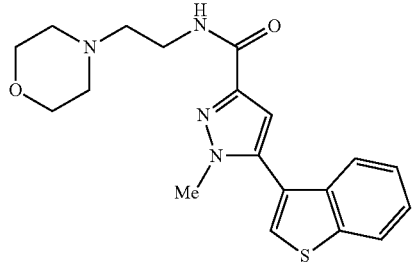
53
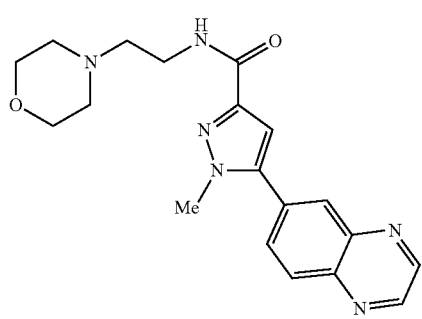
54
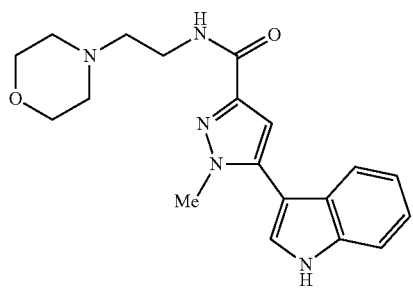
55
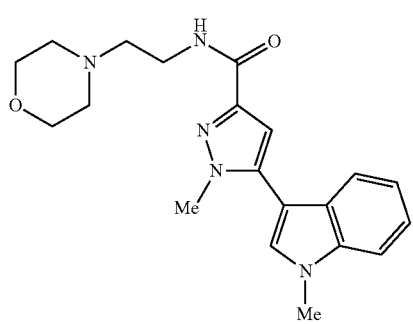
56
TABLE 14-continued
Example compound number
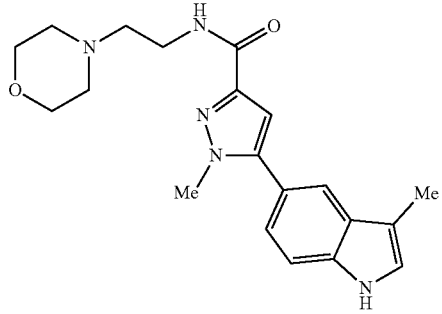
57
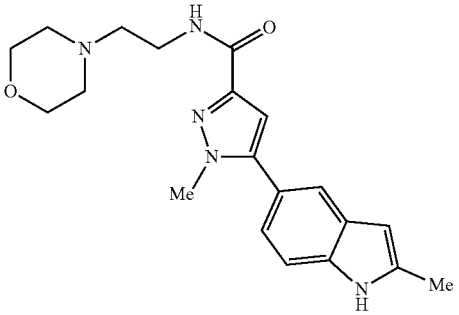
58
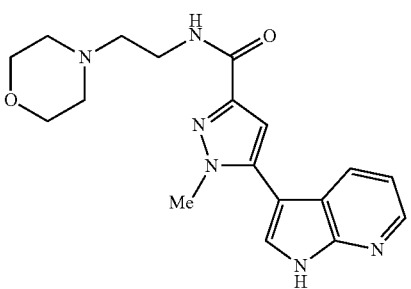
59
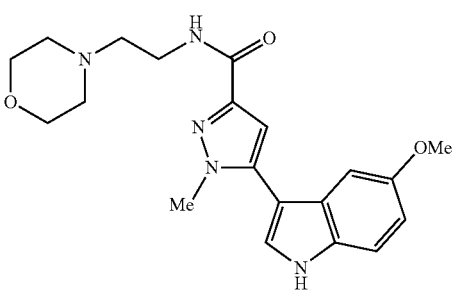
60

TABLE 14-continued
Example compound number
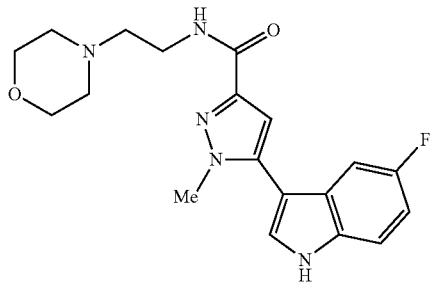
61
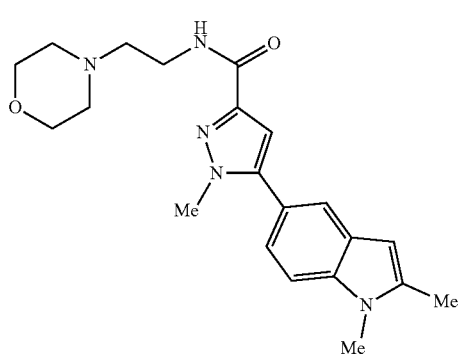
62
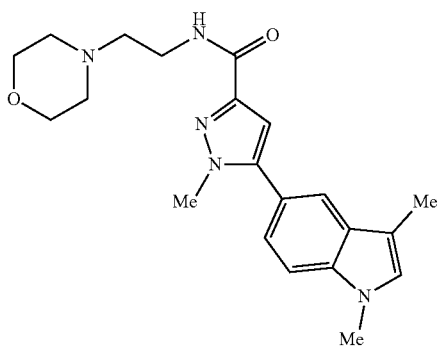
63
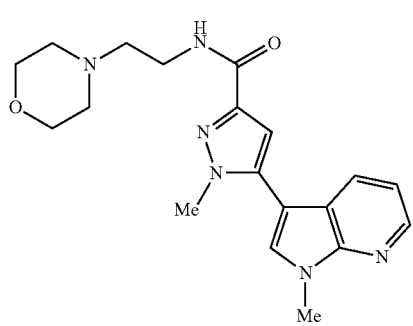
64
TABLE 14-continued
Example compound number
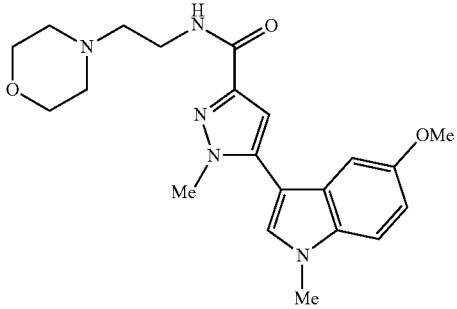
65
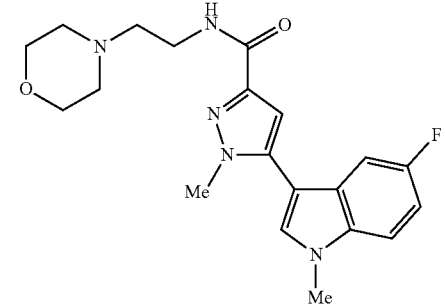
66
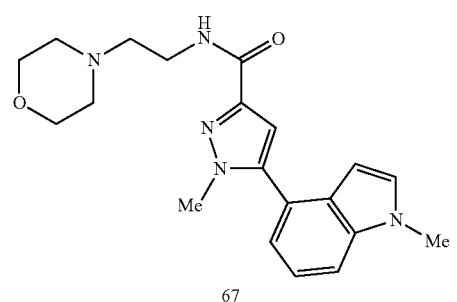
67
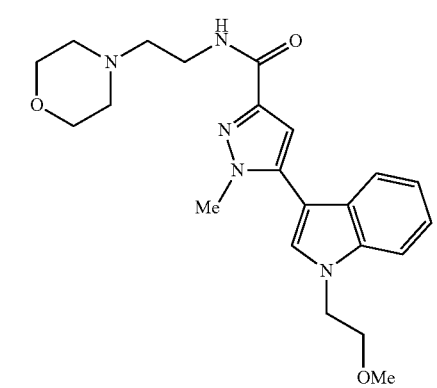
68

TABLE 14-continued
Example compound number
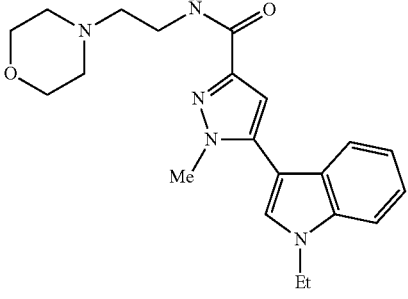
69
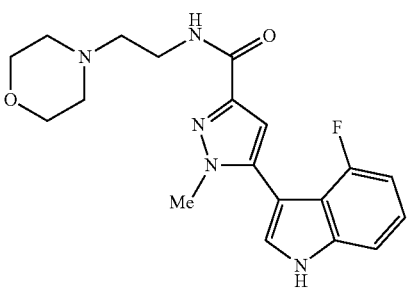
70
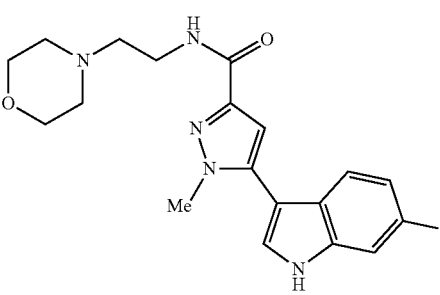
71
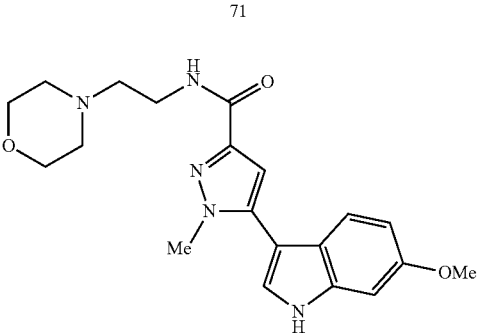
72
TABLE 15
Example compound number
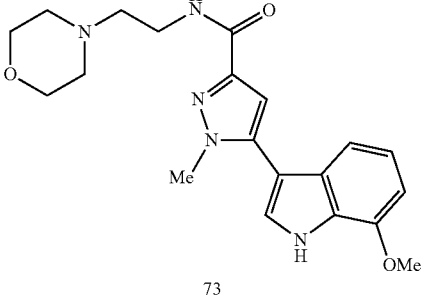
73
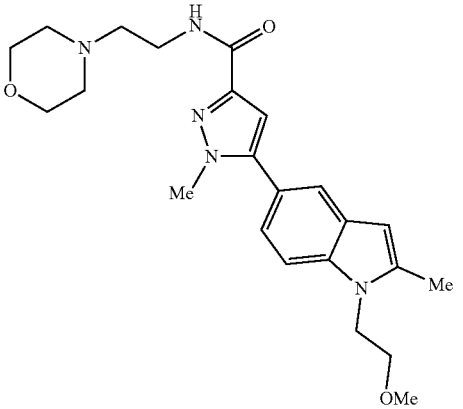
74
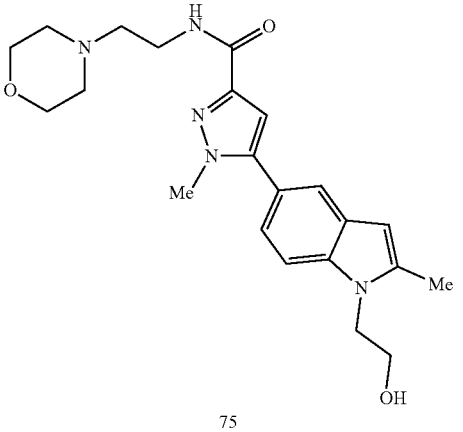
75
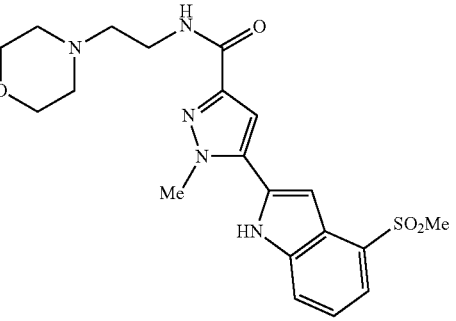
76

TABLE 15-continued
Example compound number
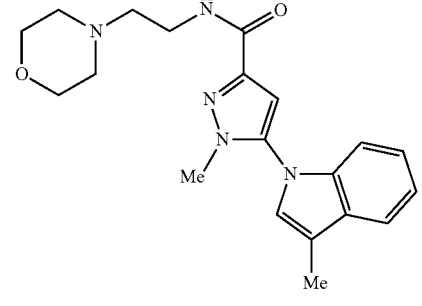
77
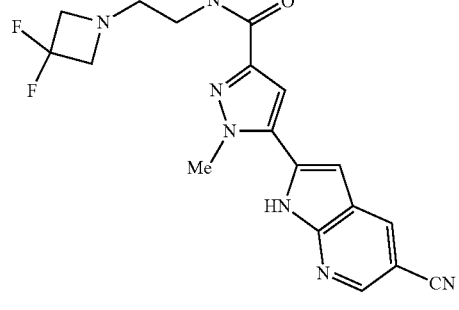
78
79
80
81
82
83
84

TABLE 15-continued

Example compound number

85

86

87

88

[Calcium Influx Assay Using Human 5-HT$_{2B}$ Transfected 3T3 Cells]

The 5-HT$_{2B}$ receptor binding affinities of the compounds of this invention are determined by the following procedures.

Human 5-HT$_{2B}$ transfected 3T3 cells were prepared in house. The cells were grown at 37° C. and 5% CO$_2$ in DMEM medium (Invitrogen) supplemented with 400 microg/mL G418, 100 U/mL penicillin, 100 microg/mL streptomycin and 10 (v/v) % FBS. After growing to 60-80% confluence, the culture medium of the cells was replaced with KRH buffer (1.8 mM CaCl$_2$, 1 mM MgSO$_4$, 115 mM NaCl, 5.4 mM KCl, 11 mM D-glucose, 0.96 mM NaH$_2$PO$_4$, 25 mM HEPES, adjusted to pH 7.4 with NaOH) including 5 microM Fura-2 AM. The cells were incubated for 120 min at room temperature. After incubation, the cells were detached with 0.05% Trypsin/1 mM EDTA and washed with PBS. These cells were suspended in KRH buffer to give 0.3×10$^6$ cells/mL.

Compounds of this invention were prepared in 384-well plates (50 microL/well). The 34 microL of cell suspension (1.0×10$^4$ cells) was distributed into each well of 384-well black assay plate with transparent bottom. The assay plates were settled on the FDSS6000 (Hamamatsu Photonics), and the signal monitoring was started. Thirty seconds later, 6 microL of the serial dilutions of compounds were added to each well automatically, and the FDSS6000 continued to monitor in further 4.5 min for the examination of antagonistic activity. Then the cells were incubated for 10 min at room temperature under the dark. The assay plates were re-settled on the FDSS6000, and the signal monitoring was started. Thirty seconds later, 20 microL of 90 nM 5-HT was added to each well automatically, and the FDSS6000 continued to monitor in further 4.5 min for the examination of IC$_{50}$ values of the test compounds. This experiment was referred to Br. J. Pharmacol., 1999 September; 128(1): 13-20.

[Calcium Influx Assay Using Human 5-HT$_{2C}$ Transfected 3T3 Cells]

The 5-HT$_{2C}$ receptor binding affinities of the compounds of this invention are determined by the following procedures.

Human 5-HT$_{2C}$ transfected 3T3 cells were prepared in house. The cells were grown at 37° C. and 5% CO$_2$ in DMEM medium (Invitrogen) supplemented with 20 microg/mL G418, 100 U/mL penicillin, 100 microg/mL streptomycin and 10 (v/v) % FBS. After growing to 60-80% confluence, the culture medium of the cells was replaced with KRH buffer (1.8 mM CaCl$_2$, 1 mM MgSO$_4$, 115 mM NaCl, 5.4 mM KCl, 11 mM D-glucose, 0.96 mM NaH$_2$PO$_4$, 25 mM HEPES, adjusted to pH 7.4 with NaOH) including 5 microM Fura-2 AM. The cells were incubated for 120 min at room temperature. After incubation, the cells were detached with 0.05% Trypsin/1 mM EDTA and washed with PBS. These cells were suspended in KRH buffer to give 0.45×10$^6$ cells/mL.

Compounds of this invention were prepared in 384-well plates (50 microL/well). The 34 microL of cell suspension (1.5×10$^4$ cells) was distributed into each well of 384-well black assay plate with transparent bottom. The assay plates were settled on the FDSS6000 (Hamamatsu Photonics), and the signal monitoring was started. Thirty seconds later, 6 microL of the serial dilutions of compounds were added to each well automatically, and the FDSS6000 continued to monitor in further 4.5 min for the examination of antagonistic activity. Then the cells were incubated for 10 min at room temperature under the dark. The assay plates were re-settled on the FDSS6000, and the signal monitoring was started. Thirty seconds later, 20 microL of 3 nM 5-HT was added to each well automatically, and the FDSS6000 continued to monitor in further 4.5 min for the examination of IC$_{50}$ values of the test compounds. This experiment was referred to Br. J. Pharmacol., 1999 September; 128(1): 13-20.

[Evaluation of Therapeutic Effects on IBS in the Rat]

The pharmacological effects of the test compounds in this invention was evaluated by measuring the improvement effect against lowering of the pain threshold at colon extension stimulation in TNBS induced IBS model.

For details, please refer to the literature, Katsuyo Ohashi at al., Pharmacology, 81(2): 144-150 (2008).

Experimental Method

The median incision was conducted under anesthesia in animals, male SD rats, 240-270 g. TNBS solution (50 mg/kg, 30% methanol) was treated at the beginning of the colon in the rats. After the treatment, the cecum is put back into the abdominal cavity. The muscle wall is then sutured. After operation the animals were housed in the normal environment, and were used for the pharmacological evaluation after 7 days from the surgery. The colon extension stimulation was used for the evaluation of the compounds, Diop L. et al., J Pharmacol Exp Ther. 302(3): 1013-22 (2002). The balloon (5 cm in length) is inserted through the anus and kept in position (tip of balloon is 5 cm from the anus). Then the balloon was progressively inflated by step of 5 mm Hg, from 0 to 70 mm Hg by using Barostat (Barostat DISTENDER II R, G & J, CANADA). The pain threshold was evaluated the pressure that corresponded to produced the first abdominal contraction (abdominal cramp: Wesselmann U et al., (1998) Neurosci Lett 246: 73-76).

The result of Example compound 24 was shown in FIG. 1. The number of animals is 8 in each group. Data in the graph showed a median. The bar showed 25% and 75% values. The statistical analysis was conducted with closed test using Mann-whitney test.

The vertical axis showed a pain threshold pressure. In this case, 10 mg/kg p.o. gave the improvement effects against lowering of the pain threshold in TNBS. Therefore, novel pyrazol-3-carboxamide derivatives can be useful for the treatment of IBS.

INDUSTRIAL APPLICABILITY

A compound of this invention is useful as a selective antagonist of a 5-$HT_{2B}$ receptor, and is useful for pretreatment or prevention of various diseases associated with a 5-$HT_{2B}$ receptor.

The invention claimed is:

1. A compound of the following general formula (I) or its pharmaceutically acceptable salt,

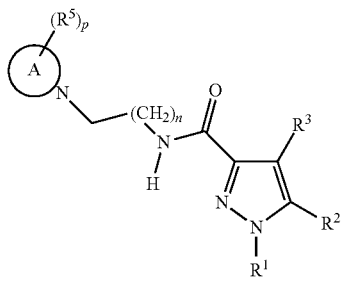

(I)

wherein,
A is a 3 to 8 membered ring and may contain 0 to 4 heteroatoms selected from O, S, and N;
$R^1$ is a $C_1$-$C_6$ alkyl group, or a $C_1$-$C_6$ haloalkyl group;
$R^2$ is a saturated or partially or all unsaturated monocyclic or bicyclic aryl group, which may be substituted by $R^4$;
$R^3$ is a hydrogen or halogen atom;
$R^4$ is a $C_1$-$C_6$ alkyl group, a $C_1$-$C_6$ haloalkyl group, OH, $OR^{1A}$, halogen, —$(CH_2)aOH$, $CO_2H$, $CONH_2$, $CONHR^{1A}$, $CONR^{1A}R^{1A}$, CN, $COR^{1A}$, $NH_2$, $NHR^{1A}$, $NR^{1A}R^{1A}$, $NHCOR^{1A}$, $SR^{1A}$, $SOR^{1A}$, $SO_2R^{1A}$, $SO_2NH_2$, $SO_2NHR^{1A}$, $SO_2NR^{1A}R^{1A}$, or $NHSO_2R^{1A}$; when $R^4$ has two $R^{1A}$, they may be same or different, or $R^{1A}$ may combine with the other $R^{1A}$;
$R^5$ is a $C_1$-$C_6$ alkyl group, —$(CH_2)aOH$, —$(CH_2)aOR^{1B}$, halogen, $CONH_2$, $CONR^{1B}R^{1B}$, $COR^{1B}$, $SO_2R^{1B}$, —$OCH_2CH_2NR^{1B}R^{1B}$ or a $C_1$-$C_6$ haloalkyl group; when p is plural;
$R^5$ may be the same or different, or $R^5$ may combine with another $R^5$;
$R^{1A}$ and $R^{1B}$ are each independently a $C_1$-$C_6$ alkyl group or a $C_1$-$C_6$ haloalkyl group;
a is 0, 1, or 2;
n is 1, or 2; and
p is 0, 1, 2, 3, 4, or 5.

2. The compound or the pharmaceutically acceptable salt thereof, as described in claim 1, wherein $R^2$ is the following $Ar^1$, $Ar^2$, $Ar^3$, or $Ar^4$,

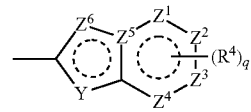

(Ar₁)

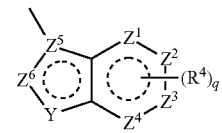

(Ar₂)

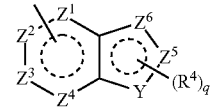

(Ar₃)

wherein,
$R^4$ is a $C_1$-$C_6$ alkyl group, a $C_1$-$C_6$ haloalkyl group, OH, $OR^{1A}$, halogen, —$(CH_2)aOH$, $CO_2H$, $CONH_2$, $CONHR^{1A}$, $CONR^{1A}R^{1A}$, CN, $COR^{1A}$, $NH_2$, $NHR^{1A}$, $NR^{1A}R^{1A}$, $NHCOR^{1A}$, $SR^{1A}$, $SOR^{1A}$, $SO_2R^{1A}$, $SO_2NH_2$, $SO_2NHR^{1A}$, $SO_2NR^{1A}R^{1A}$, or $NHSO_2R^{1A}$; when q is plural, $R^4$ may be the same or different; when $R^4$ has two $R^{1A}$, they may be the same or different, or $R^{1A}$ may combine with the other $R^{1A}$;
q is 0, 1, 2, or 3;
Y is NH, $NR^6$, O, or S;
$Z^1$, $Z^2$, $Z^3$, $Z^4$, $Z^5$, and $Z^6$ are each independently N, C, CH, or $CR^4$ (1, 2, or 3 of $Z^1$ to $Z^6$ may represent a nitrogen atom); and
$R^6$ is hydrogen, a $C_1$-$C_6$ alkyl group, a $C_1$-$C_6$ haloalkyl group, a $C_1$-$C_6$ alkoxy $C_1$-$C_6$ alkyl group, a hydroxyl $C_1$-$C_6$ alkyl group, a halo $C_1$-$C_6$ alkoxy $C_1$-$C_6$ alkyl group, a di$C_1$-$C_6$ alkylamino $C_1$-$C_6$ alkyl group, a mono $C_1$-$C_6$ alkylamino $C_1$-$C_6$ alkyl group, an amino $C_1$-$C_6$ alkyl group, a $C_3$-$C_8$ cyclo $C_1$-$C_6$ alkyl group (said $C_3$-$C_8$ cyclo $C_1$-$C_6$ alkyl group may be substituted with 1 or 2 groups each independently selected from hydroxy, $C_1$-$C_6$ alkoxy and $C_1$-$C_6$ acyloxy, and may have S(sulfur), O(oxygen) or $NR^1$), an aminocarbonyl $C_1$-$C_6$ alkyl group, a mono $C_1$-$C_6$ alkylaminocarbonyl $C_1$-$C_6$ alkyl group, a di $C_1$-$C_6$ alkylaminocarbonyl $C_1$-$C_6$ alkyl group, a hydroxycarbonyl $C_1$-$C_6$ alkyl group or a $C_1$-$C_6$ alkylsulfonyl group:

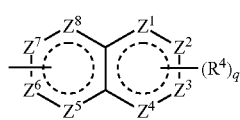

(Ar4)

wherein,

R⁴ and q are same as described above, and $Z^1, Z^2, Z^3, Z^4, Z^5, Z^6, Z^7$ and $Z^8$ are each independently N, C, CH, or $CR^4$ (1, 2, or 3 of $Z^1$ to $Z^8$ may represent a nitrogen atom.

3. The compound or the pharmaceutically acceptable salt thereof, as described in claim 2, wherein $Ar^1$, $Ar^2$, $Ar^3$, or $Ar^4$ is represented by the following general formula:

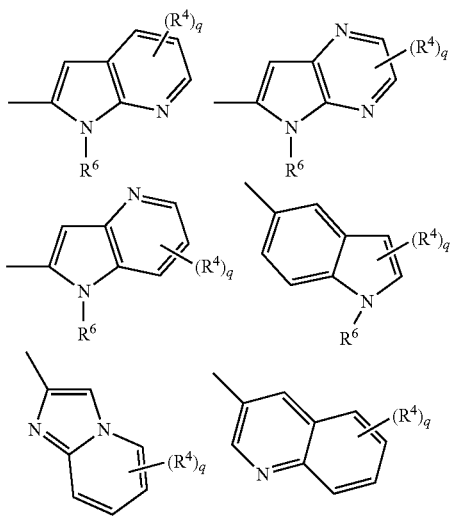

wherein,

R⁴ and q are same as described in claim 2;

R⁶ is hydrogen or a $C_1$-$C_6$ alkyl group; and $(R^4)_q$ may be a substitutent on one of the two rings or both rings.

4. The compound or the pharmaceutically acceptable salt thereof, as described in claim 2, wherein ring A is morpholine, piperidine, pyrrolidine, or azetidine which binds at N; n is 1;

p is 0, 1, or 2; and q is 0, 1, or 2.

5. The compound or the pharmaceutically acceptable salt thereof, as described in claim 1, wherein the compound represented by general formula (I) is selected from the group consisting of 1-methyl-N-[2-(morpholin-4-yl)ethyl]-5-(quinolin-3-yl)-1H-pyrazole-3-carboxamide;

1-methyl-5-{5-methyl-1H-pyrrolo[3,2-b]pyridin-2-yl}-N-[2-(morpholin-4-yl)ethyl]-1H-pyrazole-3-carboxamide;

1-methyl-N-[2-(morpholin-4-yl)ethyl]-5-{1H-pyrrolo[2,3-b]pyridin-2-yl}-1H-pyrazole-3-carboxamide;

1-methyl-N-[2-(morpholin-4-yl)ethyl]-5-{7H-pyrrolo[2,3-d]pyrimidin-6-yl}-1H-pyrazole-3-carboxamide;

1-methyl-N-[2-(morpholin-4-yl)ethyl]-5-[5-(trifluoromethyl)-1H-pyrrolo[3,2-b]pyridin-2-yl]-1H-pyrazole-3-carboxamide;

1-methyl-5-{5-methyl-1H-pyrrolo[2,3-b]pyridin-2-yl}-N-[2-(morpholin-4-yl)ethyl]-1H-pyrazole-3-carboxamide;

5-{5-fluoro-1H-pyrrolo[2,3-b]pyridin-2-yl}-1-methyl-N-[2-(morpholin-4-yl)ethyl]-1H-pyrazole-3-carboxamide;

5-{5-cyano-1H-pyrrolo[3,2-b]pyridin-2-yl}-1-methyl-N-[2-(morpholin-4-yl)ethyl]-1H-pyrazole-3-carboxamide;

5-{6-fluoro-1H-pyrrolo[3,2-b]pyridin-2-yl}-1-methyl-N-[2-(morpholin-4-yl)ethyl]-1H-pyrazole-3-carboxamide;

1-methyl-N-[2-(morpholin-4-yl)ethyl] 5-{5H-pyrrolo[2,3-b]pirazin-6-yl}-1H-pyrazole-3-carboxamide;

5-{5-cyano-1H-pyrrolo[2,3-b]pyridin-2-yl}-1-methyl-N-[2-(morpholin-4-yl)ethyl]-1H-pyrazole-3-carboxamide;

5-{5-fluoro1-methyl-1H-pyrrolo[2,3-b]pyridin-2-yl}-1-methyl-N-[2-(morpholin-4-yl)ethyl]-1H-pyrazole-3-carboxamide;

N-[2-(3,3-difluoroazetidin-1-yl)ethyl]-5-(5-fluoro-1H-indol-2-yl)-1-methyl-1H-pyrazole-3-carboxamide;

N-[2-(azetidin-1-yl)ethyl]-5-(5-fluoro-1H-indol-2-yl)-1-methyl-1H-pyrazole-3-carboxamide;

1-methyl-5-(2-methyl-1H-indol-5-yl)-N-[2-(morpholin-4-yl)ethyl]-1H-pyrazole-3-carboxamide;

5-(1,2-dimethyl-1H-indol-5-yl)-1-methyl-N-[2-(morpholin-4-yl)ethyl]-1H-pyrazole-3-carboxamide;

5-[1-(2-methoxyethyl)-1H-indol-3-yl]-1-methyl-N-[2-(morpholin-4-yl)ethyl]-1H-pyrazole-3-carboxamide;

5-(4-acetamido-1H-indol-2-yl)-1-methyl-N-[2-(morpholin-4-yl)ethyl]-1H-pyrazole-3-carboxamide;

5-{imidazo[1,2-a]pyridin-2-yl}-1-methyl-N-[2-(morpholin-4-yl)ethyl]-1H-pyrazole-3-carboxamide;

5-{6-fluoroimidazo[1,2-a]pyridin-2-yl}-1-methyl-N-[2-(morpholin-4-yl)ethyl]-1H-pyrazole-3-carboxamide;

5-{7-fluoroimidazo[1,2-a]pyridin-2-yl}-1-methyl-N-[2-(morpholin-4-yl)ethyl]-1H-pyrazole-3-carboxamide;

5-{6-cyanoimidazo[1,2-a]pyridin-2-yl}-1-methyl-N-[2-(morpholin-4-yl)ethyl]-1H-pyrazole-3-carboxamide;

N-[2-(3,3-difluoroazetidin-1-yl)ethyl]-1-methyl-5-(quinolin-3-yl)-1H-pyrazole-3-carboxamide;

N-[2-(3,3-difluoroazetidin-1-yl)ethyl]-1-methyl-5-{1H-pyrrolo[2,3-b]pyridin-2-yl}-1H-pyrazole-3-carboxamide; and 5-{7-cyanoimidazo[1,2-a]pyridin-2-yl}-1-methyl-N-[2-(morpholin-4-yl)ethyl]-1H-pyrazole-3-carboxamide.

6. A compound represented by the following general formula (1A):

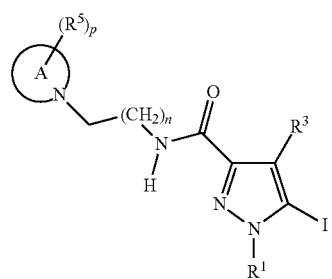

(IA)

wherein, A is a 3 to 8 membered ring and may contain 0 to 4 heteroatoms selected from O, S, and N;

$R^1$ is a $C_1$-$C_6$ alkyl group, or a $C_1$-$C_6$ haloalkyl group;

$R^3$ is a hydrogen or halogen atom;

$R^5$ is a $C_1$-$C_6$ alkyl group, —$(CH_2)_a$OH, —$(CH_2)aOR^1B$, halogen, $CONH_2$, $CONR^{1B}R^{1B}$, $COR^{1B}$, $SO_2R^{1B}$, —$OCH_2CH_2NR^{1B}R^{1B}$ or a $C_1$-$C_6$ haloalkyl group; when p is plural, $R^5$ may be the same or different, or $R^5$ may combine with another $R^5$;

$R^{1B}$ is a $C_1$-$C_6$ alkyl group or a $C_1$-$C_6$ haloalkyl group;

a is 0, 1, or 2;

n is 1, or 2; and p is 0, 1, 2, 3, 4, or 5.

7. A therapeutic agent for diseases in which 5-$HT_{2B}$ receptors are involved, wherein the compound or the pharmaceutically acceptable salt thereof, as described in claim 1, is an effective ingredient.

8. A pharmaceutical composition comprising the compound or the pharmaceutically acceptable salt thereof, as described and a pharmaceutically acceptable carrier.

9. A pharmaceutical composition for treatment of a disease condition mediated by 5-$HT_{2B}$ receptors, in a mammalian subject, comprising an effective amount of the compound or the pharmaceutically acceptable salt thereof, as described and a pharmaceutically acceptable carrier.

10. A pharmaceutical composition comprising the compound as described in claim 1 as a pharmacologically active agent, and further comprising another pharmacologically active agent.

11. The compound or the pharmaceutically acceptable salt thereof, as described in claim 1, for treatment of a disease condition mediated by 5-$HT_{2B}$ receptors.

12. A method of treatment for migraine, inflammatory pain, nociceptive pain, neuropathic pain, fibromyalgia, chronic low back pain, visceral pain, gastroesophageal reflux disease (GERD), constipation, diarrhea, functional gastrointestinal disorder, irritable bowel syndrome, asthma, osteoarthritis, rheumatoid arthritis, Crohn's disease, ulcerative colitis, glomerulonephritis, nephritis, dermatitis, hepatitis, vasculitis, renal ischemia, cerebral stroke, myocardial infarction, cerebral ischemia, Alzheimer's disease, reversible airway obstruction, adult respiratory disease syndrome, chronic obstructive pulmonary disease (COPD), pulmonary hypertension (PH), idiopathic interstitial pneumonia, bronchitis, liver fibrosis, cryptogenic fibrosing alveolitis, multiple sclerosis, depression, anxiety or obesity, which is characterized by administering an effective amount of a pharmaceutical composition, comprising the compound or the pharmaceutically acceptable salt thereof as described in claim 1 and a pharmaceutically acceptable carrier, to human or a mammalian subject.

* * * * *